US011466064B2

(12) United States Patent
Segal et al.

(10) Patent No.: US 11,466,064 B2
(45) Date of Patent: Oct. 11, 2022

(54) BCL-W POLYPEPTIDES AND MIMETICS FOR TREATING OR PREVENTING CHEMOTHERAPY-INDUCED PERIPHERAL NEUROPATHY AND HEARING LOSS

(71) Applicants: Dana-Farber Cancer Institute, Inc., Boston, MA (US); President and Fellows of Harvard College, Cambridge, MA (US)

(72) Inventors: Rosalind Segal, Brookline, MA (US); Loren D. Walensky, Newton, MA (US); Lisa Vaughn Goodrich, Newton, MA (US); Sarah Elizabeth Raissi, Waltham, MA (US); Maria F. Murphy, Revere, MA (US); Gregory H. Bird, Pelham, NH (US)

(73) Assignees: Dana-Farber Cancer Institute, Inc., Boston, MA (US); President and Fellows of Harvard College, Cambridge, MA (US)

( * ) Notice: Subject to any disclaimer, the term of this patent is extended or adjusted under 35 U.S.C. 154(b) by 176 days.

(21) Appl. No.: 16/326,493

(22) PCT Filed: Aug. 25, 2017

(86) PCT No.: PCT/US2017/048582
§ 371 (c)(1),
(2) Date: Feb. 19, 2019

(87) PCT Pub. No.: WO2018/039545
PCT Pub. Date: Mar. 1, 2018

(65) Prior Publication Data
US 2020/0352899 A1 Nov. 12, 2020

Related U.S. Application Data

(60) Provisional application No. 62/380,048, filed on Aug. 26, 2016.

(51) Int. Cl.
| | | |
|---|---|---|
| A61K 38/16 | (2006.01) | |
| A61K 38/10 | (2006.01) | |
| A61K 38/00 | (2006.01) | |
| A61P 25/04 | (2006.01) | |
| A61K 38/04 | (2006.01) | |
| C07K 5/00 | (2006.01) | |
| C07K 7/00 | (2006.01) | |
| C07K 16/00 | (2006.01) | |
| C07K 17/00 | (2006.01) | |
| C07K 14/47 | (2006.01) | |
| A61P 35/00 | (2006.01) | |
| A61K 31/337 | (2006.01) | |
| A61P 25/02 | (2006.01) | |
| C07K 7/08 | (2006.01) | |
| A61K 45/06 | (2006.01) | |
| A61K 38/17 | (2006.01) | |

(52) U.S. Cl.
CPC ........ *C07K 14/4747* (2013.01); *A61K 31/337* (2013.01); *A61K 38/10* (2013.01); *A61P 25/02* (2018.01); *A61P 35/00* (2018.01); *C07K 7/08* (2013.01); *A61K 38/00* (2013.01); *A61K 38/1761* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 5,446,090 | A | 8/1995 | Harris et al. |
| 5,789,201 | A | 8/1998 | Guastella |
| 6,348,558 | B1 | 2/2002 | Harris et al. |
| 7,723,468 | B2 | 5/2010 | Daffre et al. |
| 7,723,469 | B2 | 5/2010 | Walensky et al. |
| 8,592,377 | B2 | 11/2013 | Verdine et al. |
| 9,079,970 | B2 | 7/2015 | Walensky et al. |
| 10,106,590 | B2 | 10/2018 | Walensky et al. |
| 11,046,739 | B2 | 6/2021 | Walensky et al. |
| 2004/0067503 | A1 | 4/2004 | Tan et al. |
| 2005/0250680 | A1 | 11/2005 | Walensky et al. |
| 2010/0168388 | A1 | 7/2010 | Bernal et al. |
| 2010/0273704 | A1 | 10/2010 | Korsmeyer et al. |
| 2011/0263479 | A1 | 10/2011 | Jacobsen et al. |
| 2011/0318352 | A1 | 12/2011 | Walensky et al. |
| 2012/0270800 | A1 | 10/2012 | Verdine et al. |
| 2016/0031959 | A1 | 2/2016 | Walensky et al. |

(Continued)

FOREIGN PATENT DOCUMENTS

| | | |
|---|---|---|
| EP | 1997828 | 12/2008 |
| WO | WO 1999/14259 | 3/1999 |
| WO | WO 1999/34833 | 7/1999 |

(Continued)

OTHER PUBLICATIONS

Hu et al., Curr. Neuropharmacology 17:184-196 (2019) (Year: 2019).*

(Continued)

*Primary Examiner* — Thea D' Ambrosio
(74) *Attorney, Agent, or Firm* — Fish & Richardson P.C.

(57) ABSTRACT

Compositions and methods are provided for the treatment or prevention of chemotherapy-induced peripheral neuropathy and hearing loss in a subject in need thereof. The methods involve administering to the subject a bclw protein, a BH4 domain-containing fragment thereof, or a bclw mimetic. Also provided are exemplary bclw mimetics.

14 Claims, 16 Drawing Sheets

Specification includes a Sequence Listing.

(56) References Cited

U.S. PATENT DOCUMENTS

| | | | |
|---|---|---|---|
| 2019/0092822 | A1 | 3/2019 | Walensky et al. |
| 2022/0098260 | A1 | 3/2022 | Walensky et al. |

FOREIGN PATENT DOCUMENTS

| | | | | |
|---|---|---|---|---|
| WO | WO 2006/041835 | 4/2006 | | |
| WO | WO 2007/002217 | 1/2007 | | |
| WO | WO 2008/121767 | 10/2008 | | |
| WO | WO 2009/042237 | 4/2009 | | |
| WO | WO 2009/108261 | 9/2009 | | |
| WO | WO 2010/009350 | 1/2010 | | |
| WO | WO 2010/060112 | 5/2010 | | |
| WO | WO 2010/068684 | 6/2010 | | |
| WO | WO 2010/148335 | 12/2010 | | |
| WO | WO 2014/144768 | 9/2014 | | |
| WO | WO-2014144768 | A2 * | 9/2014 | ......... A61K 38/1761 |

OTHER PUBLICATIONS

Bird et al., "BAX activation is initiated at a novel interaction site," Nature, Oct. 2008, 455(7216):1076-1081.

Blackwell et al., "Highly Efficient Synthesis of Covalently Cross-Linked Peptide Helices by Ring-Closing Metathesis," Angew Chem Int Ed Engl., Dec. 1998, 37(23):3281-3284.

Brunel et al., "Synthesis of constrained helical peptides by thioether ligation: application to analogs of gp41," Chem. Commun., May 2005, 20:552-554.

Edwards et al., "Multimodal interaction with BCL-2 family proteins underlies the proapoptotic activity of PUMA BH3," Chem Biol, Jul. 2013, 20(7):888-902.

Fda.gov, [online], "Data Standards Manual (monographs)," Feb. 2018, retrieved on Apr. 19, 2021, retrieved from URL<www.fda.gov/Drugs/DevelopmentApprovalProcess/FormsSubmissionRequirements/ElectronicSubmissions/DataStandardsManualmonographs/default.htm>, 1 page.

Fenstemacher et al., "Campenot Cultures and Microfluidics Provide Complementary Platforms for Spatial Study of Dorsal Root Ganglia Neurons," Microfluidic and Compartmentalized Platforms for Neurobiological Research, Feb. 2015, 103:105-124.

Haney et al., "Promoting peptide α-helix formation with dynamic covalent oxime side-chain cross-links," Chem. Commun. (Camb)., Oct. 2011, 47(39):10915-10917.

Hsu et al., "Nonionic detergents induce dimerization among members of the Bcl-2 family," J. Biol. Chem., May 1997, 272(21):13829-13834.

Jackson et al., "General approach to the synthesis of short .alpha.-helical peptides," J. Am. Chem. Soc., Nov. 1991, 113(24):9391-9392.

Kawamoto et al., "Design of triazole-stapled BCL9 α-helical peptides to target the β-catenin/B-cell CLL/lymphoma 9 (BCL9) protein-protein interaction," J. Med Chem., Feb. 2012, 55(3):1137-1146.

Lau et al., "Functionalised staple linkages for modulating the cellular activity of stapled peptides," Chem. Sci., 2013, 5:1804-1809.

Leshchiner et al., "Direct activation of full-length proapoptotic BAK," Proc Natl Acad Sci USA, Mar. 2013, 110(11):E986-8995.

Lovell et al., "Membrane binding by tBid initiates an ordered series of events culminating in membrane permeabilization by Bax," Dec. 2008, 135(6):1074-1084.

Madden et al., "Synthesis of cell-permeable stapled peptide dual inhibitors of the p53-Mdm2/Mdmx interactions via photoinduced cycloaddition," Bioorg. Med. Chem. Lett., Mar. 2011, 21(5):1472-1475.

PCT Written Opinion in International Appln. No. PCT/US2014/029318, dated Oct. 29, 2014, 7 pages.

Phelan et al., "A General Method for Constraining Short Peptides to an α-Helical Conformation," J. Am. Chem. Soc., Jan. 1997, 119(3):455-460.

Schneider et al., "Symptoms: Chemotherapy-Induced Peripheral Neuropathy," Adv. Exp. Med. Biol., 2015, 862:77-87.

Shepherd et al., "Single turn peptide alpha helices with exceptional stability in water," J. Am. Chem. Soc., Mar. 2005. 127(9):2974 2983.

Smith, "The efferent neural supply to the vertebrate ear," Adv Otorhinolaryngol, 1973, 20:296-310.

Spokoyny et al., "A perfluoroaryl-cysteine S(N)Ar chemistry approach to unprotected peptide stapling," J. Am. Chem. Soc., Apr. 2013, 135(16):5946-5949

Synthetic Peptides: A Users Guide, Grant. Ed., 1992, W. H. Freeman & Co., New York, N.Y., Chapter 3, 109 pages.

Wilen, "Tables of Resolving Agents and Optical Resolutions," EX. Eliel, Ed., Univ. of Notre Dame Press, Notre Dame, IN, 1972, 35 pages.

Altschul et al., "Gapped BLAST and PSI-BLAST: a new generation of protein database search programs," Nucleic Acids Res., 1997, 25(17):3389-3402.

Appler et al., "Connecting the ear to the brain: Molecular mechanisms of auditory circuit assembly," Progress in Neurobiology, Apr. 2011, 93(4):488-508.

Argetsinger et al., "Tyrosines 868, 966, and 972 in die kinase domain of JAK2 are autophosphorylated and required for maximal JAK2 kinase activity," Mol Endocrinol. 2010, 24(5):1062-1076.

Aristoteli et al., "Evaluation of endogenous plasma peptide extraction methods for mass spectrometric biomarker discovery," Journal of Proteome Res., 2007, 6(2):571-581.

Australia Examination Report No. 1 for AU App. No. 2014228777, dated Nov. 27, 2017, 11 pages.

Autret et al., "Emerging Role for Members of the Bcl-2 Family in Mitochondrial Morphogenesis," Mol Cell, Nov. 2009, 36(3):355-363.

Baldwin et al., "A Genome-Wide Association Study Identifies Novel Loci for Paclitaxel-Induced Sensory Peripheral Neuropathy in CALGB 40101," Clin Cancer Res, Sep. 2012, 18(18):5099-5109.

Bang, et al., "Total chemical synthesis of crambin," J. Am. Chem. Soc., 2004, 126(5):1377-1383.

Barclay et al., "Inhibition of Pro-apoptotic BAX by a noncanonical interaction mechanism," Molecular cell. Mar. 2015, 57(5):873-886.

Barrientos et al., "Axonal degeneration is mediated by the mitochondrial permeability transition pore," The Journal of Neuroscience, Jan. 2011, 31(3):966-978.

Benbow et al. "Inhibition of paclitaxel-induced decreases in calcium signaling," J Biol Chem, Nov. 2012, 287(45)37907-37916.

Bennett et al., "Pathophysiology and animal models of cancer-related painful peripheral neuropathy," The Oncologist, 2010, 15(Suppl 2):9-12.

Bernal et al., "Epidermal Growth Factor Receptor Signaling Regulates Bax and Bcl-w Expression and Apoptotic Responses During Intestinal Adaptation in Mice," Gastroenterology, Feb. 2006, 130(2):412-423.

Bird et al., "Chemical Synthesis of Hydrocarbon-Stapled Peptides for Protein Interaction Research and Therapeutic Targeting," Current Protocols in Chemical Biology, Sep. 2011, 3(3):99-117.

Bird et al., "Hydrocarbon double-stapling remedies the proteolytic instability of a lengthy peptide therapeutic," Proc. Natl. Acad. Sci. U.S.A., 2010, 107(32):14093-8.

Bird et. al., "Synthesis and Biophysical Characterization of Stabilized a-Helices of BCL-2 Domains," Methods in Enzymology, 2008, 446:369-386.

Bito et al., "Ca(2+)/CREB/CBP-dependent gene regulation: a shared mechanism critical in long—term synaptic plasticity and neuronal survival," Cell Calcium, 2003, 34(4-5):425-430.

Blackwell et al., "Ring-closing metathesis of olefinic peptides: design, synthesis, and structural characterization of macrocyclic helical peptides," J. Org. Chem., 2001, 66(16):5291-5302.

Bobylev et al., "Paclitaxel inhibits mRNA transport in axons," Neurobiology of Disease, Jul. 2015, 82:321-331.

Boehmerle et al., "Chronic exposure to paclitaxel diminishes phosphoinositide signaling by calpain-mediated neuronal calcium sensor-1 degradation," Proceedings of the National Academy of Sciences of the United States of America, Jun. 2007, 104(26):11103-11108.

(56) References Cited

OTHER PUBLICATIONS

Bok et al., "Patterning and morphogenesis of the vertebrate inner ear," Int J Dev Biol, Aug. 2007, 51(6-7):521-533.
Braun et al., "Photoreactive stapled BH3 peptides to dissect the BCL-2 family interactome," Chem. Biol., 2010, 17(12):1325-1333.
Brewer et al., "Chemotherapy-induced peripheral neuropathy: Current status and progress," Gynecologic Oncology, Jan. 2016, 140(1):176-183.
Broglia et al., "Design of HIV-1-PR inhibitors that do not create resistance: blocking the folding of single monomers," Protein Sci., 2005, 14(10):2668-81.
Brown et al., "Morphology of labeled afferent fibers in the guinea pig cochlea," Comp Neurol, Jun. 1987, 260(4):591-604.
Carpio et al., "BCL-2 family member BOK promotes apoptosis in response to endoplasmic reticulum stress," PNAS, Jun. 2015, 112(23):7201-7206.
Cashman et al., "Mechanisms of distal axonal degeneration in peripheral neuropathies," Neurosci. Lett., Jun. 2015, 596:33-50.
Cavaletti et al., "The chemotherapy-induced peripheral neuropathy outcome measures standardization study: from consensus to the first validity and reliability findings," Ann Oncol, 2013, 24(2):454-462.
Chang et al., "Feedback regulation mediated by Bcl-2 and DARPP-32 regulates inositol 1,4,5-trisphosphate receptor phosphorylation and promotes cell survival," Proceedings of the National Academy of Sciences of the United States of America, 2014, 111(3):1186-1191.
Chen et al., "Structural insight into enhanced calcium indicator GCaMP3 and GCaMPJ to promote further improvement," Protein Cell, 2013, 4(4):299-309.
Chhibber et al., "Polygenic inheritance of paclitaxel-induced sensory peripheral neuropathy driven by axon outgrowth gene sets in CALGB 40101 (Alliance)," Pharmacogenomics J, Feb. 2014, 14(4):336-342.
Chipuk et al., "How do BCL-2 proteins induce mitochondrial outer membrane permeabilization?" Trends Cell. Biol., 2008, 18(4):157-164.
Choudhary et al., "MCL-1 and BCL-xL-dependent resistance to the BCL-2 inhibitor ABT-199 can be overcome by preventing PI3K/AKT/mTOR activation in lymphoid malignancies," Cell Death Dis. Jan. 2015, 6:e1593.
Cohen et al., "A competitive stapled peptide screen identifies a selective small molecule that overcomes MCL-1-dependent leukemia cell survival," Chem. Biol., 2012, 19(9):1175-1186.
Cole et al., "Sensory organ generation in the chicken inner ear: Contributions of Bone morphogenetic protein 4, Serrate1, and Lunatic fringe," J Comp Neurol, May 2000, 424(3):509-520.
Cosker et al., "Action in the axon: generation and transport of signaling endosomes," Curr Opin Neurobiol, Jun. 2008, 18(3):270-275.
Cosker et al. "Target-derived neurotrophins coordinate transcription and transport of bclw to prevent axonal degeneration," J Neurosci., Mar. 2013, 33(12):5195-5207.
Courchesne et al., "Sensory Neuropathy Due to loss of Bcl-w," J Neurosci., Feb. 2011, 31(5):1624-1634.
Cruickshanks et al., "Prevalence of Hearing Loss in Older Adults in Beaver Dam, Wisconsin: The Epidemiology of Hearing Loss Study," American Journal of Epidemiology, Nov. 1998, 148(9):879-886.
Cusack et al., "Distinct pathways mediate axon degeneration during apoptosis and axon-specific pruning," Nature Communications, May 2013, 4(1876):1-11.
Darnell et al., "HITS-CLIP: panoramic views of protein-RNA regulation in living cells, Wiley Interdiscip Rev RNA," 2010, 1(2):266-286.
Dejean et al., "Oligomeric Bax is a component of the putative cytochrome c release channel MAC, mitochondrial apoptosis-induced channel," Mol. Biol. Cell., 2005, 16(5):2424-2432.
Distelhorst et al., "Bcl-2 interaction with the inositol 1,4,5-trisphosphate receptor: role in Ca(2+) signaling and disease," Cell Calcium, Sep. 2011, 50(3):234-241.
Donnini et al., "Prevention of ischemic brain injury by treatment with the membrane penetrating apoptosis inhibitor, TAT-BH4," Cell Cycle, Apr. 2009, 8(8):1271-1278.
Eng et al., "An approach to correlate tandem mass spectral data of peptides with amino acid sequences in a protein database," J. Am. Soc. Mass Spectrom., 1994, 5(11):976-989.
Erlich et al., "Differential interactions between Beclin 1 and Bcl-2 family members," Autophagy, 2007, 3(6):561-568.
Felder et al., "Quantitative evaluation of cochlear neurons and computer-aided three-dimensional reconstruction of spiral ganglion cells in humans with a peripheral loss of nerve fibres," Hearing Research, Mar. 1997, 105(1-2):183-190.
Flores-Otero et al., "Reciprocal Regulation of Presynaptic and Postsynaptic Proteins in Bipolar Spiral Ganglion Neurons by Neurotrophins," J Neurosci, Dec. 2007, 27(51):14023-14034.
Friedman et al., "Eyal acts upstream of Tbx1, Neurogenin 1, NeuroD and the neurotrophins BDNF and NT-3 during inner ear development," Mech Dev, May 2005, 122(5):625-634.
Fritzsch et al., "Neurotrophins in the ear: their roles in sensory neuron survival and fiber guidance, Progress in Brain Research," A. Luigi & C. Laura (Eds.), 2004, 146: 265-278.
Fritzsch et al., "The combined effects of trkB and trkC mutations on the innervation of the inner ear," Int J Dev Neurosci, Oct. 1998, 16(6):493-505.
Gavathiotis et al., "BAX Activation is Initiated at a Novel Interaction Site," Nature, 2008, 455:1076-1081.
George et al., "Axotomy-induced axonal degeneration is mediated by calcium influx through ion-specific channels," The Journal of Neuroscience, Oct. 1995, 15(10):6445-6452.
Gerdts et al., "Sarm1-mediated axon degeneration requires both SAM and TIR interactions" J. Neurosci., Aug. 2013, 33(33):13569-13580.
Giraldez et al., "Regionalized Organizing Activity of the Neural Tube Revealed by the Regulation of lmx1 in the Otic Vesicle," Dev Biol, Nov. 1998, 203(1):189-200.
Gornstein et al., "The paradox of paclitaxel neurotoxicity: Mechanisms and unanswered questions," Neuropharmacology, Jan. 2014, 76(Pt A):175-183.
Greenberg et al., "Bcl-2 regulation of the inositol 1,4,5-trsphosphate receptor and calcium signaling in normal and malignant lymphocytes: potential new target for cancer treatment," Biochimica et Biophysica Acta, Oct. 2014, 1843(10):2205-2210.
Heerssen et al., "Dynein motors transport activated Trks to promote survival of target-dependent neurons," Nat. Neurosci, May 2004, 7(6):596-604.
Hirotani, Miki, NH2-terminal BH4 Domain of Bcl-2 Is Functional for Heterodimerization with Bax and Inhibition of Apoptosis, The Journal of Biological Chemistry vol. 274, No. 29, Issue of Jul. 16, p. 20415-20420, 1999.
Hopikins-Donaldson et al., "Induction of apoptosis and chemosensitization of mesothelioma cells by Bcl-2 and Bcl-xL antisense treatment," Int J Cancer, Aug. 2003, 106(2):160-166.
Hotchkiss et al., "TAT-BH4 and TAT-Bcl-xL Peptides Protect against Sepsis-Induced Lymphocyte Apoptosis In Vivo," J Immunol. May 2006, 176(9):5471-5477.
Hsu et al., "The mTOR-regulated phosphoproteome reveals a mechanism of mTORC1-mediated inhibition of growth factor signaling," Science, 2011, 332(6035):1317-1322.
Jero et al., "The Use of Preyer's Reflex in Evaluation of Hearing in Mice," Acta Oto-Laryngologica, 2001, 121(5):585-589.
Johnson et al., "Inner Ear and Kidney Anomalies Caused by IAP Insertion in an Intron of the Eya1 Gene in a Mouse Model of BOR Syndrome," Hum Mol Genet, Arp. 1999, 8(4):645-653.
Ju et al., "Anti-apoptotic therapy with a Tat fusion protein protects against excitotoxic insults in vitro and in vivo," Experimental Neurology, Dec. 2007, 210(2):602-607.
Jürgensmeier et al., "Bax directly induces release of cytochrome c from isolated mitochondria," Proc. Natl. Acad. Sci. U.S.A. 95(9):4997-5002, (1998).
Kanai et al., "Kinesin transports RNA: isolation and characterization of an RNA-transporting granule," Neuron, 2004, 43(4):513-525.

(56) References Cited

OTHER PUBLICATIONS

Keithley et al., "Age-related hearing loss and the ahl locus in mice," Hearing Research, Feb. 2004, 188(1-2):21-28.
Kiernan et al., "Sox2 is required for sensory organ development in the mammalian inner ear," Nature, Apr. 2005, 434(7036): 1031-1035.
Kim et al., "NeuroD-null mice are deaf due to a severe loss of the inner ear sensory neurons during development," Development, Jan. 2001, 128(3):417-426.
Koleva et al., "C/EBPα and DEK coordinately regulate myeloid differentiation," Blood, 2012, 119(21):4878-4888.
Koundakjian et al., "Auditory Neurons Make Stereotyped Wiring Decisions before Maturation of Their Targets," Journal of Neuroscience, Dec. 2007, 27(51):14078-14088.
Kristensson et al., "Neuritic transport of herpes simplex virus in rat sensory neurons in vitro. Effects of substances interacting with microtubular function and axonal flow [nocodazole, taxol and erythro-9-3-(2-hydroxynonyl)adenine]," J. Gen. Virol.Sep. 1986, 67(Pt 9): 2023-2028.
Kuan et al., "Mechanisms of programmed cell death in the developing brain," Trends Neurosci, Jul. 2000, 23(7):291-297.
Kumita et al., "Photo-control of helix content in a short peptide," Proc. Natl. Acad. Sci. U. S. A., Apr. 2000, 97(8):3803-3808.
Kuwana et al., "BH3 domains of BH3-only proteins differentially regulate Bax-mediated mitochondrial membrane permeabilization both directly and indirectly," Mol. Cell 17(4):525-535 (2005).
Labelle et al., "A stapled BIM peptide overcomes apoptotic resistance in hemotologic cancers," The Journal of Clinical Investigation, Jun. 1, 2012, vol. 122, No. 6, pp. 2018-2031.
Leandro-Garcia et al., "Genome-wide association study identifies ephrin type A receptors implicated in paclitaxel induced peripheral sensory neuropathy," Journal of Medical Genetics. Jun. 2013, 50(9):599-605.
Lee et al., "Photoreactive Stapled Peptides to Identify and Characterize BCL-2 Family Interaction Sites by Mass Spectrometry," Methods Enzymol, 2014, 544:25-48.
Li et al., "The fate mapping of the eleventh and twelfth day mouse otocyst: An in vitro study of the sites of origin of the embryonic inner ear sensory structures," J Morphol, Sep. 1978, 157(3):249-267.
Liberman et al., "Applications of neuronal labeling techniques to the study of the peripheral auditory system," J Acoust Soc Am, Feb. 1985, 78(1):312-319.
Liberman et al., "Morphological differences among radial afferent fibers in the cat cochlea: An electron-microscopic study of serial sections," Hearing Research, Jul. 1980, 3(1):45-63.
Liberman et al., "Morphometry of intracellularly labeled neurons of the auditory nerve: Correlations with functional properties," J Comp Neurol, Feb. 1984, 223(2):163-176.
Liberman et al., "The cochlear frequency map for the cat: Labeling auditory-nerve fibers of known characteristic frequency," J Acoust Soc Am, Apr. 1982, 72(5):1441-1449.
Liu et al., "Mitochondrial morphogenesis, dendrite development, and synapse formation in cerebellum require both Bcl-w and the glutamate receptor delta2," PLoS Genet, 2008, 4(6):e1000097.
Lossi et al., "Posttranslational regulation of BCL2 levels in cerebellar granule cells: A mechanism of neuronal survival," Dev. Neurobiol., 2009, 69(13):855-870.
Lowery et al., "Whitesnake/sfpq is required for cell survival and neuronal development in the zebrafish," Dev. Dyn., 2007, 236(5):1347-1357.
Mak et al., "Differential and overlapping expression pattern of SOX2 and SOX9 in inner ear development," Gene Expression Patterns, Sep. 2009, 9(6):444-453.
Malik et al., "Chemotherapy-Induced Peripheral Neuropathy," Current Pain and Headache Reports, Jun. 2008, 12(3):165-174.
Mao et al., "Characterization and subcellular targeting of GCaMP-type genetically-encoded calcium indicators," PLoS One, 2008, 3(3):e1796.

McDonnell et al., "Importance of the Bcl-2 family in cell death regulation," Experientia, Oct. 1996, 52(10-11):1008-1017.
Middleton et al., "Reciprocal developmental changes in the roles of Bcl-w and Bcl-x(L) in regulating sensory neuron survival," Development, Jan. 2001, 128(3):447-457.
Miltenburg et al., "Chemotherapy-induced neuropathy: A comprehensive survey," Cancer Treat Rev., Aug. 2014, 40(7):872-882.
Mincheva-Tasheva et al., "Apoptotic cell death and altered calcium homeostasis caused by frataxin depletion in dorsal root ganglia neurons can be prevented by BH4 domain of Bcl-xL protein," Human Molecular Genetics, Nov. 2013, 23(7):1829-1841.
Minichiello et al., "Differential effects of combined trk receptor mutations on dorsal root ganglion and inner ear sensory neurons," Development, Sep. 1995, 121(12):4067-4075.
Monaco et al. "The BH4 domain of anti-apoptotic Bcl-XL, but not that of the related Bcl-2, limits the voltage-dependent anion channel 1 (VDAC1)-mediated transfer of pro-apoptotic Ca2+ signals to mitochondria," J. Biol. Chem. Apr. 2015, 290(14):9150-9161.
Morsli et al., "Development of the Mouse Inner Ear and Origin of Its Sensory Organs," J Neurosci, May 1, 1998, 18(9):3327-3335.
Nagy et al., "Apoptosis-Related Protein Expression in the Hippocampus in Alzheimer's Disease," Neurobiol Aging, Dec. 1997, 18(6):565-571.
Nakata et al., "Morphological evidence of the inhibitory effect of taxol on the fast axonal transport," Neuroscience Research, Aug. 1999, 35(2):113-122.
Nayagam et al., "The spiral ganglion: Connecting the peripheral and central auditory systems," Hearing Research, Aug. 2011, 278(1-2):2-20.
Nechushtan et al., "Conformation of the Bax C-terminus regulates subcellular location and cell death," EMBO J. 18(9):2330-2341 (1999).
Nennesmo et al., "Effects of intraneural injection of taxol on retrograde axonal transport and morphology of corresponding nerve cell bodies," Virchows Arch B Cell Pathol Incl Mol Pathol, Nov. 1988, 55(1):241-246.
Ng et al., "Revealing the way of self-complementary dimerization for a shape-persistent macrocycle using density functional theory calculations," J. Phys. Chem. B. 111(50):13886-93 (2007).
Nikolaev et al., "APP binds DR6 to trigger axon pruning and neuron death via distinct caspases," Nature, Feb. 2009, 457:981-989.
Oakes et al., "Proapoptotic BAX and BAK regulate the type 1 inositol trisphosphate receptor and calcium leak from the endoplasmic reticulum," Proceedings of the National Academy of Sciences of the United States of America, Jan. 2005, 102(1): 105-110.
Osterloh et al., dSarm/Sarm1 is required for activation of an injury-induced axon death pathway, Science, Jul. 2012, 337(6093):481-484.
Pachman et al., "Chemotherapy-Induced Peripheral Neuropathy: Prevention and Treatment," Clinical Pharmacology & Therapeutics, Aug. 2011, 90(3):377-387.
Packham et al., "Mutation of BCL-2 Family Proteins in Cancer," Apoptosis, Dec. 1998. 3(2):7582.
Parys et al., "The IP3 receptor as a hub for Bcl-2 family proteins in cell death control and beyond;" Sci. Signal, 2014, 7(312):pe4.
Pazya et al., "Preparation and maintenance of dorsal root ganglia neurons in compartmented cultures," J. Vis. Exp., Oct. 2008, (20)e951.
PCT International Search and Written Opinion in International Appln. No. PCT/US2017/048582, dated May 16, 2018, 18 pages.
Pease et al., "Paclitaxel reduces axonal Bclw to initiate IP3R1-dependent axon degeneration," Neuron, Oct. 2017, 96(2): 373-386.
Pease-Raissi et al., "Paclitaxel Reduces Axonal Bclw to Initiate IP3R1-Dependent Axon Degeneration," Neuron, Oct. 2017, 96(2):373-386.
Pena et al., "Bcl-xL and Bcl-2 expression in squamous cell carcinoma of the head and neck," Cancer, Jan. 1999, 85(1): 164-170.
Petros et al., "Solution structure of the antiapoptotic protein bcl-2," Proc. Natl. Acad. Sci. U.S.A. 98(6):3012-3017 (2001).
Pfannenstiel et al., "Bcl-2 Gene Therapy Prevents Aminoglycoside-Induced Degeneration of Auditory and Vestibular Hair Cells," Audiol Neurotol., Jan. 2009, 14(4):254-266.

(56) References Cited

OTHER PUBLICATIONS

Print et al., "Apoptosis regulator Bcl-w is essential for spermatogenesis but appears otherwise redundant," Proceedings of the National Academy of Sciences of the United States of America, Oct. 1998, 95(21):12424-12431.

Pritchard et al., "Bcl-w is an important determinant of damage-induced apoptosis in epithelia of small and large intestine," Oncogene, Aug. 2000, 19(34):3955-3959.

Raft et al., "Suppression of neural fate and control of inner ear morphogenesis by Tbx1," Development, Mar. 2004, 131(8):1801-1812.

Ramekers et al., "Neurotrophins and their role in the cochlea," Hearing Research, Jun. 2012, 288(1-2):19-33.

Ranger et al., "Mouse models of cell death," Nat Genet, 2001, 28(2):113-118.

Rong et al., "The BH4 domain of Bcl-2 inhibits ER calcium release and apoptosis by binding the regulatory and coupling domain of the IP3 receptor," Proceedings of the National Academy of Sciences of the United States of America, Aug. 2009, 106(34):14397-14402.

Rosenbluth et al., "The Fine Structure Of Acoustic Ganglia In The Rat," J Cell Biol, Feb. 1962, 12(2):329-359.

Ross et al., "BCLW mediates survival of postmitotic Sertoli cells by regulating BAX activity," Dev. Biol., 2001, 239(2):295-308.

Ross et al., "Testicular degeneration in Bclw-deficient mice," Nat Genet., Mar. 1998, 18(3):251-256.

Rybak et al., "siRNA-mediated knock-down of NOX3: therapy for hearing loss?" Cellular and Molecular Life Sciences, Jul. 2012, 69(14): 2429-2434.

Schacht et al., "Cisplatin and Aminoglycoside Antibiotics: Hearing Loss and Its Prevention," Anatomical Record, Oct. 2012, 295(11):1837-1850.

Schafmiester et al., "An All-Hydrocafbon Cross-Linking System for Enhancing the Helicity and Metabolic Stability of Peptides?" J. Am. Chem. Soc. 122:5891-5892, 2000.

Schlaepfer et al., "Effects of calcium ion concentration on the degeneration of amputated axons in tissue culture," The Journal of cell biology, Nov. 1973, 59:456-470.

Schoenmann et al., "Axonal Degeneration Is Regulated by the Apoptotic Machinery or a NAD+-Sensitive Pathway in Insects and Mammals," Journal of Neuroscience, 2010, 30(18): 6375-6386.

Sedlak et al., "Multiple Bcl-2 family members demonstrate selective dimerizations with Bax," Proc. Natl. Acad. Sci. U.S.A. 92(17):7834-7838 (1995).

Shimizu et al., "BH4 domain of antiapoptotic Bcl-2 family members closes voltage-dependent anion channel and inhibits apoptotic mitochondrial changes and cell death," Proceedings of the National Academy of Sciences of the United States of America, Mar. 2000, 97:3100-3105.

Silos-Santiago et al., "Severe Sensory Deficits but Normal CNS Development in Newborn Mice Lacking TrkB and TrkC Tyrosine Protein Kinase Receptors," Eur J Neurosci, Oct. 1997, 9(10):2045-2056.

Simon et al., "A Caspase Cascade Regulating Developmental Axon Degeneration," Journal of Neuroscience, 2012, 32(49):17540-17553.

Simon et al., "Axon Degeneration Gated by Retrograde Activation of Somatic Pro-apoptotic Signaling," Cell, Feb. 2016, 164:1031-1045.

Spoendlin et al., "Degeneration behaviour of the cochlear nerve," Arch Klin Exp Ohren Nasen Kehlkopfheilkd, 1971, 200(4):275-291.

Spoendlin et al., "Differentiation of Cochlear Afferent Neurons," Acta Otolaryngol, 1981, 91(1-6):451-456.

Stirling et al., "Axoplasmic reticulum Ca(2+) release causes secondary degeneration of spinal axons," Ann. Neurol., 2014, 75(2):220-229.

Stubblefield et al., "A prospective surveillance model for physical rehabilitation of women with breast cancer: chemotherapy-induced peripheral neuropathy," Cancer, 2012, 118(S8 Suppl A):2250-60.

Sugioka et al., "BH4-domain peptide from Bcl-xL exerts anti-apoptotic activity in vivo," Oncogene, 2003, 22:8432-8440.

Summers et al., "Mitochondrial dysfunction induces Sarm1-dependent cell death in sensory neurons," J. Neurosci., Jul. 2014, 34(28):9338-9350.

Sury et al., "Quantitative proteomics reveals dynamic interaction of c-Jun N-terminal kinase (JNK) with RNA transport granule proteins splicing factor proline- and glutamine-rich (Sfpq) and non—POU domain-containing octamer-binding protein (Nono) during neuronal differentiation," Mol Cell Proteomics, Jan. 2015, 14(1): 50-65.

Suzuki et al., "Structure of Bax: Coregulation of Dimer Formation and Intracellular Localization," Cell 103:645-654 (2000).

Taagepera et al., "The MPM-2 antibody inhibits mitogen-activated protein kinase activity by binding to an epitope containing phosphothreonine-183," Molecular Biology of the Cell, 1994, 5(11):1243-1251.

Tadros et al., "Apoptosis-related genes change their expression with age and hearing loss in the mouse cochlea," Apoptosis, 2008, 13(11):1303-1321.

Tait et al., "Mitochondria and cell death: outer membrane permeabilization and beyond" Nat. Rev. Mol. Cell Biol., 2010, 11(9):621-632.

Tang et al., "Expression of apoptosis regulators in cutaneous malignant melanoma," Clin Cancer Res, 1998, 4(8):1865-1871.

Theiss et al., "Taxol impairs anterograde axonal transport of microinjected horseradish peroxidase in dorsal root ganglia neurons in vitro," Cell and Tissue Research, 2000, 299:213-224.

ThermoFischer, Peptide Design, Posted online 2011, 8 pages.

Thomsen et al., "The ultrastructure of the spiral ganglion in the guinea pig," Acta Otolaryngol, 1967, 63(224):442-448.

Unsain et al., "XIAP regulates caspase activity in degenerating axons," Cell Reports, 2013, 4(4):751-763.

Usoskin et al., "Unbiased classification of sensory neuron types by large-scale single-cell RNA sequencing," Nat Neurosci, Nov. 2014, 18(1):145-153.

Vervliet et al., "Bcl-2 and FKBP12 bind to IP3 and ryanodine receptors at overlapping sites: the complexity of protein-protein interactions for channel regulation," Biochem. Soc. Trans., Jun. 2015, 43(3):396-404.

Vohra et al., "Amyloid precursor protein cleavage-dependent and -independent axonal degeneration programs share a common nicotinamide mononucleotide adenylyltransferase 1-sensitive pathway," J Neurosci, 2010, 30(41):13729-13738.

Wainger et al., "Modeling pain in vitro using nociceptor neurons reprogrammed from fibroblasts," Nature neuroscience, Nov. 2014, 18(1):17-24.

Walden et al., "Analytical procedures for quantification of peptides in pharmaceutical research by liquid chromatography-mass spectrometry," Analytical Bioanalytical Chemistry 378($):883-897 (2004).

Walensky et al., "Hydrocarbon-stapled peptides: principles, practice, and progress," Journal of Medicinal Chemistry, Feb. 2014, 57(15):6275-6288.

Walensky et al., "A stapled BID BH3 helix directly binds and activates BAX," Mol. Cell 24(2):199-210 (2006).

Walensky et al., "Activation of Apoptosis in Vivo by a Hydrocarbon-Stapled BH3 Helix," Science 305:1466-1470 (2004).

Wales et al. "High-speed and high-resolution UPLC separation at zero degrees Celsius," Anal. Chem. 80(17):6815-6820 (2008).

Wang et al., "Axon degeneration: molecular mechanisms of a self-destruction pathway," Journal of Cell Biology, 2012, 196(1):7-18.

Wang et al., "Calpain inhibition protects against Taxol-induced sensory neuropathy," Brain: a journal of neurology, 2004, 127(3):671-679.

Wang et al., "Design and bioinformatics analysis of genome-wide CLIP experiments," Nucleic Acids Res, May 2015, 43(11):5263-5274.

Wang et al., "WldS mice are resistant to paclitaxel (taxol) neuropathy," Annals of Neurology, 2002, 52:442-447.

Wilen, et al. "Strategies in Optical Resolutions," Tetrahedron 33:2725 (1977).

(56) References Cited

OTHER PUBLICATIONS

Williams et al., "Asymmetric synthesis of monosubstituted and .alpha.,.alpha.-disubstituted .alpha.-amino acids via diastereoselective glycine enolate alkylations," J. Am. Chem. Soc. 113(24):9276-9286 (1991).
Williams et al., "Efficient asymmetric synthesis of N-tert-butoxycarbonyl α-aminoacids using 4-tert-butoxycarbonyl-5,6-diphenylmorpholin-2-one: (r)-(N-tert-butoxycarbonyl)allylglycine," Org. Synth. 80:31-37 (2003).
Willis et al., "Differential transport and local translation of cytoskeletal, injury-response, and neurodegeneration protein mRNAs in axons," Journal of Neuroscience. 2005, 25(4): 778-791.
Willis et al., "Extracellular stimuli specifically regulate localized levels of individual neuronal mRNAs," Journal of Cell Biology, 2007, 178(6):965-980.
Wolter et al., "Movement of Bax from the cytosol to mitochondria during apoptosis," J. Cell Biol. 139(5):1281-1292 (1997).
www.nidcd.nih.gov [online], "Quick Statistics About Hearing," Dec. 2016, retrieved on Jun. 18, 2019, retrieved from URL http://www.nidcd.nih.gov/health/statistics/Pages/quick.aspx, 1 page.
Yaffe et al., "Sequence-specific and phosphorylation-dependent proline isomerization: a potential mitotic regulatory mechanism," Science, 1997, 278(5345):1957-1960.
Yang et al., "Compartmentalized microfluidic culture platform to study mechanism of paclitaxel-induced axonal degeneration," Experimental Neurology, 2009, 218:124-128.
Yang et al., "Pathological axonal death through a MAPK cascade that triggers a local energy deficit," Cell, Jan. 2015, 160(1-2):161-1762.
Yang et al., "Regulation of axon degeneration after injury and in development by the endogenous calpain inhibitor calpastatin," Neuron, 2013, 80(5):1175—89.
Yang et al., "Calculation of protein conformation from circular dichroism," Methods Enzymol. 130:208 (1986).
Yano et al., "RNA-binding protein research with transcriptome-wide technologies in neural development," Cell Tissue Res, Jun. 2014, 359(1):135-144.
Yao et al., "An essential role for beta-actin mRNA localization and translation in Ca2+-dependent growth cone guidance," Nature Neuroscience, 2006, 9(10):1265-1273.
Yarosh et al., "PSF: nuclear busy-body or nuclear facilitator?," WIREs RNA, Jul. 2015, 6(4):351-367.
Yilmaz et al., "Sensory neuron subpopulation-specific dysregulation of intracellular calcium in a rat model of chemotherapy-induced peripheral neuropathy," Neuroscience, Aug. 2015, 300:210-218.
Youle et al., "The BCL-2 protein family: opposing activities that mediate cell death," Nature Reviews Mol. Cell Biol 9:47-59 (2008).
Yu et al., "Neuroscience, dSarm-ing axon degeneration," Science, 2012, 337(6093):418-419.
Zhang et al., "A robust error model for iTRAQ quantification reveals divergent signaling between oncogenic FLT3 mutants in acute myeloid leukemia," Mol Cell Proteomics, 2010, 9(5):780-790.
Zhang et al., "Neurotrophin regulation of beta-actin mRNA and protein localization within growth cones," Journal of Cell Biology, 1999, 147(1):59-70.
Zhang et al., "Neurotrophin-induced transport of a beta-actin mRNP complex increases beta-actin levels and stimulates growth cone motility," Neuron, Aug. 2001, 31(2):261-275.

Zou et al., "Eyal and Six1 are essential for early steps of sensory neurogenesis in mammalian cranial placodes," Development, 2004, 131(22):5561-5572.
Courchesne et al., "Sensory Neuropathy Attributable to loss of Bcl-w," J Neurosci., Feb. 2011, 31(5):1624-1634.
PCT International Preliminary Report on Patentability in Appl. No. PCT/US2017/048582, dated Feb. 26, 2019, 10 pages.
U.S. Appl. No. 14/777,391, U.S. Pat. No. 10,106,590, filed Sep. 15, 2015, Walensky.
U.S. Appl. No. 16/119,974, filed Aug. 31, 2018, Walensky.
Bateman et al., "The Pfam protein families database," Nucl. Acids. Res., Jan. 2004, 32 (Database Issue):D138-141.
Cavaletti et al., "Chemotherapy-induced peripheral neurotoxicity," Nature Reviews Neurology, 2010, 6:657-666.
Chen et al., "Integrating Image-Based High-Content Screening with Mouse Models Identifies 5-Hydroxydecanoate as a Neuroprotective Drug for Paclitaxel-Induced Neuropathy," Molecular Cancer Therapeutics, 2015, 14(10):2206-2214.
Cosker et al., "The RNA-binding protein SFPQ orchestrates an RNA regulon to promote axon viability," Nat Neurosci., May 2016, 19(5):690-696.
EPO Communication for EP Application No. 14765369.5, dated Feb. 13, 2018, 4 pages.
Extended European Search Report in European Appln. No. 19179053.4, dated Oct. 17, 2019, 7 pages.
Gavathiotis et al., "BH3-triggered structural reorganization drives the activation of proapoptotic BAX," Molecular Cell, 2010, 40:481-492.
Hammond et al., "An examination of binding motifs associated with inter-particle interactions between facetted nano-crystals of acetyl-salicylic acid and ascorbic acid through the application of molecular grid-based search methods," J. Pharm, Sci., 2009, 98(12):4589-602.
PCT International Preliminary Report on Patentability for PCT/US2014/029318, dated Sep. 15, 2015, 8 pages.
PCT International Search Report for PCT/US2014/029318 dated Oct. 29, 2014, 6 pages.
Rautureau et al., "The restricted binding repertoire of Bcl-B leaves Bim as the universal BH3-only prosurvival Bcl-2 protein antagonist," Cell death & disease, Dec. 2012, 3(12):e443, 9 pages.
RCSB PDB-2XA0: Crystal structure of BCL-2 in complex with a BAX BH3 peptide, Nov. 24, 2010, retrieved on Oct. 13, 2021, retrieved from URL<https://www.rcsb.org/structure/2XA0>, 4 pages.
RCSB PDB-4CIM: Complex of a Bcl-w BH3 mutant with BH3 domain, Nov. 12, 2014, retrieved on Oct. 13, 2021, retrieved from URL<https://www.rcsb.org/structure/4CIM>, 5 pages.
RCSB PDB-4QVE: Crystal structure of Bcl-xL in complex with BID BH3 domain, Jun. 10, 2015, retrieved on Oct. 13, 2021, retrieved from URL<https://www.rcsb.org/structure/4QVE>, 5 pages.
Extended European Search Report for EP App. No. 14765369.5, dated Sep. 26, 2016, 6 pages.
Chipuk et al., "The BCL-2 family reunion," Molecular cell, Feb. 12, 2010, 37(3):299-310.
U.S. Appl. No. 14/777,391, 2016/0031959, U.S. Pat. No. 10,106,590, filed Sep. 15, 2015, Walensky.
U.S. Appl. No. 16/119,974, 2019/0092822, U.S. Pat. No. 11,046,739, filed Aug. 31, 2018, Walensky.
U.S. Appl. No. 17/232,678, filed Apr. 16, 2021, Walensky.
Okamoto et al., "Stabilizing the pro-apoptotic BimBH3 helix (BimSAHB) does not necessarily enhance affinity or biological activity," ACS chemical biology, Feb. 15, 2013, 8(2):297-302.

* cited by examiner

Graphical Abstract

Figure 9
A
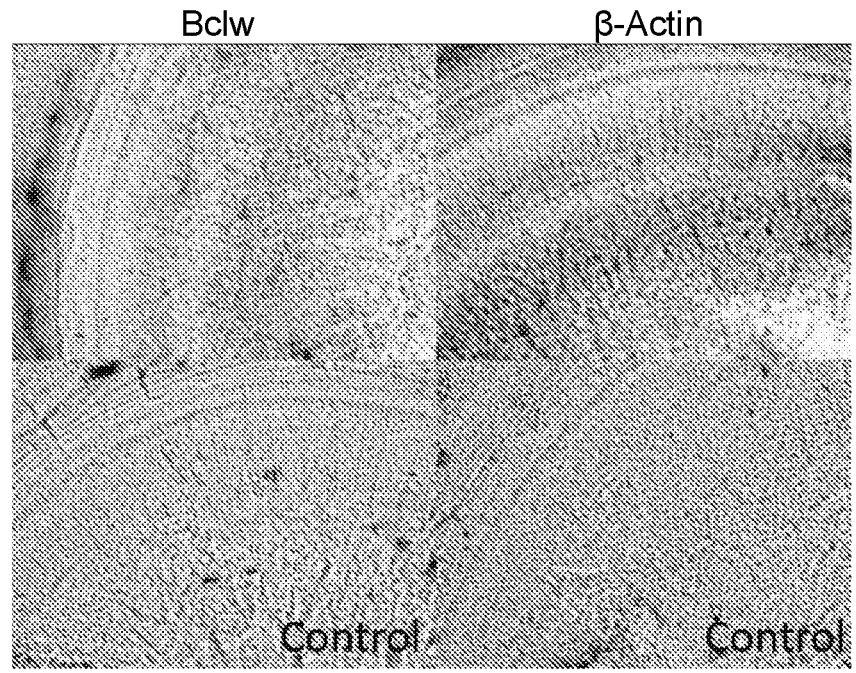
B
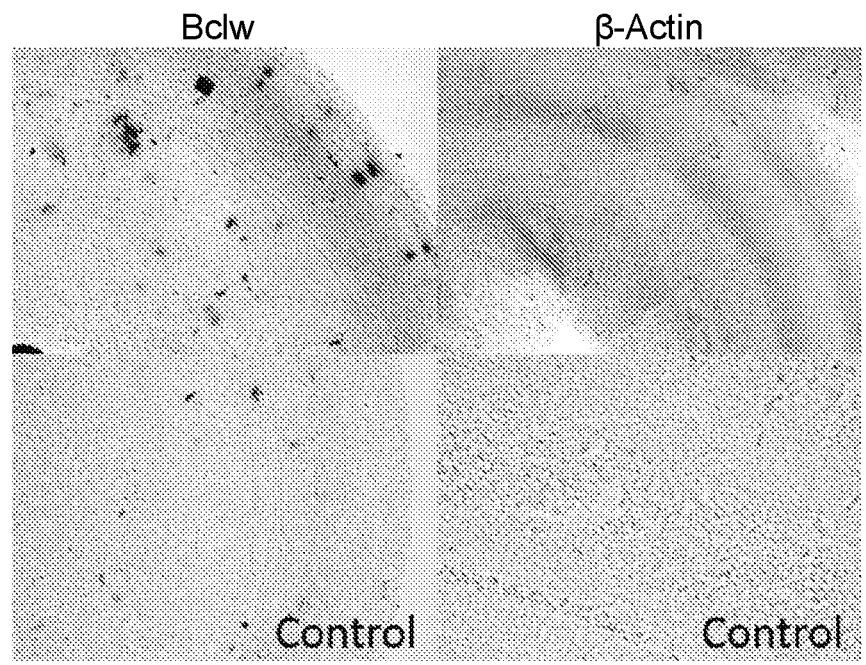

BCL-W POLYPEPTIDES AND MIMETICS FOR TREATING OR PREVENTING CHEMOTHERAPY-INDUCED PERIPHERAL NEUROPATHY AND HEARING LOSS

CROSS-REFERENCE TO RELATED APPLICATIONS

This application is a national stage of PCT/US2017/048582, filed Aug. 25, 2017, which claims the benefit of priority of U.S. Provisional Appl. No. 62/380,048, filed Aug. 26, 2016, the content of each of which is incorporated by reference herein in its entirety.

STATEMENT OF FEDERALLY SPONSORED RESEARCH

This invention was made with government support under grant numbers CA205255, AG000222, NS050674, and DC009223 awarded by The National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Nov. 4, 2021, is named Sequence_Listing_00530-0330US1.txt and is 39,511 bytes in size.

BACKGROUND

Axons that span long distances enable rapid communication within a neural circuit, but they are particularly vulnerable to injury and degeneration. Therefore, axonal degeneration impairs circuit functionality and is a prominent component of multiple neurologic disorders. Many chemotherapeutic drugs required to treat cancers can injure long-range axons (e.g., peripheral sensory or motor neuron axons), causing chemotherapy-induced peripheral neuropathy (CIPN) with impaired tactile sensation and persistent pain. Currently, the molecular mechanisms of CIPN are not understood, and there are no available treatments. There is an unmet need to provide compositions and methods for treating or preventing CIPN.

The ability to sense, respond to, and perceive music, warning cues, language, and other environmental stimuli depends on the auditory nervous system. The human sense of hearing is made possible by the conversion of sound stimuli into patterns of neural activity that can be integrated with other sensory information to guide behavior, intraspecies communication, and other critical functions. This remarkably rapid processing, which can occur in the space of 10 microseconds, relies on hair cells and their proper innervation by precisely wired spiral ganglion neurons within the cochlea of the inner ear. Successful transmission of the intensity, frequency, and timing of stimuli from hair cells to the brain is contingent on the proper assembly of these auditory circuits during development.

Through precisely organized circuits within the inner ear, sensory information represented by specific displacements of the inner and outer hair cells along the basilar membrane is converted into electrical signals that propagate along the spiral ganglia. Peripheral spiral ganglion axons transmit acoustic information from the hair cells to central projections within the eighth (VIIIth) nerve which innervates the brainstem at the anteroventral cochlear nucleus, the posteroventral cochlear nucleus, and the dorsal cochlear nucleus. Integrating centers within the superior olivary complex and inferior colliculus of the midbrain allow organisms to localize sources in space and process complex features such as the temporal and harmonic properties of speech and music. As spiral ganglion neurons form appropriate connections to provide the critical bridge from the inner ear to the central nervous system, understanding how these neurons initiate their assembly and maintain their processes over time is critical to efforts aimed at producing therapies to treat defects in the auditory nervous system.

SUMMARY

This disclosure relates, in part, to methods of treating or preventing chemotherapy-induced peripheral neuropathy or hearing loss using bclw protein, a BH4 domain-containing fragment thereof, or a bclw mimetic. Also disclosed are exemplary bclw mimetics that can be used in the methods described herein.

In a first aspect, the disclosure features a method of treating or preventing chemotherapy-induced peripheral neuropathy (CIPN) in a human subject in need thereof. In one instance, the method involves administering a therapeutically effective amount of a bclw protein or a BH4 domain containing fragment thereof. In another instance, the method involves administering a polypeptide comprising an amino acid sequence that is at least 70%, at least 75%, at least 80%, at least 85%, at least 90%, at least 95%, at least 96%, at least 97%, at least 98% or 100% identical to the amino acid sequence of the BH4 domain of bclw. In another instance, the method involves administering a polypeptide comprising an amino acid sequence that is identical to the amino acid sequence of the BH4 domain of bclw except for between 1 to 10, 1 to 9, 1 to 8, 1 to 7, 1 to 6, 1 to 5, 1 to 4, 1 to 3, 1 to 2, or 1 amino acid substitution, deletion, or insertion. The amino acid substitution may be conservative or non-conservative. In some cases, the substitutions are on the non-interacting face of the BH4 helix. In some cases, the substitutions are on both the interacting and non-interacting faces of the BH4 helix. The interacting/non-interacting face refers to the face of the helix involved in interacting with IP3R and/or Bax. In yet another instance, the method involves administering a bclw mimetic to the human subject.

In certain embodiments, the bclw protein or the BH4 domain containing fragment thereof comprises or consists of one of SEQ ID NOs.: 2, 3, 46, or 47, or an internally cross-linked variant thereof (e.g., wherein 2 amino acids are replaced by two olefinic side chain containing non-natural amino acids that can form a hydrocarbon staple).

In certain embodiments, the bclw mimetic is an internally cross-linked (e.g., stapled, stitched, or a combination thereof) polypeptide comprising the BH4 domain of bclw. In specific embodiments, the internally cross-linked bclw polypeptide is selected from the group consisting of the amino acid sequence set forth in SEQ ID NOs: 4-32, 50, and 51. In one embodiment, the internally cross-linked bclw polypeptide is ALVADFVGYKLRXKGYXSGA (SEQ ID NO: 50), wherein X is a non-natural amino acid with olefenic side chains. In some embodiments, the internally cross-linked bclw polypeptides has at least 10, 9, 8, 7, 6, 5, 4, 3, 2, or 1 amino acid substitutions relative to the amino acid sequence set forth in SEQ ID NOs: 4-32, 50, and 51. The amino acid substitutions may be conservative substitutions. In certain embodiments, the human subject has, or is at risk of developing, peripheral neuropathy following treatment with a chemotherapeutic agent. In some embodiments, the chemotherapeutic agent is a microtubule-targeting agent. In certain embodiments, the microtubule-targeting agent is a taxane (e.g., paclitaxel). In certain embodiments, the microtubule-targeting agent is vinblastine, vincristine, vindesine, vinorelbine, vinflunine, docetaxel, discodermolide, eleutherobin, sarcodictyin, epothilone, colchicine, combretastatin, 2-methoxyestradiol, or noscapine. In certain embodiments, the chemotherapeutic agent is an alkylating agent (e.g., oxaliplatin, lomustine, or carmustine). In certain embodiments, the chemotherapeutic agent is an arabinoside (e.g., cytarabine). In certain embodiments, the chemotherapeutic agent is a proteasome inhibitor, a PI3K inhibitor, or a Raf inhibitor. In some embodiments, the bclw mimetic, the BH4 domain containing fragment, and the polypeptide are each 8 to 100 (e.g., 8 to 40, 8 to 30, 8 to 50, 8 to 60) amino acids in length (e.g., 8, 9, 10, 11, 12, 13, 14, 15, 16, 17, 18, 19, 20, 21, 22, 23, 24, 25, 26, 27, 28, 29, 30, 32, 35, 40, 45, 50, 60, 70, 75, 80, 90, 100). In some embodiments, the bclw mimetic or the polypeptide is administered to the human subject topically. In certain embodiments, the method further involves administering metformin to the human subject.

In a second aspect, the disclosure provides a method of administering chemotherapy to a human subject in need thereof. The method involves administering an effective amount of a chemotherapeutic agent and a therapeutically effective amount of a bclw protein or a BH4 domain containing fragment thereof, a polypeptide comprising an amino acid sequence that is at least 70% identical to the amino acid sequence of the BH4 domain of bclw, or a bclw mimetic to the human subject.

In one embodiment, the internally cross-linked bclw polypeptide is selected from the group consisting of the amino acid sequence set forth in SEQ ID NOs: 4-32, 50, and 51. In one embodiment, the internally cross-linked bclw polypeptide is ALVADFVGYKLRXKGYXSGA (SEQ ID NO: 50), wherein X is a non-natural amino acid with olefenic side chains. In some embodiments, the internally cross-linked bclw polypeptides has at least 10, 9, 8, 7, 6, 5, 4, 3, 2, or 1 amino acid substitutions relative to the amino acid sequence set forth in SEQ ID NOs: 4-32, 50, and 51. The amino acid substitutions may be conservative substitutions. In certain cases, the serine in SEQ ID NO:50 or 51 is replaced with a cysteine or a norleucine. In certain embodiments, the polypeptide comprises an amino acid sequence that is at least 75%, at least 80%, at least 85%, at least 90%, at least 95%, at least 96%, at least 97%, at least 98% or 100% identical to the amino acid sequence of the BH4 domain of bclw. In some embodiments, the chemotherapeutic agent is a microtubule-targeting agent, an alkylating agent, an antimetabolite, a folic acid analogue, a spindle poison, a platinum compound, an epipodophyllotoxin, an antibiotic, an EGF-R inhibitor, an Eph-R inhibitor, a p38/JAK kinase inhibitor, a PI3K inhibitor, a MEK inhibitor, a MAPK inhibitor, a Trk inhibitor, a proteasome inhibitor, or a Raf inhibitor. In some embodiments, the microtubule-targeting agent is a taxane (e.g., paclitaxel). In some embodiments, the human subject has a hematological tumor. In certain instances the hematological tumor is selected from the group consisting of acute myeloid leukemia, chronic myeloid leukemia, Hodgkin lymphoma, non-Hodgkin lymphoma, multiple myeloma, acute lymphoblastic leukemia, and chronic lymphocytic leukemia. In some embodiments, the human subject has a solid tumor. In certain instances, the solid tumor is selected from the group consisting of breast cancer, ovarian cancer, and lung cancer. In certain embodiments, the chemotherapeutic agent and the bclw mimetic or the polypeptide are administered sequentially. In some instances, the bclw mimetic or the polypeptide is administered prior to the chemotherapeutic agent. In other instances, the chemotherapeutic agent is administered prior to the bclw mimetic or the polypeptide. In some embodiments, the chemotherapeutic agent and the bclw mimetic or the polypeptide are administered simultaneously. In certain instances, the method further involves administering metformin to the human subject.

In a third aspect, the disclosure relates to method of treating a human subject in need of treatment with chemotherapy. The method involves selecting a human subject that has one or more of: reduced levels of endogenous bclw in the axons of sensory neurons; reduced levels of EphA4 or Eph/5 receptors in sensory neurons; reduced expression of transporters; reduced expression of tubulin; or reduced expression of NGF, BDNF or NT3. The method further involves administering an effective amount of a bclw mimetic or a polypeptide comprising an amino acid sequence that is at least 70% identical to the amino acid sequence of the BH4 domain of bclw to the human subject.

In certain embodiments, the bclw mimetic is an internally cross-linked (e.g., stapled, stitched, or a combination thereof) polypeptide comprising the BH4 domain of bclw. In specific embodiments, the internally cross-linked bclw polypeptide is selected from the group consisting of the amino acid sequence set forth in SEQ ID NOs: 4-32, 50, and 51. In one embodiment, the internally cross-linked bclw polypeptide is ALVADFVGYKLRXKGYXSGA (SEQ ID NO: 50), wherein X is a non-natural amino acid with olefenic side chains. In some embodiments, the internally cross-linked bclw polypeptides has at least 10, 9, 8, 7, 6, 5, 4, 3, 2, or 1 amino acid substitutions relative to the amino acid sequence set forth in SEQ ID NOs: 4-32, 50, and 51. The amino acid substitutions may be conservative substitutions. In certain embodiments, the polypeptide comprises an amino acid sequence that is at least 75%, at least 80%, at least 85%, at least 90%, at least 95%, at least 96%, at least 97%, at least 98% or 100% identical to the amino acid sequence of the BH4 domain of bclw. In certain embodiments, the chemotherapy comprises a taxane (e.g., paclitaxel).

In another aspect, the disclosure features a method of treating or preventing hearing loss in a human subject in need thereof. The method involves administering to the human subject an effective amount of a bclw protein or a BH4 domain containing fragment thereof, a polypeptide comprising an amino acid sequence that is at least 70% identical to the amino acid sequence of the BH4 domain of bclw, or a bclw mimetic.

In certain embodiments, the bclw protein or the BH4 domain containing fragment thereof comprises or consists of one of SEQ ID NOs.: 2, 3, 46, or 47, or an internally cross-linked variant thereof (e.g., wherein 2 amino acids are replaced by two olefinic side chain containing non-natural amino acids that can form a hydrocarbon staple).

In certain embodiments, the bclw mimetic is an internally cross-linked (e.g., stapled, stitched, or a combination thereof) polypeptide comprising the BH4 domain of bclw. In specific embodiments, the internally cross-linked bclw polypeptide is selected from the group consisting of the amino acid sequence set forth in SEQ ID NOs: 4-32, 50, and 51. In one embodiment, the internally cross-linked bclw polypeptide is ALVADFVGYKLRXKGYXSGA (SEQ ID NO: 50), wherein X is a non-natural amino acid with olefenic side chains. In some embodiments, the internally cross-linked bclw polypeptides has at least 10, 9, 8, 7, 6, 5, 4, 3, 2, or 1 amino acid substitutions relative to the amino acid sequence set forth in SEQ ID NOs: 4-32, 50, and 51. The amino acid substitutions may be conservative substitutions. In some embodiments, the bclw mimetic, the BH4 domain containing fragment, and the polypeptide are each 8 to 100 (e.g., 8 to 40, 8 to 30, 8 to 50, 8 to 60) amino acids in length (e.g., 8, 9, 10, 11, 12, 13, 14, 15, 16, 17, 18, 19, 20, 21, 22, 23, 24, 25, 26, 27, 28, 29, 30, 32, 35, 40, 45, 50, 60, 70, 75, 80, 90, 100). In some embodiments, the bclw mimetic, the BH4 domain containing fragment, or the polypeptide is administered to the human subject by injection into the oval window. In some embodiments, the bclw mimetic, the BH4 domain containing fragment, or the polypeptide is administered to the human subject by topical application to the ear. In some embodiments, the bclw mimetic, the BH4 domain containing fragment, or the polypeptide is administered to a subject by direct delivery via the tympanic membrane. In certain instances, the administration involves the use of a virus (e.g., adenovirus, adeno-associated virus, lentivirus vectors) or using ear drops. In certain embodiments, the human subject has age-related hearing loss. In other embodiments, the human subject has noise-related hearing loss. In yet other embodiments, the human subject has chemotherapy-related hearing loss.

In another aspect the disclosure features a polypeptide comprising or consisting of an internally cross-linked polypeptide selected from the group consisting of SEQ ID NOs.: 4 to 30, 50 and 51. In certain embodiments, in instances where the N-terminal residue of the peptide is not an arginine, an arginine residue is added or substituted.

In yet another aspect, the disclosure provides a pharmaceutical composition comprising a pharmaceutically acceptable carrier and a polypeptide comprising or consisting of an internally cross-linked polypeptide selected from the group consisting of SEQ D NOs.: 4 to 32, 50 and 51. In certain embodiments, the pharmaceutical composition is formulated as ear drops.

In another aspect, the disclosure features a virus comprising a polypeptide comprising or consisting of an internally cross-linked polypeptide selected from the group consisting of SEQ ID NOs.: 4 to 30, 50 and 51; or a bclw protein; or a BH4 domain containing fragment thereof; or a polypeptide comprising an amino acid sequence that is at least 70% identical to the amino acid sequence of the BH4 domain of bclw. In certain embodiments, the virus is an adenovirus. In other embodiments, the virus is a an adeno-associate virus. In some embodiments, the virus is a lentivirus. Such viruses are useful in delivering the bclw peptide or protein to the subject.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the exemplary methods and materials are described below. All publications, patent applications, patents, and other references mentioned herein are incorporated by reference in their entirety. In case of conflict, the present application, including definitions, will control. The materials, methods, and examples are illustrative only and not intended to be limiting.

Other features and advantages of the invention will be apparent from the following detailed description and from the claims.

BRIEF DESCRIPTION OF THE DRAWINGS

FIG. 9A shows representative images of whole-mount in situ hybridization assays showing expression of Bclw mRNA in basal turns.

FIG. 9B shows representative images of whole-mount in situ hybridization assays showing lack of expression of Bclw mRNA in apical turns.

DETAILED DESCRIPTION

Figure 1:
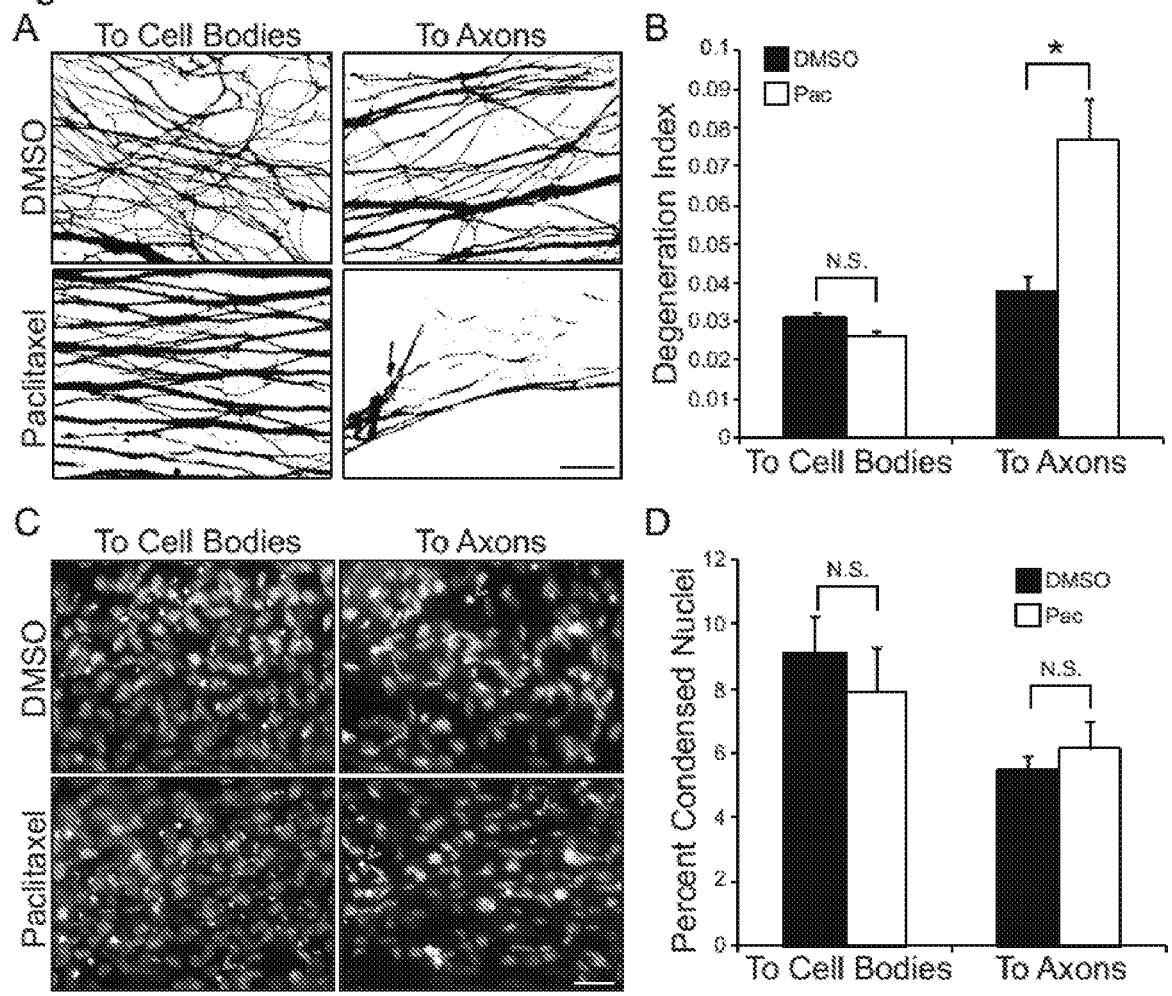
FIG. 1A shows binarized Tuj1 immunostaining of axons of E15 DRG neurons grown in compartmented cultures treated with DMSO vehicle control or 30 nM paclitaxel for 24 hours to cell body (left) or distal axon (right) compartments; Scale bar=40 µm.
FIG. 1B is a bar graph providing the quantification of axonal degeneration: ratio of area of fragmented axons to total axon area (degeneration index); *p<0.05 by Student's t-test, data represents mean+SEM, n=3.
FIG. 1C shows DAPI images of cell body compartments from FIG. 1A; Scale bar=10 µm, arrowheads indicate apoptotic nuclei.
FIG. 1D is a bar graph providing the quantification of apoptotic/total nuclei after addition of vehicle or paclitaxel to cell bodies or distal axons; *p<0.05 by Student's t-test, data represents mean+SEM, n=3.

The present disclosure is based, at least in part, on the finding that a BCL-2 family protein, bclw, a BH4 domain-containing fragment thereof, or bclw mimetics are useful for treating or preventing chemotherapy-induced peripheral neuropathy (CIPN). This disclosure features exemplary bclw mimetics that are internally cross-linked bclw polypeptides or modified bclw polypeptides that contain a sequence based on the BH4 domain of bclw. In addition, this disclosure provides methods for treating or preventing hearing loss (e.g., age-related, noise-induced, chemotherapy-induced). Also provided herein are pharmaceutical compositions and kits that contain at least one of these internally cross-linked bclw polypeptides and/or modified polypeptides, methods of using these internally cross-linked polypeptides and/or modified polypeptides to treat CIPN and hearing loss. Non-limiting aspects and embodiments of these methods are described herein. Any of the aspects described below can be used in any combination in the methods described herein.

Bclw

Bclw, also known as Bcl-2-like protein 2 is a protein that in humans is encoded by the BCL2L2 gene. Bclw encodes a pro-survival (i.e., anti-apoptotic) member of the bcl-2 protein family and expression of this gene in cells has been shown to contribute to reduced cell apoptosis under cytotoxic conditions. The murine form of this gene has been shown to play a role in the survival of NGF- and BDNF-dependent neurons.

The amino acid sequence of human bclw is provided below (the BH4 domain is boldened):

```
                                                  (SEQ ID NO: 1)
  1  MATPASAPDT RALVADFVGY KLRQKGYVCG AGPGEGPAAD

PLHQAMPAAG DEFETRFRRT

61  FSDLAAQLHV TPGSAQQRFT QVSDELFQGG PNWGRLVAFF

VFGAALCAES VNKEMEPLVG

121  QVQEWMVAYL ETRLADWIHS SGGWAEFTAL YGDGALEEAR

RLREGNWASV RTVLTGAMAL

181  GALVTVGAFF ASK
```

This disclosure features the use of the bclw protein in the methods described herein. The bclw protein that is used may be at least 65%, 70%, 75%, 80%, 85%, 87%, 90%, 91%, 92%, 93%, 94%, 95%, 96%, 97%, 98%, 99%, or 100% identical to SEQ ID NO: 1. These bclw proteins include the BH4 domain or a functional variant thereof methods for determining percent identity between amino acid sequences are known in the art. For example, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 60%, 70%, 80%, 90, or 100% of the length of the reference sequence. The amino acid residues at corresponding amino acid positions are then compared. When a position in the first sequence is occupied by the same amino acid residue as the corresponding position in the second sequence, then the molecules are identical at that position. The determination of percent identity between two amino acid sequences is accomplished using the BLAST 2.0 program. Sequence comparison is performed using an ungapped alignment and using the default parameters (Blossom 62 matrix, gap existence cost of 11, per residue gapped cost of 1, and a lambda ratio of 0.85). The mathematical algorithm used in BLAST programs is described in Altschul et al. (*Nucleic Acids Res.*, 25:3389-3402, 1997).

In some instances, the bclw protein used in the methods described herein are fragments of bclw that include the BH4 domain. These fragments can be, e.g., 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 125, or 150 amino acids in length. In certain instances, the fragments may be linked to a half-life extending moiety (e.g., polyethylene glycol, human serum albumin, an XTEN).

BH4 Domain

All proteins belonging to the Bcl-2 family contain either a BH1, BH2, BH3, or BH4 domain. The Bcl-2 family proteins are classified as multidomain anti-apoptotic, multidomain pro-apoptotic, or BH3-only pro-apoptotic proteins. All anti-apoptotic proteins contain BH1 and BH2 domains, and some of them contain an additional N-terminal BH4 domain (e.g., Bcl-2, Bcl-x(L), Bcl-w), which is not seen in pro-apoptotic proteins, except for Bcl-x(S). All pro-apoptotic proteins, except for Bad, and some anti-apoptotic proteins, such as Bcl-2 or Bcl-x(L), contain a BH3 domain that is necessary for dimerization with other proteins of Bcl-2 family and crucial for their killing activity; some of them also contain BH1 and BH2 domains (e.g., Bax, Bak).

The BH4 domain of bclw has the amino acid sequence: DTRALVADFVGYKLRQKGYVCGA (SEQ ID NO:2). In certain instances, the methods employ a bclw polypeptide comprising or consisting of the amino acid sequence: RALVADFVGYKLRQKGYVCGA (SEQ ID NO:3). In some instances, the methods employ a bclw polypeptide comprising or consisting of the amino acid sequence: ALVADFVGYKLRQKGYVCGA (SEQ ID NO:46). In some instances, the methods employ a bclw polypeptide comprising the amino acid sequence: TRALVADFVGYKLRQK (SEQ ID NO:47).

In certain instances, the BH4 domain of bclw has an amino acid sequence that is at least 40%, 45%, 50%, 55%, 60%, 65%, 70%, 75%, 80%, 85%, 90%, 95% identical to the amino acid sequence of SEQ ID NO:2. In certain instances, the BH4 domain of bclw has an amino acid sequence that is at least 40%, 45%, 50%, 55%, 60%, 65%, 70%, 75%, 80%, 85%, 90%, 95% identical to the amino acid sequence of SEQ ID NO:3. In certain instances, the BH4 domain of bclw has an amino acid sequence that is at least 40%, 45%, 50%, 55%, 60%, 65%, 70%, 75%, 80%, 85%, 90%, 95% identical to the amino acid sequence of SEQ ID NO:46. In certain instances, the BH4 domain of bclw has an amino acid sequence that is at least 40%, 45%, 50%, 55%, 60%, 65%, 70%, 75%, 80%, 85%, 90%, 95% identical to the amino acid sequence of SEQ ID NO:47. In some cases the variability from SEQ ID NO:2, 3, 46, or 47 is on the non-interacting alpha-helical face of the BH4 domain (e.g., the domain that interacts with IP3R and/or Bax). In some cases, the variability from SEQ ID NO:2 is on both the interacting and the non-interacting alpha-helical face of the BH4 domain (e.g., the domain that interacts with IP3R and/or Bax).

An alignment of a region comprising the BH4 domains of Bcl-2 (SEQ ID NO:34), Bcl-x(L) (SEQ ID NO:35), Bcl-w (SEQ ID NO:36) are provided below:

| | Helix 1 | |
|---|---|---|
| BCL-2 | MAHAGRTGYDNREIVMKYTHYKLSQRGYEWDAGDVGAAPPGAAPAPGIFS | 50 |
| BCL-XL | -----MSQSNRELVVDFLSYKLSQKGYSWSQFSDVEENRTEAPEG---- | 40 |
| BCL-W | MATP-ASAPDTRALVADFVGYKLRQKGYVCGAGPGEGPAAD-------- | 40 |

In some instances, the methods described herein employ a polypeptide comprising the BH4 domain of bclw or a polypeptide variant thereof. For example, the polypeptide variant may comprise at least one, two, three, four, five, six, seven, eight, nine, ten, eleven, twelve, or thirteen amino acid substitutions relative to the amino acid sequence set forth in SEQ ID NOs:2, 3, 46, or 47. The substitutions can be on the non-interacting alpha-helical face of the BH4 domain (e.g., the domain that interacts with IP3R and/or Bax). In some cases, the substitutions in SEQ ID NO:2 are on both the interacting and the non-interacting alpha-helical face of the BH4 domain (e.g., the domain that interacts with IP3R and/or Bax). In certain instances, a cysteine residue in a BH4 domain of bclw is replaced with a serine. Thus, the disclosure includes amino acid sequences set forth in SEQ ID NOs:2, 3, 46, or 47 except that the cysteine residue in these sequences is replaced with a serine. In certain instances, a cysteine residue in a BH4 domain of bclw is replaced with a norleucine. Thus, the disclosure includes amino acid sequences set forth in SEQ ID NOs:2, 3, 46, or 47 except that the cysteine residue in these sequences is replaced with a norleucine.

In certain instances, the bclw polypeptide that is employed in the methods described herein is 5, 6, 7, 8, 9, 10, 11, 12, 13, 14, 15, 16, 17, 18, 19, 20, 21, 22, 23, 24, 25, 26, 27, 28, 29, or 30 amino acids in length. In certain instances, the bclw polypeptide that is employed in the methods described herein is 5 to 30, 6 to 30, 7 to 30, 8 to 30, 9 to 30, 10 to 30, 11 to 30, 12 to 30, 14 to 30, 15 to 30, 16 to 30, 17 to 30, 18 to 30, 19 to 30, or 20 to 30 amino acids in length.

Internally Cross-Linked Bclw Polypeptides

In some instances, the methods described herein employ a bclw mimetic. For example, the disclosure provides internally cross-linked polypeptides and/or modified polypeptides that contain a sequence based on a BH4 domain of the BCL-2 family protein, bclw, that include at least two modified amino acids joined by an internal (intramolecular) cross-link (or staple), wherein the at least two amino acids are separated by 2 to 6 amino acids (e.g., 2, 3, or 6 amino acids). Stabilized peptides herein include stapled and/or stitched peptides.

Amino acids are the building blocks of the peptides disclosed herein. The term "amino acid" refers to a molecule containing both an amino group and a carboxyl group. Amino acids include alpha-amino acids and beta-amino acids. Amino acids suitable for inclusion in the peptides disclosed herein include, without limitation, natural alpha-amino acids, such as D- and L-isomers of the 20 common naturally-occurring alpha-amino acids found in peptides (e.g., Ala (A), Arg (R), Asn (N), Cys (C), Asp (D), Gln (Q), Glu (E), Gly (G), His (H), Ile (I), Leu (L), Lys (K), Met (M), Phe (F), Pro (P), Ser (S), Thr (T), Trp (W), Tyr (Y), and Val (V)), unnatural (or non-natural) alpha-amino acids (including, but not limited to, α,α-disubstituted and N-alkylated amino acids), natural beta-amino acids (e.g., beta-alanine), and unnatural (or non-natural) beta-amino acids. Amino acids used in the construction of the internally cross-linked polypeptides and modified polypeptides of the present disclosure can be prepared by organic synthesis or obtained by other routes, such as, e.g., degradation of or isolation from a natural source.

There are many known unnatural (or non-natural) amino acids, any of which can be included in the internally cross-linked polypeptides and modified polypeptides of the present invention. Some non-limiting examples of unnatural amino acids are 4-hydroxyproline, desmosine, gamma-aminobutyric acid, beta-cyanoalanine, norvaline, 4-(E)-butenyl-4(R)-methyl-N-methyl-L-threonine, N-methyl-L-leucine, 1-amino-cyclopropanecarboxylic acid, 1-amino-2-phenyl-cyclopropanecarboxylic acid, 1-amino-cyclobutanecarboxylic acid, 4-amino-cyclopentenecarboxylic acid, 3-amino-cyclohexanecarboxylic acid, 4-piperidylacetic acid, 4-amino-1-methylpyrrole-2-carboxylic acid, 2,4-diaminobutyric acid, 2,3-diaminopropionic acid, 2,4-diaminobutyric acid, 2-aminoheptanedioic acid, 4-(aminomethyl)benzoic acid, 4-aminobenzoic acid, ortho-, meta-, and para-substituted phenylalanines (e.g., substituted with —C(=O)C$_6$H$_5$; —CF$_3$; —CN; -halo; —NO$_2$; CH$_3$), disubstituted phenylalanines, substituted tyrosines (e.g., further substituted with -Q=O)C$_6$H$_5$; —CF$_3$; —CN; -halo; —NO$_2$; CH$_3$), and statine. Additionally, amino acids can be derivatized to include amino acid residues that are, e.g., hydroxylated, phosphorylated, sulfonated, acylated, and glycosylated.

A "peptide" or "polypeptide" contains (includes) a polymer of amino acid residues linked together by peptide (amide) bonds. The term(s), as used herein, refer(s) to proteins, polypeptides, and peptides of any size, structure, or function. Typically, a peptide or polypeptide will be at least three amino acids long. A peptide or polypeptide can refer to an individual protein or a collection of proteins. In some instances, peptides can include only natural amino acids, although non-natural amino acids (i.e., compounds that do not occur in nature but that can be incorporated into a polypeptide chain) and/or amino acid analogs known in the art can alternatively be employed. Also, one or more of the amino acids in a peptide or polypeptide can be modified, e.g., by the addition of a chemical entity, e.g., a carbohydrate group, a hydroxyl group, a phosphate group, a farnesyl group, an isofarnesyl group, a fatty acid group, a linker for conjugation, functionalization, and/or other modification. A peptide or polypeptide can be a single molecule or can be a multi-molecular complex, e.g., a protein. A peptide or polypeptide can be a fragment of a naturally-occurring protein or peptide. A peptide or polypeptide can be naturally-occurring, recombinant, or synthetic, or any combination thereof. "Dipeptide" refers to two covalently linked amino acids.

Exemplary peptides that can be used to generate the internally cross-linked polypeptides described herein can include a sequence (e.g., at least 10, 11, 12, 13, 14, 15, 16, 17, 18, 19, 20, 21, 22, 23, 24, 25, 26, 27, 28, 29, or 30 amino acids, or between 10-30, 15-24, 15-25, 17-25, 15-22, 18-20, 18-22, 18-25, 19-22, 19-25, 20-22, 20-21, 20-22, 20-23, 20-24, 20-25, 20-26, 20-27, 20-28, 20-29, 20-30, 22-35, 22-40, or 22-50 amino acids) that is at least 70% (e.g., at least 75%, 80%, 85%, 90%, 95%, 96%, 97%, 98%, 99%, or 100%) identical to the BH4 domain of bclw e.g., that inherently possess or can be induced to have an alpha-helical secondary structure. Additional exemplary peptides that can be used to generate the internally cross-linked polypeptides described herein can contain one or more additional amino acids present in bclw that are N- and/or C-terminal to the conserved BH4 domain. Additional exemplary peptides that can be used to generate the internally cross-linked polypeptides described herein include a one, two, three, or four amino acid N-terminal and/or a one, two, three, or four amino acid C-terminal truncation of the sequence of any one of SEQ ID NOs: 4-32.

In some instances, the internally cross-linked polypeptides e.g. comprise, consist essentially of, or consist of an amino acid sequence selected from the group of RAL-VADFVGYKLRQKGYVCGA (SEQ ID NO:3) or ALVADFVGYKLRQKGYVCGA (SEQ ID NO:46), RAL-VADFVGYKLRQKGYV (SEQ ID NO:48), or ALVADFVGYKLRQKGYV (SEQ ID NO:49), wherein between 1, 2, 3, 4, 5, 6 amino acid substitutions (e.g., cysteine to serine, conservative amino acid substitutions) are made in the sequence of SEQ ID NO:3 or SEQ ID NO:46, and wherein: the side chains of two amino acids separated by two to six (inclusive)(e.g., 2, 3, or 6) amino acids are replaced by an internal staple; the side chains of three amino acids are replaced by internal staples and/or an internal stitch; the side chains of four amino acids are replaced by internal staples, internal stitches, or a combination of internal staples and stitches; or the side chains of at least four amino acids are replaced by internal staples, internal stitches, or a combination of internal staples and stitches. In certain cases, two amino acids in SEQ ID NO: 2, 3, or 46-49 are hydrocarbon stapled. In certain instances, three amino acids in SEQ ID NO: 2, 3, or 46-49 are stitched. In some instances, any two amino acids in SEQ ID NO: 2, 3, or 46-49 at positions [i] and [i+3], positions [i] and [i+4], or at positions [i] and [i+7] are replaced by a non-natural amino acid with olefenic side chains. For example, for [i] and [i+3], it could be two S5 pentenyl alanines, or one R-propenyl alanine and one S-pentenyl alanine; for [i] and [i+4] two S-pentenyl alanines may be used; for [i,] and [i+7] one S-pentenyl alanine and one R-octenyl alanine may be used, or one R-pentenyl alanine and one S-octenyl alanine may be used. Such peptides, upon ruthenium catalyzed olefin metathesis can yield "stapled" bclw peptides. In certain instances, the bclw stapled or stitched peptides can also has one, two, three, four, five, six, or seven amino acid substitutions relative to SEQ ID NO: 2, 3, or 46-49. In certain instances, the amino acid substitutions are conservative. For example, a positively charged amino acid can be replaced by R, K, or H; a negatively-charged amino acid can be replaced with D, N, E, or Q; a polar amino acid can be replaced with A, G, V, L, I, W, F, or Y; and serine, threonine or cysteine can be replaced by each other. It is to be understood that non-natural homologues of the amino acid could be substituted in place of the natural amino acid. In certain instances, the bclw stapled or stitched peptides can also has one, two, three, four, or five deletions relative to SEQ ID NO: 2, 3, or 46-49. In certain instances, the bclw stapled or stitched peptides have one, two, three, or four amino acid substitutions relative to SEQ ID NO: 2, 3, or 46-49 and also have one, two, or three deletions relative to SEQ ID NO:2, 3, or 46-49. Bclw peptides with these substitutions and/or deletions can be selected for use in the methods described herein based on their ability to, e.g., reduce or prevent axonal degeneration and/or bind to the endoplasmic reticulum calcium channel, IP$_3$R1. Methods for determining whether a peptide has these properties are, e.g., described in the Examples. In some cases, the internally stapled or stitched bclw polypeptide includes a targeting moiety or a moiety that facilitates cell entry (e.g., 2, 3, 4, 5, 6, 7, 8 or 9 contiguous Arg) at the amino or carboxy terminus.

A "conservative amino acid substitution" is an amino acid substitution that does not reduce (e.g., substantially reduce) binding of the internally cross-linked polypeptide or modified polypeptide to its target protein, e.g., BAX protein or endoplasmic reticulum calcium channel, IP$_3$R1, and can, in some circumstances, improve binding activity. Methods for detecting any reduction in binding can include comparing binding affinity following conservative amino acid substitution, wherein any amino acid substitution that reduces (e.g., substantially reduces) binding are not conservative amino acid substitutions. In some aspects, substantially reduced binding can include binding that is 10% or less, 20% or less, 30% or less, 40% or less, 50% or less, 60% or less, 70% or less, 80% or less, 90% or less, 95% or less, 98% or less, 99% or less, or 100% less than binding of the unsubstituted internally cross-linked polypeptide or modified polypeptide to its target protein, e.g., a BAX protein, or endoplasmic reticulum calcium channel, IP$_3$R1. Methods for assessing interaction between an internally cross-linked polypeptide or modified polypeptide and a target protein, e.g., a BAX protein or endoplasmic reticulum calcium channel, IP$_3$R1, are disclosed herein.

In some instances, a "conservative amino acid substitution" can include substitutions in which one amino acid residue is replaced with another amino acid residue having a similar side chain. Families of amino acid residues having similar side chains have been defined in the art. These families include amino acids with basic side chains (e.g., lysine, arginine, and histidine), acidic side chains (e.g., aspartic acid and glutamic acid), uncharged polar side chains (e.g., glycine, asparagine, glutamine, serine, threonine, tyrosine, and cysteine), nonpolar side chains (e.g., alanine, valine, leucine, isoleucine, proline, phenylalanine, methionine, and tryptophan), beta-branched side chains (e.g., threonine, valine, and isoleucine) and aromatic side chains (e.g., tyrosine, phenylalanine, tryptophan, and histidine).

Non-limiting exemplary internally cross-linked bclw peptides that can be used in the methods described herein include any one of:

```
XALVXDFVGYKLRQKGYV    (SEQ ID NO: 4)

RXLVAXFVGYKLRQKGYV    (SEQ ID NO: 5)

RAXVADXVGYKLRQKGYV    (SEQ ID NO: 6)

RALXADFXGYKLRQKGYV    (SEQ ID NO: 7)

RALVXDFVXYKLRQKGYV    (SEQ ID NO: 8)

RALVAXFVGXKLRQKGYV    (SEQ ID NO: 9)

RALVADXVGYXLRQKGYV    (SEQ ID NO: 10)

RALVADFXGYKXRQKGYV    (SEQ ID NO: 11)

RALVADFVXYKLXQKGYV    (SEQ ID NO: 12)

RALVADFVGXKLRXKGYV    (SEQ ID NO: 13)

RALVADFVGYXLRQXGYV    (SEQ ID NO: 14)

RALVADFVGYKXRQKXYV    (SEQ ID NO: 15)

RALVADFVGYKLXQKGXV    (SEQ ID NO: 16)

RALVADFVGYKLRXKGYX    (SEQ ID NO: 17)

RALVADFVGYKLRQXGYVX   (SEQ ID NO: 18)

8ALVADFXGYKLRQKGYV    (SEQ ID NO: 19)

R8LVADFVXYKLRQKGYV    (SEQ ID NO: 20)

RA8VADFVGXKLRQKGYV    (SEQ ID NO: 21)
```

```
RAL8ADFVGYXLRQKGYV                      (SEQ ID NO: 22)

RALV8DFVGYKXRQKGYV                      (SEQ ID NO: 23)

RALVA8FVGYKLXQKGYV                      (SEQ ID NO: 24)

RALVAD8VGYKLRXKGYV                      (SEQ ID NO: 25)

RALVADF8GYKLRQXGYV                      (SEQ ID NO: 26)

RALVADFV8YKLRQKXYV                      (SEQ ID NO: 27)

RALVADFVG8KLRQKGXV                      (SEQ ID NO: 28)

RALVADFVGY8LRQKGYX                      (SEQ ID NO: 29)

RALVADFVGYK8RQKGYVX;                    (SEQ ID NO: 30)

ALVADFVGYKLRXKGYXBGA;                   (SEQ ID NO: 31)

RALVADFVGYKLRXKGYXBGA;                  (SEQ ID NO: 32)

ALVADFVGYKLRXKGYXSGA;                   (SEQ ID NO: 50)

RALVADFVGYKLRXKGYXSGA;                  (SEQ ID NO: 51)

ALVADFVGYKLRXKGYXCGA;                   (SEQ ID NO: 52)
or

RALVADFVGYKLRXKGYXCGA,                  (SEQ ID NO: 53)
``` wherein X is S-pentenyl alanine; wherein "8" is R-octenyl alanine; and wherein "B" is norleucine.

In a different embodiment, each X in each sequence above (i.e., SEQ ID NOs.: 4-32 and 50-53) can be the same non-natural amino acid or different non-natural amino acid. In certain instances, "X" is one of (S)-2-(4-pentenyl)Ala-OH, (R)-2-(4-pentenyl)Ala-OH, (R)-2-(7-octenyl)Ala-OH, (S)-2-(7-octenyl)Ala-OH, 2-amino-2-(pent-4-enyl)hept-6-enoic acid, (R)-2-(2-propenyl)Ala-OH, or (S)-2-(2-propenyl)Ala-OH. In certain embodiments, if a sequence has two "X's" both X's are (S)-2-(4-pentenyl)Ala-OH. In certain embodiments, if a sequence has two "X's" both X's are (R)-2-(4-pentenyl)Ala-OH. In certain embodiments, if a sequence has two "X's" both X's are (R)-2-(7-octenyl)Ala-OH. In certain embodiments, if a sequence has two "X's" both X's are (S)-2-(7-octenyl)Ala-OH. In certain embodiments, if a sequence has two "X's" both X's are 2-amino-2-(pent-4-enyl)hept-6-enoic acid. In certain embodiments, if a sequence has two "X's" both X's are (R)-2-(2-propenyl)Ala-OH. In certain embodiments, if a sequence has two "X's" both X's are (R)-2-(2-propenyl)Ala-OH. In certain embodiments, if a sequence has two "X's" both X's are (S)-2-(2-propenyl)Ala-OH. In certain embodiments, if a sequence has two "X's" both X's are different non-natural amino acids and can, e.g., be selected from the group consisting of S)-2-(4-pentenyl)Ala-OH, (R)-2-(4-pentenyl)Ala-OH, (R)-2-(7-octenyl)Ala-OH, (S)-2-(7-octenyl)Ala-OH, 2-amino-2-(pent-4-enyl)hept-6-enoic acid, (R)-2-(2-propenyl)Ala-OH, and (S)-2-(2-propenyl)Ala-OH. In certain instances, if the two X's are separated by 3 amino acids, the two X's can be different non-natural residues, e.g., the first X is (R)-2-(2-propenyl)Ala-OH or (S)-2-(2-propenyl)Ala-OH and the second X is (S)-2-(2-propenyl)Ala-OH or (R)-2-(2-propenyl)Ala-OH. In certain instances, the "X's" that are in SEQ ID NOs.: 4-32 or 50-53, or inserted into SEQ ID NOs.: 2, 3, 46, 48, or 49 can be any residue/substance that permits formation of a staple and/or stitch. In other words, the staple and/or stitch does not need to be a hydrocarbon-staple and/or stitch. Methods of performing different types of stapling are well known in the art (see, e.g., Lactam stapling: Shepherd et al., *J. Am. Chem. Soc.*, 127: 2974-2983 (2005); Triazole stapling: Kawamoto et al., *J. Med. Chem.*, 55:1137-1146 (2011); UV-cycloaddition stapling: Madden et al., *Bioorg. Med. Chem. Lett.*, 21:1472-1475 (2011); Disulfide stapling: Jackson et al., *Am. Chem. Soc.*, 113:9391-9392 (1991); Oxime stapling: Haney et al., *Chem. Commun.*, 47:10915-10917 (2011); Thioether stapling: Brunel and Dawson, *Chem. Commun.*, 552-2554 (2005); Photoswitchable stapling: J. R. Kumita et al., *Proc. Natl. Acad. Sci. U.S.A.*, 97:3803-3808 (2000); Double-click stapling: Lau et al., *Chem. Sci.*, 5:1804-1809 (2014); Bis-lactam stapling: J. C. Phelan et al., *J. Am. Chem. Soc.*, 119:455-460 (1997); and Bis-arylation stapling: A. M. Spokoyny et al., *J. Am. Chem. Soc.*, 135:5946-5949 (2013)). In certain instances, the "X's" that are in SEQ ID NOs.: 4-32 or 50-53, or inserted into SEQ ID NOs.: 2, 3, 46, 48, or 49 can be any residue that permits formation of a hydrocarbon staple and/or stitch. In certain instances, the peptides with the sequences recited in SEQ ID NOs.: 4-32 or 50-53, or inserted into SEQ ID NOs.: 2, 3, 46, 48, or 49 are lactam stapled. In other instances, the peptides with the sequences recited in SEQ ID NOs.: 4-32 or 50-53, or inserted into SEQ ID NOs.: 2, 3, 46, 48, or 49 are triazole stapled. In other instances, the peptides with the sequences recited in SEQ ID NOs.: 4-32 or 50-53, or inserted into SEQ ID NOs.: 2, 3, 46, 48, or 49 are stapled using a UV-cycloaddition staple. In other instances, the peptides with the sequences recited in SEQ ID NOs.: 4-32 or 50-53, or inserted into SEQ ID NOs.: 2, 3, 46, 48, or 49 are disulfide stapled. In other instances, the peptides with the sequences recited in SEQ D NOs.: 4-32 or 50-53, or inserted into SEQ ID NOs.: 2, 3, 46, 48, or 49 are oxime stapled. In other instances, the peptides with the sequences recited in SEQ ID NOs.: 4-32 or 50-53, or inserted into SEQ ID NOs.: 2, 3, 46, 48, or 49 are thioether stapled. In other instances, the peptides with the sequences recited in SEQ ID NOs.: 4-32 or 50-53, or inserted into SEQ ID NOs.: 2, 3, 46, 48, or 49 comprise a photoswitchable staple. In other instances, the peptides with the sequences recited in SEQ ID NOs.: 4-32 or 50-53, or inserted into SEQ ID NOs.: 2, 3, 46, 48, or 49 are double-click stapled. In other instances, the peptides with the sequences recited in SEQ ID NOs.: 4-32 or 50-53, or inserted into SEQ ID NOs.: 2, 3, 46, 48, or 49 are bis-lactam stapled. In other instances, the peptides with the sequences recited in SEQ ID NOs.: 4-32 or 50-53, or inserted into SEQ ID NOs.: 2, 3, 46, 48, or 49 comprise a bis-arylation staple. In certain embodiments, the bclw internally cross-linked peptide comprises or consists of the amino acid sequence set forth in SEQ ID NO: 4-33, or a modified version (i.e., a sequence comprising 2 or more (e.g., 3, 4, 5, 6) non-natural olefinic side chain-containing amino acids that can form a hydrocarbon staple) of, an amino sequence set forth in any one of SEQ ID NOs.: 2, 3, 46, 48, or 49.

In some embodiments of any of the methods described herein, the bclw internally cross-linked peptide is 18 to 100 amino acids in length (e.g., between 18 and 90 amino acids in length, between 18 and 80 amino acids in length, between 18 and 70 amino acids in length, between 18 and 60 amino acids in length, between 18 and 50 amino acids in length, between 18 and 40 amino acids in length, between 18 and 30 amino acids in length, between 18 and 25 amino acids in length, between 20 and 40 amino acids in length, between 20 and 35 amino acids in length, between 20 and 30 amino acids in length, between 22 and 40 amino acids in length; between 22 and 35 amino acids in length, between 22 and 30 amino acids in length, between 25 and 40 amino acids in length, between 25 and 35 amino acids in length, or between 25 and 30 amino acids in length).

As disclosed above, internally cross-linked polypeptides or modified polypeptides herein include at least two modified amino acids that together form an internal (intramolecular) cross-link (or staple), wherein the at least two modified amino acids are separated by 2 (i.e., i, i+3), 3 (i.e., i, i+4), or 6 (i.e., i, i+7) amino acids. Additional exemplary relative positions of staple(s) and/or stitch(es) that can be introduced in any of the internally cross-linked polypeptides and modified polypeptides described herein are known in the art. See, e.g., US 2016/0031959 incorporated by reference in its entirety herein.

In the case of a cross-link between i and i+3 the cross-link can be a $C_7$ alkylene or alkenylene. In the case of a cross-link between i and i+4 the cross-link can be a $C_8$ alkylene or alkenylene. In the case of a cross-link between i and i+7 the cross-link can be a $C_{11}$, $C_{12}$, or $C_{13}$ alkylene or alkenylene. When the cross-link is an alkenylene, there can be one or more double bonds.

In the case of a cross-link between i and i+3 the cross-link can be a $C_6$, $C_7$, or $C_8$ alkyl or alkene (e.g., a $C_6$ alkene having a single double bond). In the case of a cross-link between i and i+4 the cross-link can be a $C_8$ alkyl or alkene. In the case of a cross-link between i and i+7 the cross-link can be a $C_{11}$, $C_{12}$, or $C_{13}$ alkyl or alkene (e.g., a $C_{11}$ alkene having a single double bond). When the cross-link is an alkene, there can be one or more double bonds.

"Peptide stapling" or "hydrocarbon stapling" is a term coined from a synthetic methodology, wherein two olefin-containing side-chains (e.g., cross-linkable side chains) present in a polypeptide chain are covalently joined (e.g., "stapled together") using a ring-closing metathesis (RCM) reaction to form a cross-linked ring (see, e.g., Blackwell et al., *J. Org. Chem.*, 66: 5291-5302, 2001; Angew et al., *Chem. Int. Ed.* 37:3281, 1994). As used herein, the term "peptide stapling" or "hydrocarbon stapling" includes the joining of two (e.g., at least one pair of) double bond-containing side-chains, triple bond-containing side-chains, or double bond-containing and triple bond-containing side chain, which can be present in a polypeptide chain, using any number of reaction conditions and/or catalysts to facilitate such a reaction, to provide a singly "stapled" polypeptide. The term "multiply stapled" polypeptides refers to those polypeptides containing more than one individual staple, and can contain two, three, or more independent staples of various spacings and compositions. The term "peptide stitching," as used herein, refers to multiple and tandem "stapling" events in a single polypeptide chain to provide a "stitched" (e.g., tandem or multiply stapled) polypeptide, in which two staples, e.g., are linked to a common residue. Peptide stitching is disclosed in U.S. Pat. Nos. 8,592,377 and 9,079,970, which are both hereby incorporated by reference in their entirety. In some instances, staples, as used herein, can retain the unsaturated bond or can be reduced (e.g., as mentioned below in the stitching paragraph description).

While many peptide staples have all hydrocarbon cross-links, other type of cross-links or staples can be used. For example, triazole-containing (e.g., 1, 4 triazole or 1, 5 triazole) crosslinks can be used (see, e.g., Kawamoto et al., *J. Med. Chem.* 55:1137-1146, 2012; WO 2010/060112).

Stapling of a peptide using an all-hydrocarbon cross-link has been shown to help maintain its native conformation and/or secondary structure, particularly under physiologically relevant conditions (see, e.g., Schafmiester et al., *J. Am. Chem. Soc.* 122:5891-5892, 2000; Walensky et al., *Science* 305:1466-1470, 2004).

Stapling the polypeptide herein by an all-hydrocarbon crosslink predisposed to have an alpha-helical secondary structure can constrain the polypeptide to its native alpha-helical conformation. The constrained secondary structure can, for example, increase the peptide's resistance to proteolytic cleavage, can increase the peptide's thermal stability, can increase the peptide's hydrophobicity, can allow for better penetration of the peptide into the target cell's membrane (e.g., through an energy-dependent transport mechanism, such as pinocytosis), and/or can lead to an improvement in the peptide's biological activity relative to the corresponding uncross-linked (e.g., "unstitched" or "unstapled") peptide.

While at least two amino acids are required to support an internal cross-link (e.g., a staple), additional pairs of internally cross-linked amino acids can be included in a internally cross-linked polypeptide or modified polypeptide, e.g., to support additional internal cross-links (e.g., staples). For example, internally cross-linked polypeptides and modified polypeptides can include 1, 2, 3, 4, 5, or more staples. Internally cross-linked polypeptides and modified polypeptides (e.g., stapled and/or stitched peptides) are generally referred to herein as "stabilized alpha-helix of BCL-2 domains" (SAHBs).

Alternatively or in addition, internally cross-linked polypeptides and modified polypeptides can include three internally cross-linked or stitched amino acids, e.g., yielding two staples arising from a common origin. A peptide stitch includes at least three internally cross-linked amino acids, wherein the middle of the three amino acids (referred to here as the core or central amino acid and shown as "i") forms an internal cross-link (between alpha carbons) with each of the two flanking modified amino acids. The alpha carbon of the core amino acid has side chains that are internal cross-links to the alpha carbons of other amino acids in the peptide, which can be saturated or not saturated. Amino acids cross-linked to the core amino acid can be separated from the core amino acid in either direction by 2, 3, or 6 amino acids (e.g. i, i–3, i, i–4, i, i–7 or, i, i+3, i, i+4, i, i+7), where "i" is the core amino acid). The number of amino acids on either side of the core (e.g., between the core amino acid and an amino acid cross-linked to the core) can be the same or different. In some instances, a stitch can include 3, 4, 5, or more internally cross-linked amino acids. In some instances, internally cross-linked polypeptides and modified polypeptides can include 1, 2, 3, 4, 5, or more stitches.

In some aspects, internally cross-linked polypeptides or modified polypeptides described herein can include a combination of at least one (e.g., 1, 2, 3, 4, or 5) staple and at least one (e.g., 1, 2, 3, 4, or 5) stitch.

Internal cross-links (e.g., staples and/or stitches) can be positioned on amino acids within an internally cross-linked polypeptide or modified polypeptide to conserve the structural relationship of amino acids in the binding or the interacting face of the peptide (e.g., to preserve the binding interface of a peptide). Alternatively, staples can placed on the interacting face as long as binding affinity or activity is not altered. The "interacting face" of the internally cross-linked polypeptides described herein includes those amino acid residues of the alpha helix that interact (e.g., interact specifically or bind specifically) with a BAX protein. In some aspects, the staple or staples can be placed such that they partially or completely engage the target and enhance binding activity. For example, staples or stitches can be placed to conserve the structural relationship of amino acids in an interaction face of the internally cross-stitched polypeptide or modified polypeptide. Such internal cross-links can include: one or more staples; one or more stitches; and/or a combination of one or more staples with one or more stitches.

Selection of amino acids for modification (e.g., to support an internal cross-link) can also be facilitated by staple scanning. The term "staple scan" refers to the synthesis of a library of stapled peptides whereby the location of the i and i+3; i and i+4; and i and i+7 single and multiple staple, or stitches, are positioned sequentially down the length of the peptide sequence, sampling all possible positions, to identify desired or optimal properties and activities for the stapled or stitched constructs.

In some aspects, the tethers, e.g., hydrocarbon staples are used to stabilize structures other than helices. In such cases, the ends of the tethers can be placed at intervals other than at i, i+3, i+4, and i+7.

Structurally constrained peptides and the like are understood to include modified peptides having any (i.e., at least one) chemical modification, e.g., mutation of the original or native sequence with a natural or non-natural amino acid; chemical modification to incorporate a molecular tether, chemical modification to promote the formation of a disulfide bridge, etc., such that the structurally constrained peptide adopts a more limited number of structures than the unmodified peptide. A structurally constrained peptide can include 1, 2, 3, 4, 5, 6, 7, 8, 9, 10, 11, 12, or more mutations as compared to the native, wild-type sequence. For example, molecular tethers can include hydrocarbon staples to promote the formation of stable helical structures, especially alpha-helical and $3_{10}$ helix structures, or kinks depending on the positions of the ends of the tethers and the lengths of the tethers. Natural or non-natural amino acids can be employed to promote kinks (e.g., bends in the structure as defined by the variable angles between the two adjoining structures) or other preferred confirmations. For example, the natural amino acid proline can induce a kink in a peptide due to the structure of the amino acid R group and the lack of a hydrogen-bond donor. Non-natural amino acids, particularly those having large and/or charged R groups, or N-methylated amides, N-substituted glycines, cyclic alpha, alpha-disubstitution, cyclic N,N-disubstitution, and beta-amino acids can promote specific, desired confirmations. It is understood that a population of "structurally constrained" peptides in solution can not all have the desired confirmation all of the time. Instead, in a population of structurally constrained peptides in solution, the desired confirmation is present at least about 30%, 40%, 50%, 60%, 70%, 80%, 900%, 100%, or more of the time than the native or original peptide sequence in solution prior to chemical modification. The structure of a population of peptides in solution can be determined by various methods known to those of skill in the art including, but not limited to, circular dichroism and NMR spectroscopy. X-ray crystallography can be applied to determine the structure of a constrained peptide when packed in the form of a crystal.

Suitable tethers are described herein and in U.S. Patent Application Publication No. 2005/0250680, U.S. Pat. No. 8,592,377, U.S. Patent Application Publication No. 2011/0318352, WO 2009/108261, and WO 2010/148335, each of which are herein incorporated by reference in their entireties.

Amino acid side chains suitable for use in the internally cross-linked polypeptides and modified polypeptides disclosed herein are known in the art. For example, suitable amino acid side chains include methyl (as the alpha-amino acid side chain for alanine is methyl), 4-hydroxyphenylmethyl (as the alpha-amino acid side chain for tyrosine is 4-hydroxyphenylmethyl) and thiomethyl (as the alpha-amino acid side chain for cysteine is thiomethyl), etc. A "terminally unsaturated amino acid side chain" refers to an amino acid side chain bearing a terminal unsaturated moiety, such as a substituted or unsubstituted, double bond (e.g., olefinic) or triple bond (e.g., acetylenic), that participates in cross-linking reaction with other terminal unsaturated moieties in the polypeptide chain. In certain aspects, a "terminally unsaturated amino acid side chain" is a terminal olefinic amino acid side chain. In certain aspects, a "terminally unsaturated amino acid side chain" is a terminal acetylenic amino acid side chain. In certain aspects, the terminal moiety of a "terminally unsaturated amino acid side chain" is not further substituted.

As noted above, an internal tether or cross-link can extend across the length of one helical turn (i.e., about 3.4 amino acids (i.e., i, i+3, or i, i+4) or two helical turns (i.e., about 7 amino acids (i.e., i, i+7). Accordingly, amino acids positioned at i and i+3; i and i+4; or i and i+7 of SEQ ID NO:2 or 3 are ideal candidates for chemical modification and cross-linking. Thus, e.g., where a peptide has the sequence . . . $Xaa_1$, $Xaa_2$, $Xaa_3$, $Xaa_4$, $Xaa_5$, $Xaa_6$, $Xaa_7$, $Xaa_8$, $Xaa_9$ . . . (wherein " . . . " indicates the optional presence of additional amino acids), cross-links between $Xaa_1$ and $Xaa_4$, or between $Xaa_1$ and $Xaa_5$, or between $Xaa_1$ and $Xaa_8$ are useful, as are cross-links between $Xaa_2$ and $Xaa_5$, or between $Xaa_2$ and $Xaa_6$, or between $Xaa_2$ and $Xaa_9$, etc.

Internally cross-linked polypeptides and modified polypeptides can include more than one crosslink within the polypeptide sequence to either further stabilize the sequence or facilitate the stabilization of longer polypeptide stretches. If the polypeptides are too long to be readily synthesized in one part, independently synthesized, internally cross-linked polypeptides or modified polypeptides can be conjoined by a technique called native chemical ligation (see, e.g., Bang, et al., *J. Am. Chem. Soc.* 126:1377-1383, 2004). Alternately, large peptides are routinely synthesized using a convergent approach, whereby fully protected fragments are specifically and sequentially reacted to form the full length desired product, after final deprotection, such as in the industrial synthesis of Fuzeon.

The invention features a modified polypeptide of Formula (I),

Formula (I)

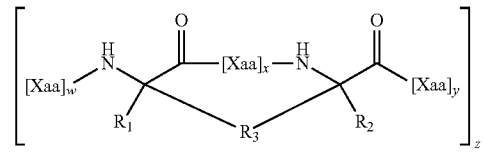

or a pharmaceutically acceptable salt thereof, wherein;

each $R_1$ and $R_2$ are independently H or a $C_1$ to $C_{10}$ alkyl, alkenyl, alkynyl, arylalkyl, cycloalkylalkyl, heteroarylalkyl, or heterocyclylalkyl;

$R_3$ is alkylene, alkenylene, or alkynylene (e.g., a $C_6$, $C_7$, $C_8$, $C_{11}$, $C_{12}$, or $C_{13}$ alkylene), or $[R_4'-K-R_4]_n$; each of which is substituted with 0-6 $R_5$;

$R_4$ and $R4'$ are independently alkylene, alkenylene, or alkynylene (e.g., each are independently a $C_1$, $C_2$, $C_3$, $C_4$, $C_5$, $C_6$, $C_7$, $C_8$, $C_9$, or $C_{10}$ alkylene, alkenylene or alkynylene);

$R_5$ is halo, alkyl, $OR_6$, $N(R_6)_2$, $SR_6$, $SOR_6$, $SO_2R_6$, $CO_2R_6$, $R_6$, a fluorescent moiety, or a radioisotope;

K is O, S, SO, $SO_2$, CO, $CO_2$, $CONR_6$,

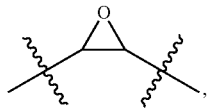 [SMILES: *C1OC1*]

aziridine, episulfide, diol, or amino alcohol;

$R_6$ is H, alkyl, or a therapeutic agent;

n is 2, 3, 4, or 6;

x is an integer from 2-10;

w and y are each independently an integer from 0-100;

z is an integer from 1-10 (e.g., 1, 2, 3, 4, 5, 6, 7, 8, 9, or 10); and each Xaa is independently an amino acid (e.g., one of the 20 naturally occurring amino acids or any naturally occurring non-naturally occurring amino acid);

wherein the polypeptide comprises at least 8 (e.g., at least 9, 10, 11, 12, 13, 14, 15, 16, 17, or 18) contiguous amino acids of SEQ ID NO: 2 or 3 or a variant thereof (e.g., one, two, three, four, five, six, or seven amino acid substitutions), or another polypeptide sequence described herein, except that: (a) within the 8 contiguous (e.g., 9, 10, 11, 12, 13, 14, 15, 16, 17, or 18) amino acids of SEQ ID NO: 2 or 3 the side chains of at least one pair (e.g., one, two, three, or four pairs) of amino acids separated by 2 to 6 amino acids (e.g., 2, 3, or 6 amino acids) is replaced by the linking group, $R_3$, which connects the alpha carbons of the pair of amino acids as depicted in Formula I; and (b) the alpha carbon of the first of the pair of amino acids is substituted with $R_1$ as depicted in Formula I and the alpha carbon of the second of the pair of amino acids is substituted with $R_2$ as depicted in Formula I.

In another aspect, the invention features a modified polypeptide of Formula (II), Formula (II)

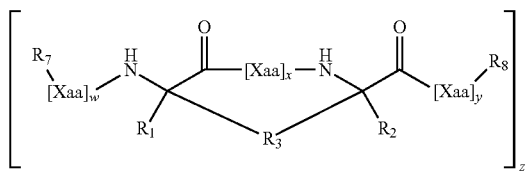

or a pharmaceutically acceptable salt thereof, wherein;

each $R_1$ and $R_2$ are independently H or a $C_1$ to $C_{10}$ alkyl, alkenyl, alkynyl, arylalkyl, cycloalkylalkyl, heteroarylalkyl, or heterocyclylalkyl;

$R_3$ is alkylene, alkenylene, or alkynylene (e.g., a $C_6$, $C_7$, $C_8$, $C_{11}$, $C_{12}$, or $C_{13}$ alkylene) or $[R_4'-K-R_4]_n$; each of which is substituted with 0-6 $R_5$;

$R_4$ and $R_4'$ are independently alkylene, alkenylene, or alkynylene (e.g., each are independently a $C_1$, $C_2$, $C_3$, $C_4$, $C_5$, $C_6$, $C_7$, $C_8$, $C_9$, or $C_{10}$ alkylene, alkenylene, or alkynylene);

$R_5$ is halo, alkyl, $OR_6$, $NHR_6$, $N(R_6)_2$, $SR_6$, $SOR_6$, $SO_2R_6$, $CO_2R_6$, $R_6$, a fluorescent moiety, or a radioisotope;

K is O, S, SO, $SO_2$, CO, $CO_2$, $CONR_6$,

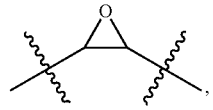 [SMILES: *C1OC1*]

aziridine, episulfide, diol, amino alcohol, or diamine;

$R_6$ is H, alkyl, or a therapeutic agent;

n is 2, 3, 4, 5, or 6;

x is an integer from 2-10;

w and y are each independently an integer from 0-100;

z is an integer from 1-10 (e.g., 1, 2, 3, 4, 5, 6, 7, 8, 9, or 10); and each Xaa is independently an amino acid (e.g., one of the 20 naturally occurring amino acids or any naturally occurring non-naturally occurring amino acid);

$R_7$ is selected from: a) PEG, b) a tat protein, c) an affinity label, d) a targeting moiety, e) a fatty acid-derived acyl group, f) a biotin moiety, g) a fluorescent probe (e.g., fluorescein or rhodamine) linked via, e.g., a thiocarbamate or carbamate linkage, or h) a sequence of 2, 3, 4, 5, 6, 6, 8, or 9 contiguous Arg;

$R_8$ is H, OH, $NH_2$, $NHR_{8a}$, or $NR_{8a}R_{8b}$;

wherein the polypeptide comprises at least 8 contiguous amino acids (e.g., 9, 10, 11, 12, 13, 14, 15, 16, 17, or 18) of SEQ ID NO: 2 or 3 or a variant thereof (e.g., one, two, three, four, five, six, or seven amino acid substitutions), or another polypeptide sequence described herein except that: (a) within the at least 8 (e.g., 9, 10, 11, 12, 13, 14, 15, 16, 17, or 18) contiguous amino acids of any one of SEQ ID NO: 2 or 3, the side chains of at least one (e.g., 2, 3, 4, or 5) pair of amino acids separated by 2 to 6 amino acids (e.g., 2, 3, or 6 amino acids) is replaced by the linking group, $R_3$, which connects the alpha carbons of the pair of amino acids as depicted in Formula II; and (b) the alpha carbon of the first of the pair of amino acids is substituted with $R_1$ as depicted in Formula II and the alpha carbon of the second of the pair of amino acids is substituted with $R_2$ as depicted in Formula II.

In the case of Formula I or Formula II, the following aspects are among those disclosed.

In cases where x=2 (i.e., i+3 linkage), $R_3$ can be a $C_7$ alkylene or alkenylene. Where it is an alkenylene, there can one or more double bonds. In cases where x=6 (i.e., i+4 linkage), $R_3$ can be a $C_{11}$, $C_{12}$, or $C_{13}$ alkylene or alkenylene. Where it is an alkenylene, there can one or more double bonds. In cases where x=3 (i.e., i+4 linkage), $R_3$ can be a $C_8$ alkylene or alkenylene. Where it is an alkenylene, there can one or more double bonds.

In certain instances, the two alpha, alpha-disubstituted stereocenters (alpha carbons) are both in the R configuration or S configuration (e.g., i, i+4 cross-link), or one stereocenter is R and the other is S (e.g., i, i+7 cross-link). Thus, where Formula I is depicted as

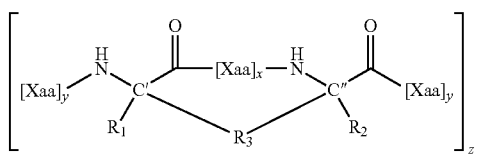

the C' and C" disubstituted stereocenters can both be in the R configuration or they can both be in the S configuration, for example, when x is 3. When x is 6, the C' disubstituted stereocenter is in the R configuration and the C" disubstituted stereocenter is in the S configuration or the C' disubstituted stereocenter is in the S configuration and the C" disubstituted stereocenter is in the R configuration. The $R_3$ double bond can be in the E or Z stereochemical configuration. Similar configurations are possible for the carbons in Formula II corresponding to C' and C" in the formula depicted immediately above.

In some instances R3 is $[R_4—K—R_4']_n$; and $R_4$ and R4' are independently alkylene, alkenylene, or alkynylene (e.g., each are independently a $C_1$, $C_2$, $C_3$, $C_4$, $C_5$, $C_6$, $C_7$, $C_8$, $C_9$, or $C_{10}$ alkylene, alkenylene or alkynylene).

In some instances of any of the modified polypeptides described herein, the modified polypeptide includes an amino acid sequence which, in addition to the amino acids side chains that are replaced by a cross-link, have 1, 2, 3, 4, 5, 6, 7, 8, 9, 10, 11, or 12 amino acid changes (e.g., conservative amino acid changes) in SEQ ID NO: 2 or 3.

The tether can include an alkyl, alkenyl, or alkynyl moiety (e.g., $C_6$, $C_8$, or $C_{11}$ alkyl, a $C_6$, $C_8$, or $C_{11}$ alkenyl, or $C_5$, $C_8$, or $C_{11}$ alkynyl). The tethered amino acid can be alpha disubstituted (e.g., $C_1$-$C_3$ or methyl). $[Xaa]_y$ and $[Xaa]_w$ are peptides that can independently comprise at least 1, 2, 3, 4, 5, 6, 7, 8, 9, 10, 11, 12, 13, 14, 15, 16, 17, or 18 contiguous amino acids of SEQ ID NO: 3 and [Xaa]X is a peptide that can comprise between 2 to 7 (e.g., 2, 3, 6, or 7) contiguous amino acids of acids of SEQ ID NO: 2 or 3.

The internally cross-linked polypeptides and modified polypeptides can contain one or more asymmetric centers and thus occur as racemates and racemic mixtures, single enantiomers, individual diastereomers, and diastereomeric mixtures and geometric isomers (e.g., Z or cis and E or trans) of any olefins present. For example, internally cross-linked polypeptides or modified polypeptides disclosed herein can exist in particular geometric or stereoisomeric forms, including, for example, cis- and trans-isomers, R- and S-enantiomers, diastereomers, (D)-isomers, (L)-isomers, the racemic mixtures thereof, and other mixtures thereof. Enantiomers can be free (e.g., substantially free) of their corresponding enantiomer, and/or can also be optically enriched. "Optically enriched," as used herein, means that the compound is made up of a significantly greater proportion of one enantiomer. In certain aspects substantially free means that a composition contains at least about 90% by weight of a preferred enantiomer. In other aspects the compound is made up of at least about 95%, 98%, or 99% by weight of a preferred enantiomer. Preferred enantiomers can be isolated from racemic mixtures using techniques known in the art, including, but not limited to, for example, chiral high pressure liquid chromatography (HPLC) and the formation and crystallization of chiral salts or prepared by asymmetric syntheses (see, e.g., Jacques, et al., Enantiomers, Racemates and Resolutions (Wiley Interscience, New York, 1981); Wilen, S. H. et al., *Tetrahedron* 33:2725 (1977); Eliel, E X, Stereochemistry of Carbon Compounds (McGraw-Hill, N Y, 1962); Wilen, S. H., Tables of Resolving Agents and Optical Resolutions p. 268 (EX. Eliel, Ed., Univ. of Notre Dame Press, Notre Dame, Ind., 1972). All such isomeric forms of these internally cross-linked polypeptides and modified polypeptides are expressly included in the present invention.

The internally cross-linked polypeptides or modified polypeptides can also be represented in multiple tautomeric forms, in such instances, the invention expressly includes all tautomeric forms of the compounds described herein (e.g., isomers in equilibrium (e.g., keto-enol), wherein alkylation at multiple sites can yield regioisomers), regioisomers, and oxidation products of the internally cross-linked polypeptides or modified polypeptides disclosed herein (the invention expressly includes all such reaction products). All such isomeric forms of such internally cross-linked polypeptides or modified polypeptides are included, as are all crystal forms.

The symbol "⌇," when used as part of a molecular structure, refers to a single bond or a trans or cis double bond.

The term "halo" refers to any radical of fluorine, chlorine, bromine, or iodine. The term "alkyl" refers to a hydrocarbon chain that can be a straight chain or branched chain, containing the indicated number of carbon atoms. For example, $C_1$-$C_{10}$ indicates that the group can have from 1 to 10 (inclusive) carbon atoms in it. In the absence of any numerical designation, "alkyl" is a chain (straight or branched) having 1 to 20 (inclusive) carbon atoms in it. The term "alkylene" refers to a divalent alkyl (i.e., —R—).

The term "alkenyl" refers to a hydrocarbon chain that can be a straight chain or branched chain having one or more carbon-carbon double bonds in either Z or E geometric configurations. The alkenyl moiety contains the indicated number of carbon atoms. For example, $C_2$-$C_{10}$ indicates that the group can have from 2 to 10 (inclusive) carbon atoms in it. The term "lower alkenyl" refers to a $C_2$-$C_8$ alkenyl chain. In the absence of any numerical designation, "alkenyl" is a chain (straight or branched) having 2 to 20 (inclusive) carbon atoms in it.

The term "alkynyl" refers to a hydrocarbon chain that can be a straight chain or branched chain having one or more carbon-carbon triple bonds. The alkynyl moiety contains the indicated number of carbon atoms. For example, $C_2$-$C_{10}$ indicates that the group can have from 2 to 10 (inclusive) carbon atoms in it. The term "lower alkynyl" refers to a $C_2$-$C_8$ alkynyl chain. In the absence of any numerical designation, "alkynyl" is a chain (straight or branched) having 2 to 20 (inclusive) carbon atoms in it.

The term "aryl" refers to a 6-carbon monocyclic or 10-carbon bicyclic aromatic ring system wherein 0, 1, 2, 3, 4, or 5 atoms of each ring can be substituted by a substituent. Examples of aryl groups include phenyl, naphthyl, and the like. The term "arylalkyl" or the term "aralkyl" refers to alkyl substituted with an aryl. The term "arylalkoxy" refers to an alkoxy substituted with aryl.

The term "cycloalkyl" as employed herein includes saturated and partially unsaturated cyclic hydrocarbon groups having 3 to 12 carbons, preferably 3 to 8 carbons, and more preferably 3 to 6 carbons, wherein the cycloalkyl group additionally can be optionally substituted. Preferred cycloalkyl groups include, without limitation, cyclopropyl, cyclobutyl, cyclopentyl, cyclopentenyl, cyclohexyl, cyclohexenyl, cyclohexadienyl, cycloheptyl, cycloheptadienyl, cycloheptatrienyl, cyclooctyl, cyclooctenyl, cyclooctadienyl, cyclooctatrienyl, and cyclooctynyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring can be substituted by a substituent. Examples of heteroaryl groups include pyrrolyl, pyridyl, furyl or furanyl, imidazolyl, 1,2,3-triazolyl, 1,2,4-triazolyl, benzimidazolyl, pyridazyl, pyrimidyl, thiophenyl, quinolinyl, indolyl, thiazolyl, oxazolyl, isoxazolyl, and the like. The term "heteroarylalkyl" or the term "heteroaralkyl" refers to an alkyl substituted with a heteroaryl. The term "heteroarylalkoxy" refers to an alkoxy substituted with heteroaryl.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring can be substituted by a substituent. Examples of heterocyclyl groups include piperazinyl, pyrrolidinyl, dioxanyl, aziridinyl, oxiryl, thiiryl, morpholinyl, tetrahydrofuranyl, and the like.

The term "substituents" refers to a group "substituted" on an alkyl, cycloalkyl, aryl, heterocyclyl, or heteroaryl group at any atom of that group. Suitable substituents include, without limitation, halo, hydroxy, mercapto, oxo, nitro, haloalkyl, alkyl, alkaryl, aryl, aralkyl, alkoxy, thioalkoxy, aryloxy, amino, alkoxycarbonyl, amido, carboxy, alkanesulfonyl, alkylcarbonyl, azido, and cyano groups.

In some instances, the hydrocarbon tethers (i.e., cross-links) described herein can be further manipulated. In one instance, a double bond of a hydrocarbon alkenyl tether (e.g., as synthesized using a ruthenium-catalyzed ring closing metathesis (RCM)) can be oxidized (e.g., via epoxidation or dihydroxylation) to provide one of compounds below.

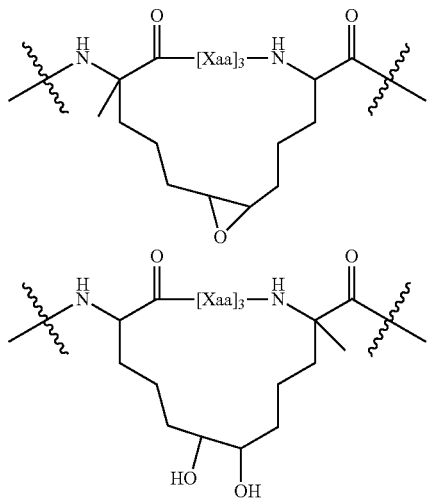

Either the epoxide moiety or one of the free hydroxyl moieties can be further functionalized. For example, the epoxide can be treated with a nucleophile, which provides additional functionality that can be used, for example, to attach a tag (e.g., a radioisotope or fluorescent tag). The tag can be used to help direct the compound to a desired location in the body or track the location of the compound in the body. Alternatively, an additional therapeutic agent can be chemically attached to the functionalized tether (e.g., a cytoprotective agent). Such derivatization can alternatively be achieved by synthetic manipulation of the amino or carboxy-terminus of the internally cross-linked polypeptide or modified polypeptide, or via the amino acid side chain. Other agents can be attached to the functionalized tether, e.g., an agent that facilitates entry of the internally cross-linked polypeptide or modified polypeptide into cells.

While hydrocarbon tethers (cross-links) have been described, other tethers (cross-linkers) are also envisioned. For example, the tether can include one or more of an ether, thioether, ester, amine, or amide moiety. In some cases, a naturally-occurring amino acid side chain can be incorporated into the tether. For example, a tether can be coupled with a functional group such as the hydroxyl in serine, the thiol in cysteine, the primary amine in lysine, the acid in aspartate or glutamate, or the amide in asparagine or glutamine. Accordingly, it is possible to create a tether using naturally-occurring amino acids rather than using a tether that is made by coupling two non-naturally occurring amino acids. It is also possible to use a single non-naturally occurring amino acid together with a naturally occurring amino acid.

It is further envisioned that the length of the tether (cross-link) can be varied. For instance, a shorter length of tether can be used where it is desirable to provide a relatively high degree of constraint on the secondary alpha-helical structure, whereas, in some instances, it is desirable to provide less constraint on the secondary alpha-helical structure, and thus a longer tether can be desired.

Additionally, while examples of tethers (cross-links) spanning from amino acids i to i+3, i to i+4: and i to i+7 have been described in order to provide a tether that is primarily on a single face of the alpha helix, the tethers can be synthesized to span any combinations of numbers of amino acids (e.g., i to i+7).

In some instances, alpha-disubstituted amino acids are used in the internally cross-linked polypeptide or modified polypeptide to improve the stability of the alpha-helical secondary structure. However, alpha-disubstituted amino acids are not required, and instances using mono-alpha substituents (e.g., in the tethered amino acids) are also envisioned.

In some instances, it can be useful to replace an amino acid on the interacting face of SEQ ID NO: 2 or 3 with another amino acid, e.g., Ala. Such inactive internally cross-linked polypeptides or modified polypeptides can be useful, e.g., as negative controls.

The internally cross-linked polypeptides or modified polypeptides can include a drug, a toxin, a derivative of polyethylene glycol; a second polypeptide; a carbohydrate, etc. Where a polymer or other agent is linked to the internally cross-linked polypeptide or modified polypeptide it can be desirable for the composition containing these internally cross-linked polypeptides or modified polypeptides to be substantially homogeneous.

The addition of polyethelene glycol (PEG) molecules can improve the pharmacokinetic and pharmacodynamic properties of the modified polypeptide or internally cross-linked polypeptide. For example, PEGylation can reduce renal clearance and can result in a more stable plasma concentration. PEG is a water soluble polymer and can be represented as linked to the polypeptide as formula:

XO—(CH$_2$CH$_2$O)$_n$—CH$_2$CH$_2$—Y where n is 2 to 10,000 and X is H or a terminal modification, e.g., a C$_{1-4}$ alkyl; and Y is an amide, carbamate, or urea linkage to an amine group (including but not limited to, the epsilon amine of lysine or the N-terminus) of the internally cross-linked polypeptide or modified polypeptide. Y can also be a maleimide linkage to a thiol group (including but not limited to, the thiol group of cysteine). Other methods for linking PEG to a polypeptide, directly or indirectly, are known to those of ordinary skill in the art. The PEG can be linear or branched. Various forms of PEG including various functionalized derivatives are commercially available.

PEG having degradable linkages in the backbone can be used. For example, PEG can be prepared with ester linkages that are subject to hydrolysis. Conjugates having degradable PEG linkages are described in WO 99/34833; WO 99/14259, and U.S. Pat. No. 6,348,558.

In certain aspects, macromolecular polymer (e.g., PEG) is attached to a modified polypeptide or internally cross-linked polypeptide described herein through an intermediate linker. In certain aspects, the linker is made up of from 1 to 50 (e.g., 5, 15, 20, 25) amino acids linked by peptide bonds, wherein the amino acids are selected from the 20 naturally-occurring amino acids. Some of these amino acids can be glycosylated, as is well understood by those in the art. In other aspects, the 1 to 50 amino acids are selected from glycine, alanine, proline, asparagine, glutamine, and lysine. In other aspects, a linker is made up of a majority of amino acids that are sterically unhindered, such as glycine and alanine. In other aspects, a linker includes glycine and/or serine (e.g., G4S (SEQ ID NO: 33)). Non-peptide linkers are also possible. For example, alkyl linkers such as —NH(CH$_2$)$_n$C(O)—, wherein n=2-20 can be used. These alkyl linkers can further be substituted by any non-sterically hindering group such as lower alkyl (e.g., C$_1$-C$_6$), lower acyl, halogen (e.g., Cl, Br), CN, NH$_2$, phenyl, etc. U.S. Pat. No. 5,446,090 describes a bifunctional PEG linker and its use in forming conjugates having a peptide at each of the PEG linker termini.

The internally cross-linked polypeptides or modified polypeptides can also be modified, e.g., to further facilitate cellular uptake or increase in vivo stability, in some aspects. For example, acylating or PEGylating a peptidomimetic facilitates cellular uptake, increases bioavailability, increases blood circulation, alters pharmacokinetics, decreases immunogenicity, and/or decreases the needed frequency of administration.

In some aspects, the internally cross-linked polypeptides or modified polypeptides disclosed herein have an enhanced ability to penetrate cell membranes (e.g., relative to non-stapled peptides).

Methods of Making Internally Cross-Linked Polypeptides

Methods of synthesizing the internally cross-linked polypeptides or modified polypeptides described herein are known in the art. Nevertheless, the following exemplary method can be used. It will be appreciated that the various steps can be performed in an alternate sequence or order to give the desired compounds. Synthetic chemistry transformations and protecting group methodologies (protection and deprotection) useful in synthesizing the internally cross-linked polypeptides and modified polypeptides described herein are known in the art and include, e.g., those such as described in R. Larock, Comprehensive Organic Transformations, VCH Publishers (1989); T. W. Greene and P. G. M. Wuts, Protective Groups in Organic Synthesis, 3d. Ed., John Wiley and Sons (1999); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

The internally cross-linked polypeptides and modified polypeptides of this invention can be made by chemical synthesis methods, which are well known to the ordinarily skilled artisan. See, e.g., Fields et al., Chapter 3 in Synthetic Peptides: A User's Guide, ed. Grant, W. H. Freeman & Co., New York, N.Y., 1992, p. 77. Hence, peptides can be synthesized using the automated Merrifield techniques of solid phase synthesis with the α-NH$_2$ protected by either t-Boc or Fmoc chemistry using side chain protected amino acids on, e.g., an Applied Biosystems Peptide Synthesizer Model 430A or 431.

One manner of making of the cross-linked polypeptides or modified polypeptides described herein is using solid phase peptide synthesis (SPPS). The C-terminal amino acid is attached to a cross-linked polystyrene resin via an acid labile bond with a linker molecule. This resin is insoluble in the solvents used for synthesis, making it relatively simple and fast to wash away excess reagents and by-products. The N-terminus is protected with the Fmoc group, which is stable in acid, but removable by base. Any side chain functional groups are protected with base stable, acid labile groups.

Longer peptides can be made by conjoining individual synthetic peptides using native chemical ligation. Alternatively, the longer synthetic peptides can be synthesized by well-known recombinant DNA techniques. Such techniques are provided in well-known standard manuals with detailed protocols. To construct a gene encoding a peptide of this invention, the amino acid sequence is reverse translated to obtain a nucleic acid sequence encoding the amino acid sequence, preferably with codons that are optimum for the organism in which the gene is to be expressed. Next, a synthetic gene is made, typically by synthesizing oligonucleotides which encode the peptide and any regulatory elements, if necessary. The synthetic gene is inserted in a suitable cloning vector and transfected into a host cell. The peptide is then expressed under suitable conditions appropriate for the selected expression system and host. The peptide is purified and characterized by standard methods. The peptides can be made in a high-throughput, combinatorial fashion, e.g., using a high-throughput multiple channel combinatorial synthesizer available from Advanced Chemtech.

One or more peptide bonds can be replaced, e.g., to increase physiological stability of the internally cross-linked polypeptide or modified polypeptide, by: a retro-inverso bonds (C(O)—NH); a reduced amide bond (NH—CH$_2$); a thiomethylene bond (S—CH$_2$ or CH$_2$—S); an oxomethylene bond (O—CH$_2$ or CH$_2$—O); an ethylene bond (CH$_2$—CH$_2$); a thioamide bond (C(S)—NH); a trans-olefin bond (CH=CH); a fluoro-substituted trans-olefin bond (CF=CH); a ketomethylene bond (C(O)—CHR) or CHR—C(O), wherein R is H or CH$_3$; and a fluoro-ketomethylene bond (C(O)—CFR or CFR—C(O), wherein R is H, F, or CH$_3$.

The internally cross-linked polypeptides or modified polypeptides can be further modified by one or more of: acetylation, amidation, biotinylation, cinnamoylation, farnesylation, fluoresceination, formylation, myristoylation, palmitoylation, phosphorylation (Ser, Tyr, or Thr), stearoylation, succinylation, and sulfurylation. As indicated above, internally cross-linked polypeptides and modified polypeptides can be conjugated to, for example, polyethylene glycol (PEG); alkyl groups (e.g., $C_1$-$C_{20}$ straight or branched alkyl groups); fatty acid radicals; and combinations thereof.

α, α-Disubstituted non-natural amino acids containing olefinic side chains of varying length can be synthesized by known methods (see, e.g., Williams et al., *J. Am. Chem. Soc.* 113:9276, 1991; Schafmeister et al., *J. Am. Chem Soc.* 122:5891, 2000; Bird et al., *Methods Enzymol.,* 446:369, 2008; Bird et al, *Current Protocols in Chemical Biology,* 2011). For internally cross-linked polypeptides or modified polypeptides, where an i linked to i+7 staple is used (two turns of the helix stabilized), either one $S_5$ amino acid and one $R_8$ is used, or one $S_8$ amino acid and one $R_5$ amino acid is used. $R_8$ is synthesized using the same route, except that the starting chiral auxillary confers the R-alkyl-stereoisomer. Also, 8-iodooctene is used in place of 5-iodopentene. Inhibitors are synthesized on a solid support using solid-phase peptide synthesis (SPPS) on MBHA resin (see, e.g., WO 2010/148335).

Fmoc-protected α-amino acids (other than the olefinic amino acids Fmoc-$S_5$—OH, Fmoc-$R_8$—OH, Fmoc-$R_8$—OH, Fmoc-$S_8$—OH, and Fmoc-$R_5$—OH), 2-(6-chloro-1-H-benzotriazole-1-yl)-1,1,3,3-tetramethylaminium hexafluorophosphate (HCTU), and Rink Amide MBHA are commercially available from, e.g., Novabiochem (San Diego, Calif.). Dimethylformamide (DMF), N-methyl-2-pyrrolidinone (NMP), N,N-diisopropylethylamine (DIEA), trifluoroacetic acid (TFA), 1,2-dichloroethane (DCE), fluorescein isothiocyanate (FITC), and piperidine are commercially available from, e.g., Sigma-Aldrich. Olefinic amino acid synthesis is reported in the art (Williams et al., *Org. Synth.,* 80:31, 2003).

In some instances, the internally cross-linked polypeptides and modified polypeptides can include a detectable label. As used herein, a "label" refers to a moiety that has at least one element, isotope, or functional group incorporated into the moiety which enables detection of the peptide (e.g., internally cross-linked polypeptide or modified polypeptide) to which the label is attached. Labels can be directly attached (i.e., via a bond) or can be attached by a linker (e.g., such as, for example, a cyclic or acyclic, branched or unbranched, substituted or unsubstituted alkylene; cyclic or acyclic, branched or unbranched, substituted or unsubstituted alkenylene; cyclic or acyclic, branched or unbranched, substituted or unsubstituted alkynylene; cyclic or acyclic, branched or unbranched, substituted or unsubstituted heteroalkylene; cyclic or acyclic, branched or unbranched, substituted or unsubstituted heteroalkenylene; cyclic or acyclic, branched or unbranched, substituted or unsubstituted heteroalkynylene; substituted or unsubstituted arylene; substituted or unsubstituted heteroarylene; or substituted or unsubstituted acylene, or any combination thereof, which can make up a linker). Labels can be attached to an internally cross-linked polypeptide or modified polypeptide at any position that does not interfere with the biological activity or characteristic of the inventive internally cross-linked polypeptide or modified polypeptide that is being detected.

Labels can include: labels that contain isotopic moieties, which can be radioactive or heavy isotopes, including, but not limited to, $^2$H, $^3$H, $^{13}$C, $^{14}$C, $^{15}$N, $^{31}$P, $^{32}$P, $^{35}$S, $^{67}$Ga, $^{99m}$Tc (Tc-99m), $^{111}$In, $^{123}$I, $^{125}$I, $^{169}$Yb, and $^{186}$Re; labels that include immune or immunoreactive moieties, which can be antibodies or antigens, which can be bound to enzymes (e.g., such as horseradish peroxidase); labels that are colored, luminescent, phosphorescent, or include fluorescent moieties (e.g., such as the fluorescent label FITC); labels that have one or more photoaffinity moieties; labels that have ligand moieties with one or more known binding partners (such as biotin-streptavidin, FK506-FKBP, etc.).

In some instances, labels can include one or more photoaffinity moieties for the direct elucidation of intermolecular interactions in biological systems. A variety of known photophores can be employed, most relying on photoconversion of diazo compounds, azides, or diazirines to nitrenes or carbenes (see, e.g., Bayley, H., Photogenerated Reagents in Biochemistry and Molecular Biology (1983), Elsevier, Amsterdam, the entire contents of which are incorporated herein by reference). In certain aspects of the invention, the photoaffinity labels employed are o-, m- and p-azidobenzoyls, substituted with one or more halogen moieties, including, but not limited to 4-azido-2,3,5,6-tetrafluorobenzoic acid.

Labels can also be or can serve as imaging agents. Exemplary imaging agents include, but are not limited to, those used in positron emissions tomography (PET), computer assisted tomography (CAT), single photon emission computerized tomography, X-ray, fluoroscopy, and magnetic resonance imaging (MRI): anti-emetics: and contrast agents. Exemplary diagnostic agents include but are not limited to, fluorescent moieties, luminescent moieties, magnetic moieties; gadolinium chelates (e.g., gadolinium chelates with DTPA, DTPA-BMA, DOTA, and HP-DO3A), iron chelates, magnesium chelates, manganese chelates, copper chelates, chromium chelates, iodine-based materials useful for CAT and x-ray imaging, and radionuclides. Suitable radionuclides include, but are not limited to, $^{123}$I, $^{125}$I, $^{130}$I, $^{131}$I, $^{133}$I, $^{135}$I, $^{47}$Sc, $^{72}$As, $^{72}$Se, $^{90}$Y, $^{88}$Y, $^{97}$Ru, $^{100}$Pd, $^{101}$mRh, $^{119}$Sb, $^{128}$Ba, $^{197}$Hg, $^{211}$At, $^{212}$Bi, $^{212}$Pb, $^{109}$Pd, $^{111}$In, $^{67}$Ga, $^{68}$Ga, $^{67}$Cu, $^{75}$Br, $^{77}$Br, $^{99}$mTc, $^{14}$C, $^{13}$N, $^{15}$O, $^{32}$P, $^{33}$P, and $^{18}$F.

Fluorescent and luminescent moieties include, but are not limited to, a variety of different organic or inorganic small molecules commonly referred to as "dyes," "labels," or "indicators." Examples include, but are not limited to, fluorescein, rhodamine, acridine dyes, Alexa dyes, cyanine dyes, etc. Fluorescent and luminescent moieties may include a variety of naturally-occurring proteins and derivatives thereof, e.g., genetically engineered variants. For example, fluorescent proteins include green fluorescent protein (GFP), enhanced GFP, red, blue, yellow, cyan, and sapphire fluorescent proteins, reef coral fluorescent protein, etc. Luminescent proteins include luciferase and aequorin, and derivatives thereof. Numerous fluorescent and luminescent dyes and proteins are known in the art (see, e.g., U.S. Patent Application Publication No. 2004/0067503; Valeur, B., "Molecular Fluorescence: Principles and Applications," John Wiley and Sons, 2002; and Handbook of Fluorescent Probes and Research Products, Molecular Probes, 9th edition, 2002).

Again, methods suitable for obtaining (e.g., synthesizing), stapling, and purifying the internally cross-linked polypeptides and modified polypeptides disclosed herein are also known in the art (see, e.g., Bird et. al., *Methods in Enzymology* 446:369-386 (2008); Bird et al, *Current Protocols in Chemical Biology* 2011; Walensky et al., *Science* 305:1466-1470 (2004); Schafmeister et al., *J. Am. Chem. Soc.* 122: 5891-5892 (2000); U.S. Patent Application Publication No. 2010/0168388; and U.S. Pat. No. 7,723,468, each of which are hereby incorporated by reference in their entirety).

In some embodiments, the internally cross-linked polypeptides or modified polypeptides are substantially free of non-stapled peptide contaminants or are isolated. Methods for purifying internally cross-linked polypeptides or modified polypeptides include, for example, synthesizing the peptide on a solid-phase support. Following cyclization, the solid-phase support may be isolated and suspended in a solution of a solvent such as DMSO, DMSO/dichloromethane mixture, or DMSO/NMP mixture. The DMSO/dichloromethane or DMSO/NMP mixture may comprise about 30%, 40%, 50%, or 60% DMSO. In a specific embodiment, a 50%/50% DMSO/NMP solution is used. The solution may be incubated for a period of 1, 6, 12, or 24 hours, following which the resin may be washed, for example with dichloromethane or NMP. In one embodiment, the resin is washed with NMP. Shaking and bubbling an inert gas into the solution may be performed.

Properties of the internally cross-linked polypeptides and modified polypeptides of the invention can be assayed, for example, using the methods described below. For example, any of the cross-linked polypeptides and polypeptides described herein can be tested for their ability to prevent or decrease stress-induced cell death (e.g., using methods described herein or known in the art) or to increase or induce cell death (e.g., apoptosis) (e.g., using fluorescence-assisted cell sorting, terminal deoxynucleotidyl transferase dUTP nick end labeling (TUNEL), and/or immunofluorescence microscopy, or any other methods known in the art for detecting cellular apoptosis or cell death).

Assays to Determine α-Helicity:

Internally cross-linked polypeptides or modified polypeptides are dissolved in an aqueous solution (e.g. 5 mM potassium phosphate solution at pH 7, or distilled $H_2O$, to concentrations of 25-50 µM). Circular dichroism (CD) spectra are obtained on a spectropolarimeter (e.g., Jasco J-710, Aviv) using standard measurement parameters (e.g. temperature, 20° C.; wavelength, 190-260 nm; step resolution, 0.5 nm; speed, 20 nm/sec; accumulations, 10; response, 1 sec; bandwidth, 1 nm; path length, 0.1 cm). The α-helical content of each internally cross-linked polypeptide or modified polypeptide is calculated by dividing the mean residue ellipticity by the reported value for a model helical decapeptide (see, e.g., Yang et al., *Methods Enzymol.* 130:208 (1986)).

Assays to Determine Melting Temperature (Tm):

Internally cross-linked polypeptides/modified polypeptides or the unmodified template peptides are dissolved in distilled $H_2O$ or other buffer or solvent (e.g., at a final concentration of 50 µM) and Tm is determined by measuring the change in ellipticity over a temperature range (e.g., 4 to 95° C.) on a spectropolarimeter (e.g., Jasco J-710, Aviv) using standard parameters (e.g., wavelength 222 nm; step resolution, 0.5 nm; speed, 20 nm/sec; accumulations, 10; response, 1 sec; bandwidth, 1 nm; temperature increase rate: 1° C./min; path length, 0.1 cm).

In Vitro Protease Resistance Assays:

The amide bond of the peptide backbone is susceptible to hydrolysis by proteases, thereby rendering peptidic compounds vulnerable to rapid degradation in vivo. Peptide helix formation, however, typically buries and/or twists and/or shields the amide backbone, and therefore may prevent or substantially retard proteolytic cleavage. The internally cross-linked polypeptides or modified polypeptides of the present invention may be subjected to in vitro enzymatic proteolysis (e.g., trypsin, chymotrypsin, and pepsin) to assess for any change in degradation rate compared to a corresponding uncross-linked or alternatively stapled polypeptide. For example, the internally cross-linked or modified polypeptide and a corresponding uncross-linked polypeptide are incubated with trypsin agarose and the reactions quenched at various time points by centrifugation and subsequent HPLC injection to quantitate the residual substrate by ultraviolet absorption at 280 nm. Briefly, the internally cross-linked polypeptide or modified polypeptide and the control uncross-linked polypeptide or alternatively stapled polypeptide (5 mcg) are incubated with trypsin agarose (Pierce) (S/E~125) for 0, 10, 20, 90, and 180 minutes. Reactions are quenched by tabletop centrifugation at high speed; remaining substrate in the isolated supernatant is quantified by HPLC-based peak detection at 280 nm. The proteolytic reaction displays first order kinetics and the rate constant, k, is determined from a plot of ln[S] versus time.

Internally cross-linked polypeptides or modified polypeptides and/or a corresponding uncross-linked polypeptide can be each incubated with fresh mouse, rat, and/or human serum (e.g. 1-2 mL) at 37° C. for, e.g., 0, 1, 2, 4, 8, and 24 hours. Samples of differing internally cross-linked polypeptide or modified polypeptide concentration may be prepared by serial dilution with serum. To determine the level of intact internally cross-linked polypeptide or modified polypeptide, the following procedure may be used: The samples are extracted, for example, by transferring 100 µL of sera to 2 mL centrifuge tubes followed by the addition of 10 µL of 50% formic acid and 500 µL acetonitrile and centrifugation at 14,000 RPM for 10 min at 4±2° C. The supernatants are then transferred to fresh 2-mL tubes and evaporated on Turbovap under $N_2$<10 psi, 37° C. The samples are reconstituted in 100 µL of 50:50 acetonitrile:water and submitted to LC-MS/MS analysis. Equivalent or similar procedures for testing ex vivo stability are known and may be used to determine stability of macrocycles in serum.

In Vivo Protease Resistance Assays:

A key benefit of peptide stapling is the translation of in vitro protease resistance into markedly improved pharmacokinetics in vivo. Liquid chromatography/mass spectrometry-based analytical assays can be used to detect and quantitate the levels of internally cross-linked polypeptides or modified polypeptides in plasma. For pharmacokinetic analysis, internally cross-linked polypeptides or modified polypeptides are dissolved in sterile aqueous 5% dextrose (1 mg/mL) and administered to C57BL/6 mice (Jackson Laboratory) by bolus tail vein or intraperitoneal injection (e.g., 5, 10, 25, or 50 mg/kg). Blood is collected by retro-orbital puncture at 5, 30, 60, 120, and 240 minutes after dosing 5 animals at each time point. Plasma is harvested after centrifugation (2,500×g, 5 minutes, 4° C.) and stored at −70° C. until assayed. Peptide concentrations in plasma are determined by reversed-phase high performance liquid chromatography with electrospray ionization mass spectrometric detection (see, e.g., Aristoteli et al., *Journal of Proteome Res.* 6:571-581, 2007; Walden et al., *Analytical and Bioanalytical Chemistry* 378:883-897, 2004). Study samples are assayed together with a series of 7 calibration standards of internally cross-linked polypeptide or modified polypeptide in plasma at concentrations ranging from 1.0 to 50.0 µg/mL, drug-free plasma assayed with and without addition of an internal standard, and 3 quality control samples (e.g., 3.75, 15.0, and 45.0 µg/mL). Standard curves are constructed by plotting the analyte/internal standard chromatographic peak area ratio against the known internally cross-linked polypeptide or modified polypeptide concentration in each calibration standard. Linear least squares regression is performed with weighting in proportion to the reciprocal of the analyte concentration normalized to the number of calibration standards. Values of the slope and y-intercept of the best-fit line are used to calculate the internally cross-linked polypeptide or modified polypeptide in study samples. Plasma concentration-time curves are analyzed by standard noncompartmental methods using WinNonlin Professional 5.0 software (Pharsight Corp., Cary, N.C.), yielding pharmacokinetic parameters such as initial and terminal phase plasma half-life, peak plasma levels, total plasma clearance, and apparent volume of distribution.

In Vitro Binding Assays:

To assess the binding and affinity of internally cross-linked polypeptides or modified polypeptides to proteins (e.g., IP3R1), a fluorescence polarization assay (FPA) can be used, for example. The FPA technique measures the molecular orientation and mobility using polarized light and fluorescent tracer. When excited with polarized light, fluorescent tracers (e.g., FITC) attached to molecules with high apparent molecular weights (e.g., FITC-labeled internally cross-linked polypeptides or modified polypeptides bound to a large protein) emit higher levels of polarized fluorescence due to their slower rates of rotation as compared to fluorescent tracers attached to smaller molecules (e.g., FITC-labeled internally cross-linked polypeptides or modified polypeptides that are free in solution).

In Vitro Displacement Assays to Characterize Antagonists of Peptide-Protein Interactions:

To assess the binding and affinity of compounds that antagonize the interaction between an internally cross-linked polypeptide or modified polypeptide and a protein (e.g., IP3R1 protein), a fluorescence polarization assay (FPA) utilizing a fluoresceinated internally cross-linked polypeptide or modified polypeptide is used, for example. The FPA technique measures the molecular orientation and mobility using polarized light and fluorescent tracer. When excited with polarized light, fluorescent tracers (e.g., FITC) attached to molecules with high apparent molecular weights (e.g. FITC-labeled internally cross-linked polypeptides or modified polypeptides bound to a large protein (e.g., IP3R1 protein) emit higher levels of polarized fluorescence due to their slower rates of rotation as compared to fluorescent tracers attached to smaller molecules (e.g. FITC-labeled internally cross-linked polypeptides or modified polypeptides that are free in solution). A compound that antagonizes the interaction between the fluoresceinated internally cross-linked polypeptide or modified polypeptide and an acceptor protein will be detected in a competitive binding FPA experiment.

Binding Assays in Intact Cells:

It is possible to measure binding of peptides or internally cross-linked polypeptides or modified polypeptides to proteins (e.g., a IP3R1 protein) on or in intact cells by immunoprecipitation experiments.

Cellular Penetrability Assays:

To measure the cell penetrability of the internally cross-linked polypeptides or modified polypeptides, intact cells are incubated with fluoresceinated internally cross-linked polypeptides (10 µM) for 4 hours in serum-free media or in media supplemented with human serum at 37° C., washed twice with media and incubated with trypsin (0.25%) for 10 minutes at 37° C. The cells are washed again and resuspended in PBS. Cellular fluorescence is analyzed, for example, by using either a FACSCalibur flow cytometer or Cellomics KineticScan® HCS Reader.

Clinical Trials:

To determine the suitability of the internally cross-linked polypeptides, modified polypeptides, compounds, or pharmaceutical compositions of the invention for treatment of humans, clinical trials can be performed. For example, patients having a cancer or suspected of having a cancer requiring chemotherapy are selected and separated into treatment and one or more control groups, wherein the treatment group is administered an internally cross-linked polypeptide, modified polypeptide, compound, or pharmaceutical composition of the invention, while the control groups receive a placebo or a known cytoprotective drug. The treatment safety and efficacy of the internally cross-linked polypeptides, modified polypeptides, compounds, or pharmaceutical compositions of the invention can thus be evaluated by performing comparisons of the patient groups with respect to factors, such as prevention of symptoms, time to resolution of symptoms, and/or time to a decrease in the number, severity, or frequency of one or more symptoms of the disease. In some embodiments, subject administered an internally cross-linked polypeptide, modified polypeptide, compound, or pharmaceutical composition of the invention can have a reduced number of symptoms of the disease as compared to a subject in a control group receiving a placebo.

Pharmaceutical Compositions

One or more of the proteins, polypeptides, or internally cross-linked polypeptides or modified polypeptides disclosed herein (e.g., one or more bclw mimetics, or bclw protein or BH4 domain-containing fragment thereof, or a polypeptide having an amino acid sequence at least 40%, 45%, 50%, 55%, 60%, 65%, 70%, 75%, 80%, 85%, 90%, 95% or 100% identical to the amino acid sequence (e.g., the IP3R1 or Bax-interacting alpha helical face of the BH4 domain of bclw) can be formulated for use as or in pharmaceutical compositions. Such compositions can be formulated or adapted for administration to a subject via any route, e.g., any route approved by the Food and Drug Administration (FDA). Exemplary methods are described in the FDA Data Standards Manual (available at www.fda.gov/Drugs/DevelopmentApprovalProcess/FormsSubmissionRequirements/ElectronicSubmissions/DataStandardsManualmonographs/default.htm). For example, compositions can be formulated or adapted for administration by inhalation (e.g., oral and/or nasal inhalation (e.g., via nebulizer or spray)), injection (e.g., intravenously, intra-arterial, subdermally, intraperitoneally, intramuscularly, and/or subcutaneously), and/or for oral administration, transmucosal administration, and/or topical administration (including topical creams or ointments, topical (e.g., nasal) sprays, and/or topical solutions).

In some instances, pharmaceutical compositions can include an effective amount of one or more internally cross-linked polypeptides or modified polypeptides (e.g., an internally cross-linked polypeptide having the BH4 domain of bclw). The terms "effective amount" and "effective to treat," as used herein, refer to an amount or a concentration of one or more internally cross-linked polypeptides and/or modified polypeptides or a pharmaceutical composition described herein utilized for a period of time (including acute or chronic administration and periodic or continuous administration) that is effective within the context of its administration for causing an intended effect or physiological outcome (e.g., prevention or treatment of CIPN and/or hearing loss).

Pharmaceutical compositions of this invention can include one or more internally cross-linked polypeptides and/or modified polypeptides and any pharmaceutically acceptable carrier, adjuvant and/or vehicle. In some instances, pharmaceutical compositions can further include one or more additional therapeutic agents in amounts effective for achieving a modulation of disease or disease symptoms.

In some instances, some pharmaceutical compositions of the present disclosure can include one or more agents for the alleviation of symptoms of a disorder described herein (e.g., agents for the alleviation of symptoms of CIPN or hearing loss).

In some instances, the pharmaceutical compositions of the present disclosure can include metformin. In some instances, the pharmaceutical compositions of the present disclosure can include one or more calpain inhibitors (e.g., AK275, MDL28170 (calpain inhibitor III, CAS 88191-84-8), PD150606, SJA6017, ABT-705253, and SNJ-1945).

The term "pharmaceutically acceptable carrier" refers to a carrier that can be administered to a patient, together with one or more internally cross-linked polypeptides and/or modified polypeptides of this invention, and which does not destroy the pharmacological activity thereof and is nontoxic when administered in doses sufficient to deliver a therapeutic amount of the one or more internally cross-linked polypeptide and/or one or more modified polypeptide.

Pharmaceutically acceptable carriers and vehicles that can be used in the pharmaceutical compositions of this invention include, but are not limited to, ion exchangers, alumina, aluminum stearate, lecithin, self-emulsifying drug delivery systems (SEDDS), such as d-α-tocopherol polyethyleneglycol 1000 succinate, surfactants used in pharmaceutical dosage forms such as Tweens or other similar polymeric delivery matrices, serum proteins (e.g., human serum albumin), buffer substances (e.g., phosphates, glycine, sorbic acid, potassium sorbate, partial glyceride mixtures of saturated vegetable fatty acids, water, and salts), and electrolytes (e.g., protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat). Cyclodextrins (e.g., α-, β-, and γ-cyclodextrin) can also be advantageously used to enhance delivery of the internally cross-linked polypeptides and/or modified polypeptides described herein.

The pharmaceutical compositions of this invention can contain any conventional nontoxic pharmaceutically-acceptable carriers, adjuvants, or vehicles. In some cases, the pH of the formulation can be adjusted with pharmaceutically acceptable acids, bases, or buffers to enhance the stability of the formulated internally cross-linked polypeptide(s) and/or modified polypeptide(s), or its delivery form. The term "parenteral" as used herein includes subcutaneous, intracutaneous, intra-venous, intra-muscular, intra-articular, intra-arterial, intra-synovial, intra-sternal, intra-thecal, intra-lesional, and intra-cranial injection or infusion techniques.

Pharmaceutical compositions can be in the form of a solution, powder for inhalation and/or nasal administration, or cream or spray for topical administration. Such compositions can be formulated according to techniques known in the art using suitable dispersing or wetting agents (such as, for example, Tween 80) and suspending agents.

Pharmaceutical compositions can include preservatives and additives. Preservatives can be included to limit or prevent microbial growth or contamination. Exemplary preservatives can include, but are not limited to, thimerosal, benzethonium chloride (Phemerol), phenol, and 2-phenoxy-ethanol. Exemplary additives can include human serum albumin, gelatin, and antibiotics.

In some instances, one or more of the internally cross-linked polypeptides and/or modified polypeptides disclosed herein can be conjugated, for example, to a carrier protein. Such conjugated compositions can be monovalent or multivalent. For example, conjugated compositions can include one internally cross-linked polypeptide or modified polypeptide disclosed herein conjugated to a carrier protein. Alternatively, conjugated compositions can include two or more internally cross-linked polypeptides or modified polypeptides disclosed herein conjugated to a carrier. In such instances, additional cytoprotective components or chemotherapeutic agents can also be coupled to the carrier protein.

As used herein, when two entities are "conjugated" to one another, they are linked by a direct or indirect covalent or non-covalent interaction. In certain aspects, the association is covalent. In other aspects, the association is non-covalent. Non-covalent interactions include hydrogen bonds, van der Waals interactions, hydrophobic interactions, magnetic interactions, electrostatic interactions, etc. An indirect covalent interaction is when two entities are covalently connected, optionally through a linker group.

Carrier proteins can include any protein that increases or enhances the cytoprotective activity of a pharmaceutical composition in a subject. Polymeric carriers can be a natural or a synthetic material containing one or more primary and/or secondary amino groups, azido groups, or carboxyl groups. Carriers can be water-soluble.

In some aspects, the present disclosure provides methods for using these pharmaceutical compositions for treating or preventing the CIPN or hearing loss.

Although effective amounts can depend, among other things, on the species of subject treated, the body weight of the subject, and the chosen treatment regimen, effective amounts can be readily determined by those in the art.

Methods of Treatment of Chemotherapy-Induced Peripheral Neuropathy

Chemotherapy is typically used in the context of cancer treatment and uses one or more anti-cancer drugs referred to as chemotherapeutic agents as part of a standardized treatment regimen. Chemotherapy may be given with a curative intent (which almost always involves combinations of drugs), or it may aim to prolong life or to reduce symptoms (palliative chemotherapy).

Non-limiting examples of chemotherapeutic agents include: alkylating agents (e.g., mechlorethamine, chlorambucil, cyclophosamide, ifosfamide, melphalan, streptozocin, carmustine, lomustine, oxaliplatin, busulfan, dacarbazine, temozolomide, thiotepa, and altretamine), antimetabolites (e.g., 5-fluorouracil, capecitabine, 6-mercaptopurine, folic acid analogs (e.g., methotrexate), gemcitabine, arabinosides (e.g., cytarabine), fludarabine, and premetrexed), anthracyclines (e.g., daunorubicin, doxorubicin, epirubicin, and idarubicin), topoisomerase inhibitors (e.g., topotecan, irinotecan, and epipodophyllotoxins (e.g., etoposide and teniposode)), microtubule-targeting agents and spindle poisons (e.g., taxanes (paclitaxel and docetaxel), vinblastine, vincristine, vindesine, vinorelbine, vinflunine, discodermolide, eleutherobin, sarcodictyin, epothilone, ixaberpilone, colchicine, combretastatin, 2-methoxyestradiol, noscapine, and estramustine), proteasome inhibitors, EGF-R inhibitors, Eph-R inhibitors, p38/JAK kinase inhibitors, PI3K inhibitors, MEK inhibitors, MAPK inhibitors, Trk inhibitors, proteasome inhibitors, Raf inhibitors, corticosteroids (e.g., dexamethasone, prednisolone, and methyl prednisolone), platinum compounds, and therapeutic antibodies (e.g., bevacizumab, brentuximab vedotin, cetuximab, ibritumomab tiuxetan, ipilimumab, panitumumab, rituximab, tositumomab, and trastuzumab). Chemotherapy often produces several side-effects.

Chemotherapy-induced peripheral neuropathy (CIPN), a type of chemotoxic axon injury, is a common and dose-limiting side effect of numerous cytotoxic chemotherapies in oncology. CIPN constitutes a frequent cause of axon injury and neurological impairment. Patients with CIPN experience pain, tingling, numbness, and/or impaired motor function, due to degeneration of long peripheral sensory or motor neuron axons.

Chemotherapeutic drugs that result in CIPN include microtubule-targeting agents. e.g., CIPN can result from use of chemotherapeutic agents such as, but not limited to, taxanes (e.g., paclitaxel, docetaxel), vinca alkaloids (e.g., vinblastine, vinorelbine, vindesine, vinflunine, vincristine) alkylating agents, arabinosides, proteasome inhibitors, PI3K inhibitors, Raf inhibitors, discodermolide, eleutherobin, sarcodictyin, epothilone, colchicine, combretastatin, 2-methoxyestradiol, and noscapine. Microtubule-targeting chemotherapeutic agents (e.g., those used to treat breast, ovarian, and lung cancers) cause a primarily sensory neuropathy. The mechanism for the chemotherapy-induced degeneration is not understood, and there are currently no treatments available for this common disorder.

This disclosure shows that microtubule targeting chemotherapeutic agents reduce axonal expression of bclw, but does not alter expression of the closely related components Bcl2 or $Bclx_L$. bclw was shown to protect axons from degeneration, and microtubule-targeting drugs such as paclitaxel cause degeneration by discontinuing this protection by lowering axonal levels of bclw. The BH4 domain of bclw is sufficient to reduce or prevent axonal degeneration. Accordingly, bclw protein or BH4 containing bclw polypeptides as well as bclw mimetics provide a clinically useful therapy for CIPN.

The disclosure includes methods of using an effective amount of one or more of the mimetics, polypeptides, or pharmaceutical compositions described herein (e.g., one or more bclw mimetics or polypeptides having an amino acid sequence at least 70% to 100% identical to the amino acid sequence of the BH4 domain of bclw) for the prevention or treatment of CIPN in a subject in need thereof. In some instances, the methods involve administering a bclw protein or a BH4 domain-containing fragment thereof. In some cases, the BH4 domain-containing bclw fragment is 15 16, 17, 18, 19, 20, 21, 22, 23, 24, or 25 amino acids in length. In some instances, the methods involve administering a bclw polypeptide comprising or consisting of an amino acid sequence set forth in SEQ ID NOs.: 2 or 3. In some cases, the bclw polypeptide is 15 16, 17, 18, 19, 20, 21, 22, 23, 24, or 25 amino acids in length. In some cases, the bclw polypeptide comprises or consists of an amino acid sequence set forth in SEQ ID NOs.: 2 or 3 with one to twelve amino acid substitutions (e.g., 1, 2, 3, 4, 5) and/or one to five amino acid deletions (e.g., 1, 2, 3 at the N or C-terminal of the polypeptide). In some cases, the bclw polypeptide is 5, 6, 7, 8, 9, 10, 11, 12, 13, 14, 15 16, 17, 18, 19, 20, 21, 22, 23, 24, or 25 amino acids in length. In some instances, the methods involve administering a bclw mimetic comprising or consisting of any one of the amino acid sequences set forth in SEQ ID NOs. 4 to 32 or 50-53. In certain instances, the methods involve administering a bclw mimetic comprising or consisting of any one of the amino acid sequences set forth in SEQ ID NOs. 4 to 32 or 50-53 except for 1, 2, 3, 4, or 5 amino acid substitutions and/or deletions (e.g., at N or C-terminus; IP3R non-interacting alpha helical face; Bax non-interacting alpha helical face). The method can further comprise administering other therapeutically beneficial agents to the subject. For example, metformin and/or one or more calpain inhibitors can be administered before, during, and/or after administration of the bclw mimetics, bclw polypeptides, or pharmaceutical compositions described herein.

The term "subject," as used herein, refers to any mammal. In certain aspects, the term "subject," as used herein, refers to a human (e.g., a man, a woman, or a child).

The terms "administer," "administering," or "administration," as used herein refers to implanting, absorbing, ingesting, injecting, or inhaling, one or more of the inventive internally cross-linked polypeptides, modified polypeptides, or pharmaceutical compositions (e.g., any of those described herein). In some instances, one or more of the internally cross-linked polypeptides, modified polypeptides, compounds, or pharmaceutical compositions disclosed herein can be administered to a subject topically and/or orally. For example, the methods herein include administration of an effective amount of one or more internally cross-linked polypeptides, modified polypeptides, compounds, or pharmaceutical compositions to achieve the desired or stated effect. The internally cross-linked polypeptides, modified polypeptides, compounds, and pharmaceutical compositions of this invention can be administered at least once a week (e.g., about twice a week, about three times a week, about four times a week, about five times a week, about six times a week, or about 1 to about 6 times per day) or alternatively, as a continuous infusion. Such administration can be used as a chronic or acute therapy.

Specific dosage and treatment regimens for any particular patient will depend upon a variety of factors, including the activity of the specific internally cross-linked polypeptide, modified polypeptide, or compound employed, the age, body weight, general health status, sex, diet, time of administration, rate of excretion, drug combination, the severity and course of the CIPN, the patient's disposition to the treatment, and the judgment of the treating physician.

Following administration, the subject can be evaluated to detect, assess, or determine the number of symptoms and/or the severity and/or frequency of one or more symptoms of the CIPN in the subject. In some instances, treatment can continue until a reduction in the number of symptoms and/or the severity and/or frequency of one or more symptoms of CIPN is observed. Upon improvement of a patient's condition, a maintenance dose of a mimetic, polypeptide, or pharmaceutical composition, or a combination thereof, of the disclosure can be administered, if necessary. Subsequently, the dosage or frequency of administration, or both, can be reduced, as a function of the symptoms, to a level at which the improved condition is retained. Patients can, however, require intermittent treatment on a long-term basis upon any recurrence of CIPN.

Methods of Administering Chemotherapy

Also provided are methods of administering chemotherapy to a subject in need thereof. The method involves administering the chemotherapy and an effective amount of one or more of the bclw mimetics, bclw polypeptides, or pharmaceutical compositions described herein to the subject. The chemotherapeutic agents and the mimetics, polypeptides, or pharmaceutical compositions can be administered simultaneously or sequentially (e.g. the chemotherapeutic agents can be administered prior to or after the bclw mimetics, bclw polypeptides, or pharmaceutical compositions). In certain instances the chemotherapeutic agent is selected from the group consisting of a microtubule-targeting agent, an alkylating agent, an antimetabolite, a folic acid analogue, a spindle poison, a platinum compound, an epipodophyllotoxin, an antibiotic, an EGF-R inhibitor, an Eph-R inhibitor, a p38/JAK kinase inhibitor, a PI3K inhibitor, a MEK inhibitor, a MAPK inhibitor, a Trk inhibitor, a proteasome inhibitor, and a Raf inhibitor. In some instances, the subject is administered an additional therapeutic agent. For example, metformin and/or one or more calpain inhibitors can be administered before, during, and/or after administration of the chemotherapeutic agents and/or the bclw mimetics, bclw polypeptides, or pharmaceutical compositions. In some cases, the subject being administered chemotherapy has a hematological tumor (e.g., acute myeloid leukemia, chronic myeloid leukemia, Hodgkin lymphoma, non-Hodgkin lymphoma, multiple myeloma, acute lymphoblastic leukemia, or chronic lymphocytic leukemia). In certain instances, the subject being administered chemotherapy has a breast cancer, ovarian cancer, or lung cancer. In some instances, the methods involve administering a bclw protein or a BH4 domain-containing fragment thereof. In some cases, the BH4 domain-containing bclw fragment is 5, 6, 7, 8, 9, 10, 11, 12, 13, 14, 15 16, 17, 18, 19, 20, 21, 22, 23, 24, or 25 amino acids in length. In some instances, the methods involve administering a bclw polypeptide comprising or consisting of an amino acid sequence set forth in SEQ ID NOs.: 2 or 3. In some cases, the bclw polypeptide is 5, 6, 7, 8, 9, 10, 11, 12, 13, 14, 15 16, 17, 18, 19, 20, 21, 22, 23, 24, or 25 amino acids in length. In some cases, the bclw polypeptide comprises or consists of an amino acid sequence set forth in SEQ ID NOs.: 2 or 3 with one to twelve amino acid substitutions (e.g., 1, 2, 3, 4, 5) and/or one to five amino acid deletions (e.g., 1, 2, 3 at the N or C-terminal of the polypeptide). In some cases, the bclw polypeptide is 15 16, 17, 18, 19, 20, 21, 22, 23, 24, or 25 amino acids in length. In some instances, the methods involve administering a bclw mimetic comprising or consisting of any one of the amino acid sequences set forth in SEQ ID NOs. 4 to 32, or 50-53. In certain instances, the methods involve administering a bclw mimetic comprising or consisting of any one of the amino acid sequences set forth in SEQ ID NOs. 4 to 32 or 50-53, except for 1, 2, 3, 4, or 5 amino acid substitutions and/or deletions (e.g., at N or C-terminus).

Methods for Selecting a Subject for Treatment with a BclW Protein, Polypeptide, or Mimetic Also provided are methods of selecting or identifying a subject at risk of developing CIPN. The selected subjects can then be treated using any of the above-described methods. The subjects can be identified or selected on the basis of one or more of the following criteria: having reduced levels of endogenous bclw in the axons of the sensory neurons relative to a control subject who does not develop CIPN upon administration of a chemotherapeutic agent (e.g., a taxane such as paclitaxel), reduced levels of EphA4 or Eph/5 receptors in sensory neurons relative to a control subject who does not develop CIPN upon administration of a chemotherapeutic agent (e.g., a taxane such as paclitaxel), reduced expression of transporters relative to a control subject who does not develop CIPN upon administration of a chemotherapeutic agent (e.g., a taxane such as paclitaxel), reduced expression of tubulin relative to a control subject who does not develop CIPN upon administration of a chemotherapeutic agent (e.g., a taxane such as paclitaxel), reduced expression of NGF, BDNF, and/or NT3 relative to a control subject who does not develop CIPN upon administration of a chemotherapeutic agent (e.g., a taxane such as paclitaxel); and/or genetic polymorphisms in or adjacent to genes such as EphA4/5 that may confer increased risk, or in the genes encoding calcium-interacting proteins such as calmodulin and parvalbumin. Subjects meeting one or more of these criteria are determined to have an enhanced risk of developing CIPN.

Methods for Treating Hearing Loss

This disclosure also features methods of treating or preventing hearing loss in a subject in need thereof. The examples provided in this disclosure show that bclw is necessary for the maintenance of hearing during aging. Accordingly, administering bclw or a mimetic thereof is useful for treating or preventing hearing loss. The hearing loss may be, e.g., age-related, noise-induced, or chemotherapy-induced.

In some instances, the methods involve administering a bclw protein or a BH4 domain-containing fragment thereof. In some cases, the BH4 domain-containing bclw fragment is 5, 6, 7, 8, 9, 10, 11, 12, 13, 14, 15 16, 17, 18, 19, 20, 21, 22, 23, 24, or 25 amino acids in length. In some instances, the methods involve administering a bclw polypeptide comprising or consisting of an amino acid sequence set forth in SEQ ID NOs.: 2 or 3. In some cases, the bclw polypeptide is 5, 6, 7, 8, 9, 10, 11, 12, 13, 14, 15 16, 17, 18, 19, 20, 21, 22, 23, 24, or 25 amino acids in length. In some cases, the bclw polypeptide comprises or consists of an amino acid sequence set forth in SEQ ID NOs.: 2 or 3 with one to twelve amino acid substitutions (e.g., 1, 2, 3, 4, 5) and/or one to five amino acid deletions (e.g., 1, 2, 3 at the N or C-terminal of the polypeptide). In some cases, the bclw polypeptide is 5, 6, 7, 8, 9, 10, 11, 12, 13, 14, 15 16, 17, 18, 19, 20, 21, 22, 23, 24, or 25 amino acids in length. In some instances, the methods involve administering a bclw mimetic comprising or consisting of any one of the amino acid sequences set forth in SEQ ID NOs. 4 to 32 or 50-53. In certain instances, the methods involve administering a bclw mimetic comprising or consisting of any one of the amino acid sequences set forth in SEQ ID NOs. 4 to 32 or 50-53, except for 1, 2, 3, 4, or 5 amino acid substitutions and/or deletions (e.g., at N or C-terminus). In certain instances, the protein, polypeptide, or mimetic is administered by injection (e.g., into the oval window).

Subjects for this treatment can be selected on the basis of having an advanced age (e.g., age greater than or equal to 65, 70, 75, 80, 85, 90, 95, or 100) and/or hearing loss (e.g., hearing thresholds greater than or equal to 25, 30, 35, 40, 45, 50, 55, 60, 65, 70, 75, 80, or 85 db, as evaluated by standard clinical methods known in the art, e.g., pure tone audiometry for air conduction thresholds at 500, 1000, and 2000 Hz).

In general, these methods include selecting a subject and administering to the subject an effective amount of one or more of the mimetics, polypeptides, or pharmaceutical compositions described herein, and optionally repeating administration as required for the treatment of hearing loss.

The terms "administer," "administering," or "administration," as used herein refers to implanting, absorbing, ingesting, injecting, or inhaling, one or more of the inventive internally cross-linked polypeptides, modified polypeptides, or pharmaceutical compositions (e.g., any of those described herein). In some instances, one or more of the internally cross-linked polypeptides, modified polypeptides, compounds, or pharmaceutical compositions disclosed herein can be administered to a subject by injection (e.g., into the oval window). In some instances, one or more of the internally cross-linked polypeptides, modified polypeptides, compounds, or pharmaceutical compositions disclosed herein can be administered to a subject by direct delivery via the tympanic membrane. In certain instances, the administration involves the use of a virus (e.g., adenovirus, adeno-associated virus, lentivius vectors) or using ear drops. For example, the methods herein include administration of an effective amount of one or more internally cross-linked polypeptides, modified polypeptides, compounds, or pharmaceutical compositions to achieve the desired or stated effect. The internally cross-linked polypeptides, modified polypeptides, compounds, and pharmaceutical compositions of this invention can be administered at least once a week (e.g., about twice a week, about three times a week, about four times a week, about five times a week, about six times a week, or about 1 to about 6 times per day) or alternatively, as a continuous infusion. Such administration can be used as a chronic or acute therapy.

Specific dosage and treatment regimens for any particular patient will depend upon a variety of factors, including the activity of the specific internally cross-linked polypeptide, modified polypeptide, or compound employed, the age, body weight, general health status, sex, diet, time of administration, rate of excretion, drug combination, the severity of the hearing loss, the patient's disposition to the treatment, and the judgment of the treating physician.

Following administration, the subject can be evaluated to assess the hearing loss in the subject. In some instances, treatment can continue until hearing of the subject improves. Upon improvement of a patient's condition, a maintenance dose of a mimetic, polypeptide, or pharmaceutical composition, or a combination thereof, of the disclosure can be administered, if necessary. Subsequently, the dosage or frequency of administration, or both, can be reduced, as a function of the hearing capacity of the subject, to a level at which the improved condition is retained. Patients can, however, require intermittent treatment on a long-term basis upon any recurrence of hearing loss.

The following are examples of the practice of the invention. They are not to be construed as limiting the scope of the invention in any way.

EXAMPLES

Example 1: Materials & Methods for Examples 2-7

All experimental procedures were done in accordance with the National Institutes of Health (NIH) guidelines and were approved by the Dana-Farber Cancer Institutional Animal Care and Use Committee (IACUC).

Animal Use.

Timed pregnant Sprague-Dawley rats were from Charles River. bclw−/− mice are described in Ross et al., *Nat Genet.*, 18(3):251-6 (1998). Genotyping for the wild-type bclw gene and/or lacZ gene was performed by Transnetyx using the Bclw targeting sequence GCTCTGAACCTCCC-CATGACTTAAATCCGTTGCTCTTTCT-TGGCCCTGCCCAGTGCCTCTGAGCATTTCACC-TATCTCAGGAGC (SEQ ID NO:37) and the lacZ sequence CGATCGTAATCACCCGAGTGTGAT-CATCTGGTCGCTGGGGAATGAGTCAGGCCACG-G (SEQ ID NO:38). Bclw mice were maintained on a C57Bl6EJ background.

Cell Culture.

Compartmented chamber (Campenot) cultures were prepared as described (see, e.g., Fenstermacher et al., *Springer Protocols: Neuromethods,* 103:105-124 (2015)), with modifications. Briefly, DRGs from embryonic day 15 (E15) rats of either sex were dissected and trypsinized. DRGs ($1.2\times10^5$ cells) were plated in the center compartment of a Teflon divider (Camp10, Tyler Research; Campenot, 1982) affixed to a p35 culture dish coated with growth factor reduced Matrigel basement membrane (BD Biosciences) 1:45 in DMEM. Cultures were maintained in media consisting of Neurobasal (Invitrogen) with 2% B27 supplement (Invitrogen), 1% penicillin-streptomycin, 1% GlutaMAX (Life Technologies), 0.08% glucose, and 0.3 µM cytosine arabinoside (AraC) at 37° C., 7.5% $CO^2$; BDNF+NGF (Pepro-Tech) were added to the cell body compartment at a concentration of 10 ng/ml and to the axon compartment at a concentration of 100 ng/ml for 2d. On day 3, media was replaced and the AraC was omitted. On day 5, neurotrophins were removed from the cell body compartment and reduced to 1 ng/ml in the axon compartments for 3-5 days. For paclitaxel treatment experiments, 30 µM paclitaxel (Sigma-Aldrich) or vehicle control (0.1% DMSO) was added to either cell body or distal axon compartments on day 7 for 24 hours. For calpain inhibition experiments, 20 µM calpain inhibitor III (VWR) and paclitaxel were added simultaneously to distal axon compartment.

Microfluidic chambers cultures were prepared as described (see, e.g., Fenstermacher et al., *Nature Neuroscience,* 19:690-696 (2016)), with modifications. Briefly, $3\times10^4$ E15 DRG neurons (4 µl volume) were plated into one channel of a microfluidic device (Xona Microfluidics, SND450) affixed to a PDL/laminin-coated cover glass (Fisherbrand Microscope Cover Glass; 24×40-1.5). Cells were plated in media with 0.3 µM AraC; 50 ng/mL NGF+BDNF was added to cell body wells, and 100 ng/ml was added to axon wells. On day 2, cell body neurotrophins were reduced to 10 ng/ml. On day 4, cell body neurotrophins were reduced to 1 ng/ml and axon neurotrophins were reduced to 10 ng/ml. For paclitaxel treatment experiments, 60 µM paclitaxel or 0.1% DMSO vehicle control was added on day 5 to axon wells for 48 hours. Cells were fixed at room temperature with 4% PFA diluted 1:2 in media for 10 min, then undiluted 4% PFA for an additional 10 min.

Mass cultures consisting of $3\times10^5$ E15 DRG neurons were grown on Matrigel-coated p35 culture dishes in neurotrophin-enriched (100 ng/ml NGF+BDNF) media with 0.3 µg/ml AraC. On day 3, neurotrophins were reduced to 10 ng/ml) and cultures maintained for 3-6 more days.

Axonal Degeneration Assay.

Compartmented chamber cultures were fixed at room temperature with 4% PFA diluted 1:2 in media for 10 min, then undiluted 4% PFA for an additional 20 min. Cultures were permeabilized with 0.1% TritonX-100 for 10 min, blocked in 3% BSA and 0.1% Triton X-100 for 1 hour at room temperature, and incubated with mouse anti-Tuj1 (1:400; clone Tuj1; Covance) overnight at 4° C. Cultures were then incubated with goat anti-mouse AlexaFluor (1:1000; Invitrogen) for 1 hour at room temperature and counterstained with DAPI. Images of distal axon tips were obtained using a 40× air objective, and axonal degeneration was quantified as a degeneration index, as previously described (Cosker et al., Neuroscience, 33:5195-5207 (2013)). Apoptosis analysis was carried out on the same cultures by taking images in the cell body compartment and counting total and condensed nuclei in NIH ImageJ software by an observer blind to condition.

Western Blotting.

For analysis of Bcl2 family proteins, cell bodies and axons of E15 DRGs in compartmented cultures were lysed in nonionic detergent, lysates were separated by 4-12% Bis-Tris or 3-8% Tris-Acetate SDS-Page (Thermo Fisher Scientific), and probed with the following antibodies: anti-Bclw (1:1000; clone 31H4; Cell Signaling Technology), anti-Bcl2 (1:1000; Abcam), anti-Bclx$_L$ (1:1000; Cell Signaling Technology), and anti-GAPDH (1:2000; clone 14C10; Cell Signaling Technology). Bands were visualized with secondary antibodies conjugated to HRP (1:10,000; Bio-Rad) and SuperSignal chemiluminescent substrate signal. Using NIH ImageJ software, protein levels were quantified and levels of protein were normalized to GAPDH.

Calpain Protease Activity Luminescence Assay.

DRG neurons in mass cultures were treated with vehicle (0.1% DMSO for 48 h), paclitaxel (30 nM, 600 nM, or 1.2 µM for 48 hours), or calcium chloride (3 mM for 24 hours). Cultures were harvested in 1× Passive Lysis Buffer (Promega). The resulting lysate was spun 10,000×g for 5 min at 4° C., and 50 µL supernatant was combined with 50 µL Calpain-Glo Reagent (Promega) in a 96 well plate. The plate was shaken briefly and incubated for 40 min in the dark; luminescence intensity was measured with a microplate reader and normalized to protein concentration.

Tetramethylrhodamine Ethyl Ester Measurements of Mitochondrial Membrane Potential.

E15 DRG neurons in microfluidic devices were labeled using Tetramethylrhodamine ethyl ester (TMRE) (Invitrogen). TMRE was applied (10 nM) for 20 min at 37° C., then cells were rinsed with phenol-free media and imaged live using a 60× oil 1.4NA objective. Fluorescence intensity of axonal mitochondria was measured by dividing the fluorescence intensity of each mitochondria (Fm) by the background fluorescence intensity of a nearby cytoplasmic region (Fc). Fluorescence intensity was measured using NIH ImageJ software for 80 mitochondria per condition across three experiments, by an observer blind to condition.

Quantitative Reverse Transcription-PCR.

RNA was extracted from cultured neurons using TRIzol (Invitrogen) according to the manufacturer's protocol. Reverse transcription (RT) was performed using a cDNA archive kit (Applied Biosystems) according to the manufacturer's protocol. Quantitative real-time RT-PCR was performed using Taqman Gene expression assays (Applied Biosystems) to assess the expression of bclw (Rn00821025_g1), bcl2 (Rn99999125_m1), and bclx$_L$ (Rn00580568_g1). Data were normalized to gapdh (glyceraldehyde-3-phosphate dehydrogenase) for each sample (Applied Biosystems).

SAHB Generation.

FITC- or biotin-tagged stapled peptides corresponding to the BH4 domain of Bclw were synthesized, derivatized, and purified using our established methods (Bird et al., Nature, 455:1076-1081 (2008)). Stapled peptides were purified by LC-MS to >95% purity and quantified by amino acid analysis. Lyophilized SAHBs were reconstituted in 100% DMSO and diluted into aqueous buffers for experimentation.

Liposomal Release Assay.

Large unilamellar vesicles with lipid composition resembling the mitochondrial outer membrane were generated and entrapped with ANTS and DPX as described (see, e.g., Leshchiner et al., Proc Natl Acad Sci USA, 110:E986-95 (2013); Lovell et al., Cell, 135:1074-1084 (2008)). Recombinant BAX was generated in Bl-21 DE3 E. coli and then purified by affinity and size exclusion chromatography as described (see, e.g., Edwards et al., Chemistry & Biology, 20(7):888-902 (2013); Gavathiotis et al., Nature, 455:1076-1081 (2008)).

For measurement of BIMA2-induced activation of BAX, recombinant, full-length BAX protein, BIMA2 (amino acids 145-164), and BCLw BH4 SAHBs were added to liposomes (5 µl) at the indicated concentrations to a final volume of 30 µl in 384-well plate format. ANTS release and dequenching due to DPX dissociation (F) was measured over a period of 7200 sec with a Tecan M1000 plate reader (excitation and emission wavelengths of 355 and 520 nm, respectively). Plates were re-read following lysis with 1% Triton X-100 to determine maximal release (F100). Percent ANTS/DPX release was calculated as [(F−F0)/(F100−F0)].

Protein and Peptide Introduction.

Recombinant His-tagged Bclw, Bcl2, and Bclx$_L$ proteins (R&D Systems) or control β-galactosidase protein were introduced into cell bodies or axons of compartmented chamber cultures as described (e.g., Cosker et al., Nature Neuroscience, 19:690-696 (2016)). Briefly, 1 µg/µl protein was introduced into cultures using 2 µl Chariot reagent (Active Motif). To confirm expression of His-tagged proteins, cell bodies and axons were lysed in nonionic detergent, and protein lysates were separated as above and blotted with the following antibodies: anti-His (1:1000; Novagen) and anti-pan-actin (1:1000; Cell Signaling Technology). FITC-tagged SAHB peptides (BH4-Bclw, BH4-Bcl2, and BH4-Bclx$_L$; stock solutions 1 mM in DMSO) were introduced into cell bodies or axons using 350 ng peptide and 2 µl of Chariot reagent diluted 1:10 in water. Control was no peptide with 2 µl of 1:10 diluted Chariot. To confirm peptide expression, cultures were processed for axonal degeneration assay as above, and FITC immunofluorescence was examined with a 40× air objective. Paclitaxel was added to cultures 1 hour after protein or peptide transfection.

Neurotrophin Deprivation.

FITC SAHBs (FITC-BH4 Bclw, Bcl2, or Bclx$_L$) or no peptide control were transfected into the cell body compartment of compartmented cultures as described above. One hour later, both cell body and axon compartments were changed into media without NGF+BDNF for 24 hours. A non-transfected control culture was maintained in media with normal levels of NGF+BDNF. Cultures were fixed and incubated with DAPI (1:1000). Images were taken with a 40× air objective, and an observer blind to condition counted the number of total and condensed nuclei using NIH ImageJ software.

Biotinylated SAHB Pulldowns.

DRGs were grown in compartmented chamber cultures for 7-8 days, and cell bodies and axons were separately harvested in lysis buffer containing 1% CHAPS detergent, 150 mM NaCl, 50 mM Tris pH 7.4, 1 mM DTT, 500 mM NaF, 100 mM PMSF, 200 mM NaVO$_3$, and EDTA-free cOmplete Mini protease inhibitor cocktail (Sigma-Aldrich). Lysate was pre-cleared 2 hours at 4° C. with High Capacity Neutravidin Agarose Beads (1:20 in lysate; Thermo Scientific). For each pulldown, 200-600 µg of precleared lysate was incubated overnight at 4° C. with biotin alone or with biotinylated-BH4 peptides of Bclw, Bcl2, or Bclx$_L$ to a final peptide or biotin concentration of 20 µM. The next day, Neutravidin beads were added (1:14) to lysate for 2 hours at 4° C. Lysate was removed, beads were washed on ice with cold PBS+protease inhibitor cocktail, and sample was eluted by boiling for 5 minutes in nonionic lysis buffer, sample buffer, and reducing agent. Protein was resolved with either 4-12% Bis-Tris SDS-page (Bax, YARS, IP$_3$R1) or 3-8% Tris-Acetate SDS-page (YARS, IP$_3$R1) and probed with the following antibodies at 1:1000: anti-Bax (Cell Signaling), anti-YARS (tyrosyl tRNA synthetase; clone EPR9927; Abcam), and anti-IP3R1 (Thermo Scientific). A 10% input lane from the original cell body or axon lysate was run alongside pulldown lysate. Band intensity was quantified as described above, and each pulldown intensity was normalized to the input intensity.

shRNA Lentiviral Knockdown.

Lentiviral particles were generated using shRNA constructs from Sigma-Aldrich, and validated for protein knockdown in mass cultures. For degeneration assays, lentivirus expression shRNAs were added to compartmented cultures 1:1 in media for 24 hours, then media was changed and cultures were allowed to grow for 5 days prior to paclitaxel treatment. Bclw: TRCN0000321174, TRCN0000321104, TRCN0000321105, TRCN0000321106, TRCN0000004687
IP$_3$R1: TRCN0000321161, TRCN0000273767, TRCN0000012439, TRCN0000012440, TRCN0000012442
IP$_3$R3: TRCN0000434343, TRCN0000424063, TRCN0000416529, TRCN0000012444, TRCN0000012447

Paclitaxel Treatment and Behavioral Testing.

2 month old age-matched bclw−/− and bchw+/+ mice (17-30 g) of either sex were injected intraperitoneally (IP) with 4 mg/kg paclitaxel (Bristol-Myers Squibb) every other day for 8 days (4 total injections). Paclitaxel was prepared as 1 part 6 mg/ml paclitaxel stock solution diluted in vehicle (1:1 v/v Cremophor EL [EMD Millipore] and dehydrated ethanol) and 2 parts sterile saline and injected at 10 µl/g. Control mice were injected with 1 part vehicle and 2 parts saline. At 6 months of age, bclw−/− mice have altered noxious sensation; however, 2-3 month old bclw−/− mice exhibit normal motor function and noxious sensation (see, e.g., Courchesne et al., *Neuroscience*, 31:1624-1634 (2011)). For three days prior to the baseline testing, mice were weighed, trained on an automated RotaRod apparatus (4 rpm for 1 min without falling), and habituated in von Frey cages. The next two days, baseline behavioral performance was assessed and averaged. The first paclitaxel injection was given three days later, and mice were weighed and behaviorally tested 10 days after the final injection. To assay motor function, mice were placed on the RotaRod with a ramp of 4-40 rpm and 0.4 rpm/sec acceleration, and latency to fall was measured. Noxious mechanosensation threshold was assayed as described (see, e.g., Courchesne et al., 2011 (supra)), using von Frey filaments (0.008-1.4 g). Withdrawal threshold was determined to be the applied force at which the animal withdrew the stimulated paw on at least 2 of 10 applications. Noxious thermal sensation threshold was assayed as described (see, e.g., Courchesne et al., 2011 (supra)), using a 50° C. hot-plate and measuring latency to flick or lick the hindpaw. Mouse behavior was assessed by an experimenter blind to genotype and condition.

Epidermal Footpad Innervation.

Footpad tissue from hindpaws of bclw−/− and bclw+/+ mice was harvested, fixed, and sectioned (see, e.g., Cosker et al., 2013). Briefly, mice were euthanized with isoflurane 11 days after final paclitaxel injection and footpad tissue was removed and divided into thick (dermal papillae containing) and thin (non-dermal papillae containing) skin. Footpads were fixed in Zamboni's fixative overnight at 4° C., cryopreserved in 30% sucrose overnight at 4° C., frozen, and sectioned into 30 µm floating sections. Sections were blocked in 10% normal goat serum with 0.1% Triton X-100 in PBS 1 hour at room temperature and incubated with anti-Tuj1 (1:300; Covance) overnight at 4° C. Sections were then incubated with goat anti-mouse AlexaFluor 488 (1:200; Invitrogen) and DAPI (1:1000) for 2 hours at room temperature and mounted on gelatin-coated slides. Epidermal images were acquired on a Nikon Ni-E C2 confocal with a 40× 1.3NA oil objective as 30-35 µm z-stacks (1 µm step size) and converted into a maximum intensity projection image. Intraepidermal nerve fiber density was determined to be the number of Tuj1-positive fibers penetrating into the epidermis, normalized to the measured epidermal length (225 µm-450 µm per image) and displayed as number of Tuj1-positive fibers per 225 µm. Images were acquired and quantified in NIH ImageJ by an experimenter blind to condition.

Statistics.

Data are expressed as mean SEM. To assess statistical significant, data were analyzed by unpaired two-tailed Student's t test. For multiple comparisons, data were analyzed by one-way ANOVA with post hoc Bonferroni or Dunnett correction. Significance was placed at $p<0.05$ unless otherwise indicated.

Example 2: Paclitaxel Initiates an IP3R1-Dependent Axon Degenerative Cascade

To determine the site of action of paclitaxel on sensory neurons, paclitaxel (30 nM) was introduced into the media surrounding either the cell body or distal axon compartments of E15 DRG sensory neurons in compartmented cultures, and paclitaxel-induced axonal fragmentation, a direct readout of degeneration, was analyzed. Paclitaxel added to axons was found to increase axon degeneration, while paclitaxel added to cell bodies has no effect (FIGS. 1A and 1B). Notably, paclitaxel treatment of either subcellular compartment did not induce cell body apoptosis as assessed by nuclear condensation (FIGS. 1C and 1D). These results suggest that paclitaxel acts directly on sensory neuron axons, and indicate that paclitaxel acts locally on axons to induce degeneration.

Figure 2:
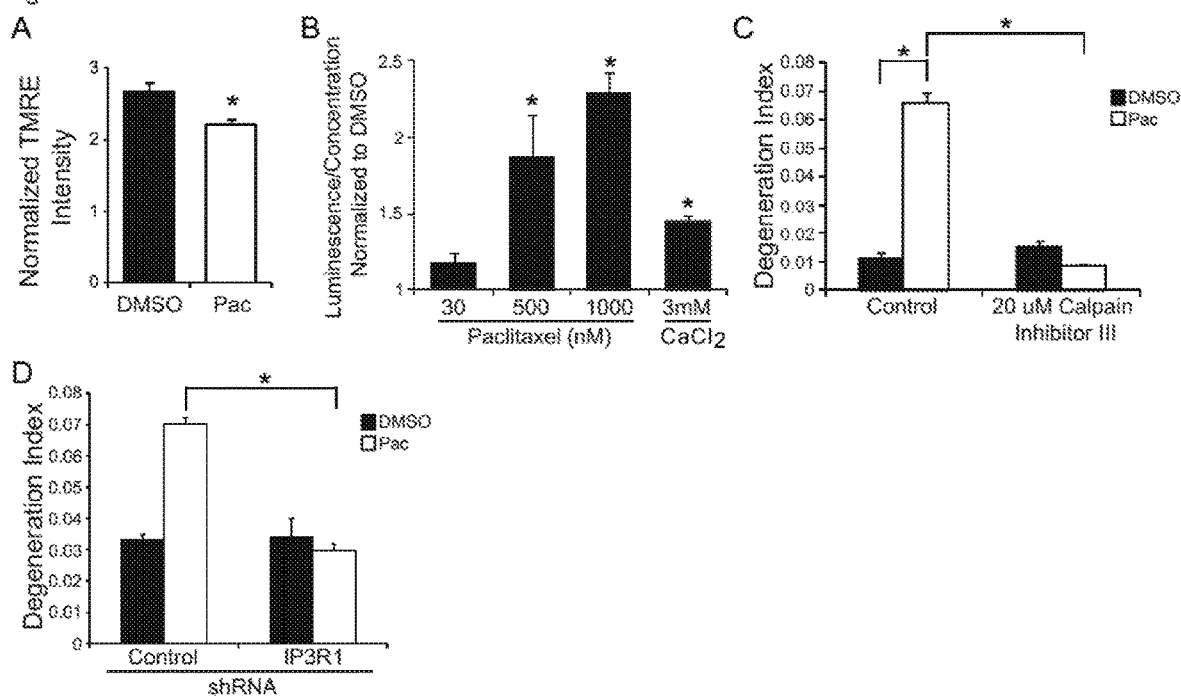
FIG. 2A is a bar graph providing the fluorescence intensity (Fm/Fc) of the voltage-sensitive dye TMRE in axons of DRG neurons in microfluidic cultures; DMSO or paclitaxel (Pac) added to distal axon compartment for 24 hours; *p<0.001 by Student's t-test; n=80 mitochondria across 3 experiments; data represents mean+SEM.
FIG. 2B is a bar graph depicting luminescence generated by calpain activity from DRG neurons treated for 48 hours with 30 nM, 500 nM, or 1000 nM paclitaxel or for 24 hours with 3 mM calcium chloride. Data normalized to DMSO control; *p<0.05 by one-way ANOVA with Bonferroni correction; data represents mean+SEM, n=3.
FIG. 2C is a bar graph showing the degeneration index of axons treated with DMSO or paclitaxel in the absence or presence of 20 µM calpain inhibitor III to axons; *p<0.05 by one-way ANOVA with Bonferroni correction; data represents mean+SEM, n=3.
FIG. 2D is a bar graph illustrating the degeneration index after 24-hour addition of paclitaxel or vehicle to axons following lentiviral infection with a control shRNA or an shRNA targeting $IP_3R1$; *p<0.05 by one-way ANOVA with Bonferroni correction; data represents mean+SEM, n=3.

Paclitaxel treatment reduced axonal mitochondrial membrane potential as assessed using the voltage-sensitive dye TMRE (FIG. 2A), and increased calpain activity in a dose-dependent manner (FIG. 2B). Furthermore, the calpain inhibitor III (20 µM to axons) prevented paclitaxel-induced degeneration, indicating that axon fragmentation requires local calpain activity (FIG. 2C). Knockdown of the type 1 inositol 1,4,5-trisphosphate receptor (IP$_3$R1) was found to prevent paclitaxel-induced degeneration, suggesting that paclitaxel causes degeneration through IP$_3$R1 (FIG. 2D). Together, these results indicate that axonal paclitaxel treatment activates a degenerative cascade involving IP3R1 and the protease calpain.

Example 3: Bclw Prevents Paclitaxel-Induced Degeneration

Figure 3:
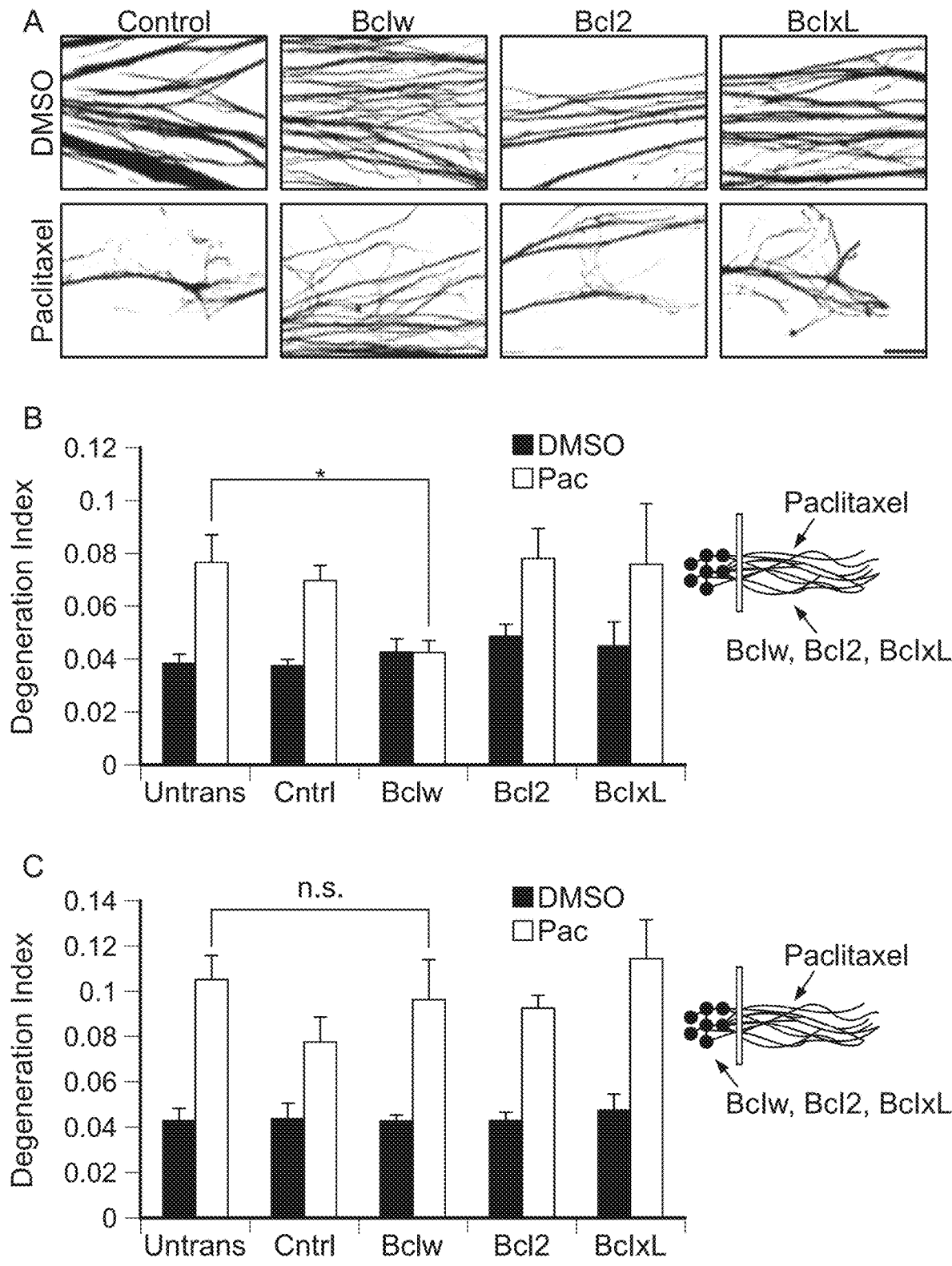
FIG. 3A shows binarized Tuj1 immunostaining of axons treated with DMSO or paclitaxel after protein transfection with Bclw, Bcl2, $Bclx_L$ or β-galactosidase control protein into axons; Scale bar=40 µm.
FIG. 3B is a bar graph depicting the degeneration index of FIG. 3A and untransfected (Untrans) control; *p<0.05 by one-way ANOVA with Bonferroni correction; data represents mean+SEM, n=4.
FIG. 3C is a bar graph showing the degeneration index of axons treated with paclitaxel or vehicle after protein transfection of Bclw, Bcl2, $Bclx_L$ or β-galactosidase control protein into cell bodies; data represents mean+SEM, n=4.
FIG. 3D depicts axons from compartmented cultures after protein transfection with FITC-tagged BH4 peptides of Bclw, Bcl2, or $Bclx_L$ showing FITC signal (left) and Tuj1 signal (right); Scale bar=20 µm.
FIG. 3E is a bar graph showing the degeneration index of axons treated with paclitaxel or vehicle after protein transfection of FITC-BH4-Bclw, Bcl2, or $Bclx_L$ into axons; *p<0.05 by one-way ANOVA with Bonferroni correction; data represents mean+SEM, n=4.
Figure 3:
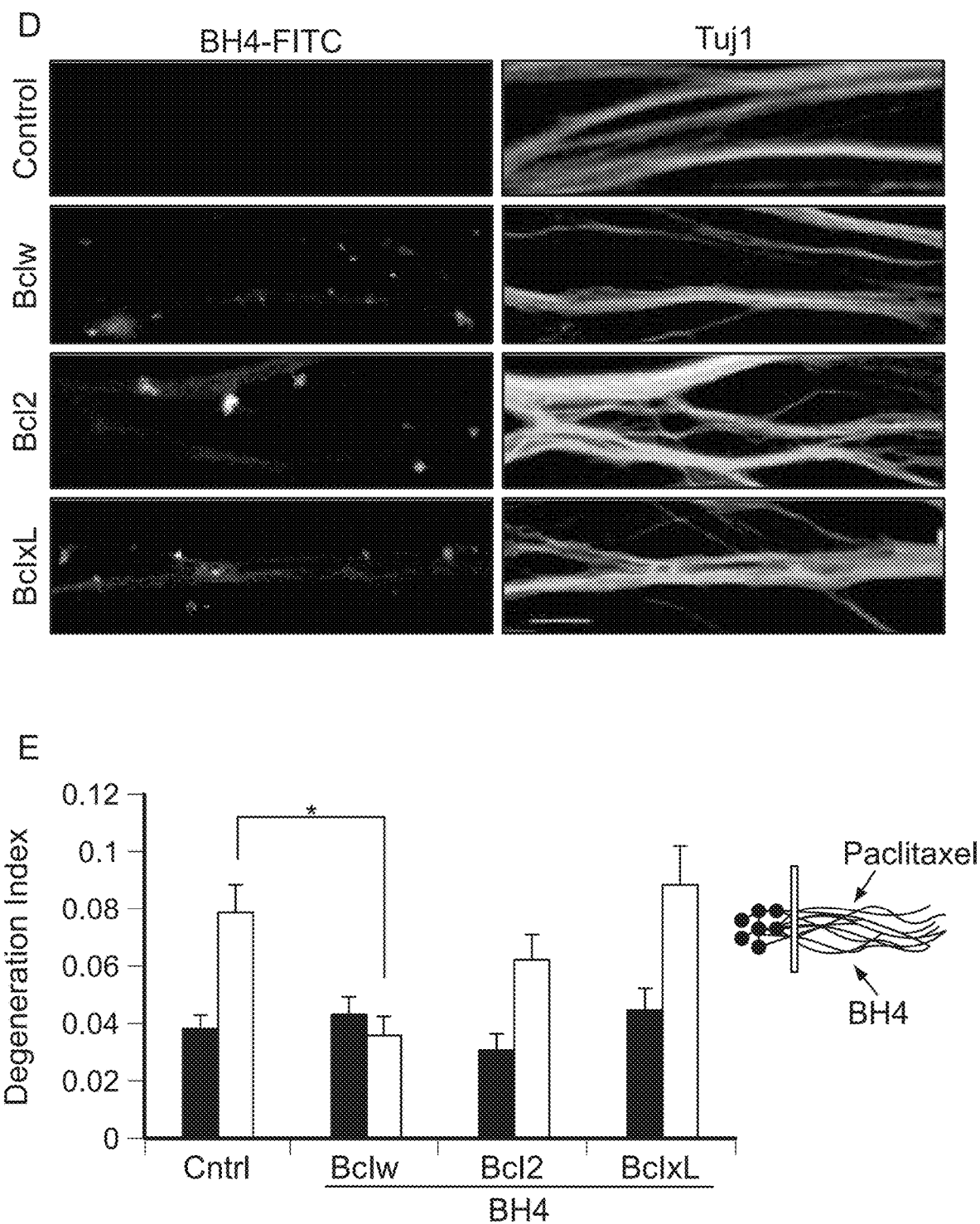

Although anti-apoptotic Bcl2 family members are involved in developmental axon degeneration, it is unclear if Bcl2 family members protect against axon degeneration caused by injury or disease. To identify anti-apoptotic Bcl2 family members that protect axons from the degenerative effects of paclitaxel, protein transfection was used in compartmented cultures to overexpress His-tagged recombinant Bclw, Bcl2, or Bclx$_L$ protein selectively in axons. Transfected axonal Bclw completely prevented paclitaxel-induced axon degeneration (FIGS. 3A and 3B). Although both Bclw and Bclx$_L$ have been reported to regulate developmental neurotrophin-dependent axon survival, it was found that neither Bclx$_L$ nor Bcl2 prevented degeneration when transfected into axons (FIG. 3A, 3B). Furthermore, selective introduction of Bclw, Bcl2, or Bclx$_L$ protein into cell bodies (instead of axons) failed to inhibit paclitaxel-induced degeneration (FIG. 3C). Together, these data identify Bclw as a specialized Bcl2 family member that can act locally in axons to prevent degeneration.

Example 4: The BH4 Domain of Bclw is Sufficient to Prevent Degeneration

BH4-Bclw inhibited BIM-induced, Bax-mediated membrane portion of ANTS/DPX encapsulated liposomes in a dose-dependent fashion (data not shown). FITC-tagged BH4 peptides of Bclw, Bcl2, or Bclx$_L$ or a vehicle control were transfected into axons of compartmented cultures; the axons were then treated with paclitaxel for 24 hours (FIG. 3D). As observed with full-length Bclw, the BH4-Bclw SAHB prevented paclitaxel-induced axon degeneration. Notably, however, BH4-Bcl2 and BH4-Bclx$_L$ did not do so (FIG. 3E). Equivalent intracellular bioactivity of these peptides in sensory neurons was confirmed using a neurotrophin-deprivation assay; transfection of BH4-Bclw, BH4-Bcl2, or BH4-Bclx$_L$ into cell bodies equally prevented apoptosis triggered by 24 hours of neurotrophin deprivation (data not shown). Together, these results indicate the BH4 domain of Bclw is sufficient to prevent axon degeneration, a function that is not conserved by the BH4 domains of Bcl2 and Bclx$_L$.

Example 5: Bclw Regulates IP$_3$R1 to Prevent Axon Degeneration

Figure 4:
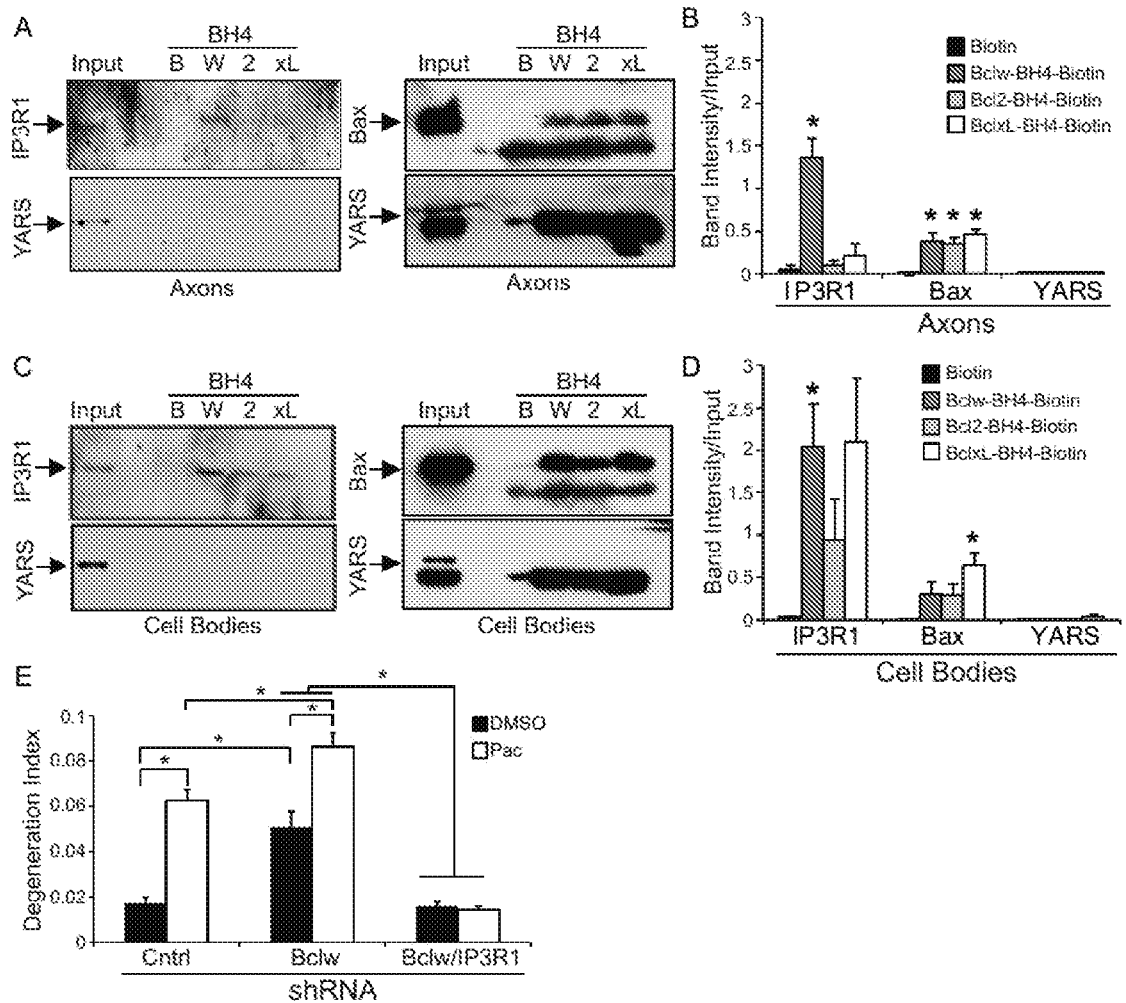
FIG. 4A shows a Western blot of NeutrAvidin pulldowns from axon lysate incubated with biotinylated BH4-Bclw (W), BH4-Bcl2 (2), or $BH4-Bclx_L$ ($x_L$) or biotin control (B). Western blots were probed for IP3R1, Bax, or YARS protein.
FIG. 4B is a bar graph showing the quantification of band intensity relative to input band from FIG. 4A. *p<0.05 relative to biotin control by one-way ANOVA with Dunnett's multiple comparison test; data represents mean+SEM, n=4-6.
FIG. 4C shows a Western blot of NeutrAvidin pulldowns from cell body lysate incubated with biotinylated BH4-Bclw (W), BH4-Bcl2 (2), or BH4-Bclx$_L$ (x$_L$) or biotin control (B). Western blots were probed for IP$_3$R1, Bax, or YARS protein.
FIG. 4D is a bar graph showing the quantification of band intensity relative to input band from FIG. 4C. *p<0.05 relative to biotin control by one-way ANOVA with Dunnett's multiple comparison test; data represents mean+SEM, n=4-6.
FIG. 4E is a bar graph depicting the degeneration index after 24-hour addition of paclitaxel or vehicle to axons following lentiviral infection with control shRNA or shRNAs targeting Bclw and/or IP$_3$R1; *p<0.05 by one-way ANOVA with Bonferroni correction; data represents mean+SEM, n=3-6.

The surprisingly specialized function of Bclw in preventing paclitaxel-induced degeneration can be because Bclw interacts with different molecular targets in axons than do Bcl2 and Bclx$_L$. As the BH4 domain of Bclw is alone sufficient to prevent paclitaxel-induced degeneration, co-precipitation of the biotinylated BH4 peptides of Bclw, Bcl2, or Bclx$_L$ with IP3R1 was performed. In axon lysate, IP3R1 co-precipitated preferentially with BH4-Bclw (FIGS. 4A and 4B), while in cell body lysate, IP$_3$R1 co-precipitated with all three SAHBs (FIGS. 4C and 4D). Importantly, biotinylated SAHBs all co-precipitated the pro-apoptotic Bcl2 family member Bax from both cell bodies (FIGS. 4A and 4B) and axons (FIGS. 4C and 4D), but did not co-precipitate a negative control protein, tyrosyl-tRNA synthetase (YARS; FIG. 4A-4D).

To determine if Bclw regulation of IP$_3$R1 is critical for preventing axon degeneration, neurons were infected with shRNAs targeting Bclw and/or IP3R1. Acute knockdown of Bclw increased spontaneous degeneration. Paclitaxel further increased axonal degeneration, suggesting that Bclw acts as a brake on the degenerative cascade activated by paclitaxel (FIG. 4E). If Bclw functions upstream of IP3R1 in this degenerative cascade, then simultaneous knockdown of IP$_3$R1 and Bclw should protect axons from paclitaxel. Indeed, IP$_3$R1 knockdown completely prevented axon degeneration caused by Bclw knockdown, in the absence or presence of paclitaxel (FIG. 4E). Together, these results indicate that Bclw acts upstream of IP3R1 to prevent axonal degeneration.

Example 6: Paclitaxel Specifically Reduces Axonal Bclw Levels

Figure 5:
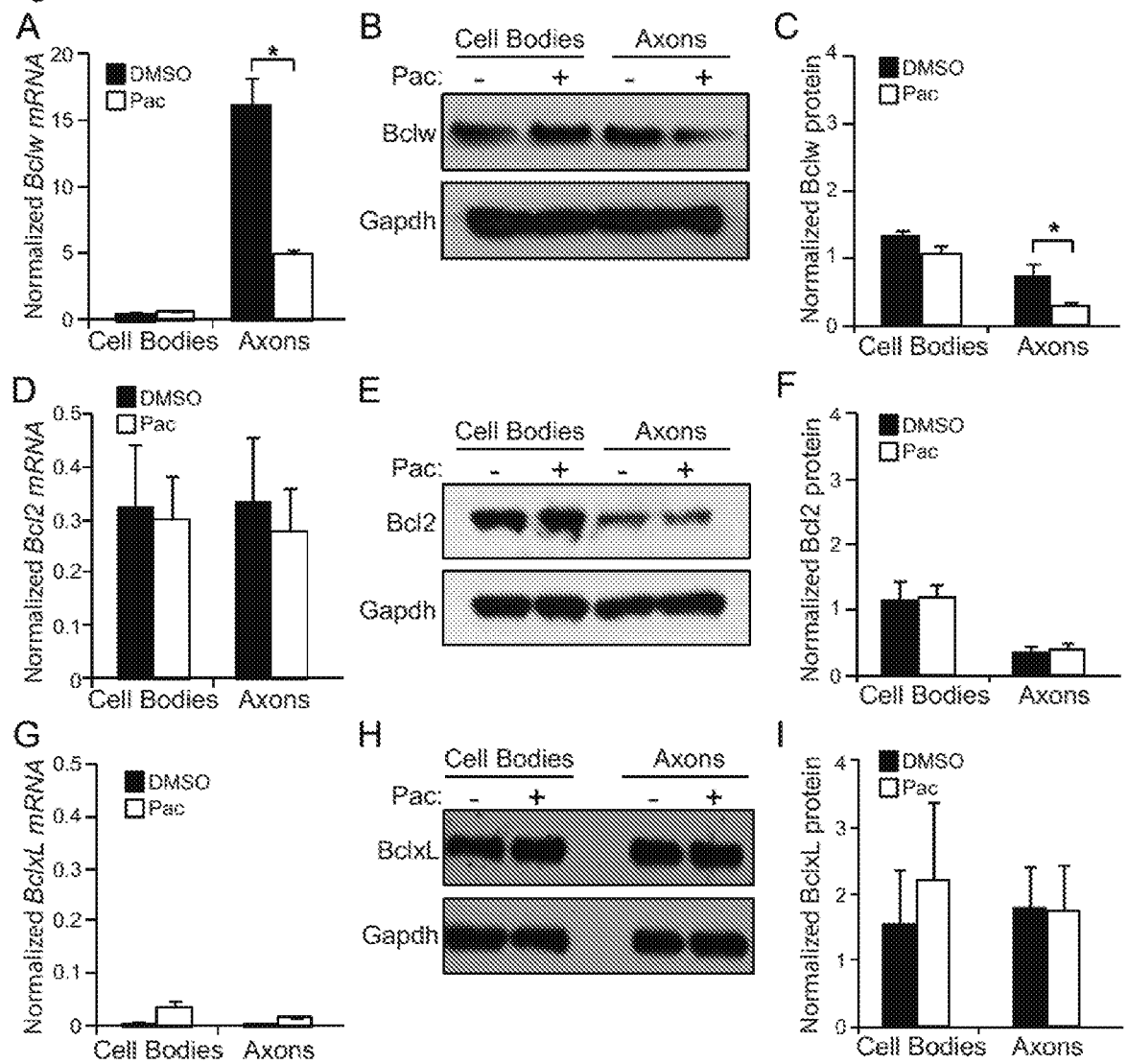
FIG. 5A is a bar graph showing Bclw mRNA analyzed by qRT-PCR from cell body or axon lysate of compartmented cultures after 24 hours of paclitaxel treatment to axons. Data normalized to GAPDH; *p<0.05 by one-way ANOVA with Bonferroni correction; data represents mean+SEM, n=3.
FIG. 5B is a Western blot for Bclw in the cell bodies and axons of the compartmented cultures of FIG. 5A.
FIG. 5C is a bar graph showing the quantification for Bclw from cell body or distal axon lysate of compartmented cultures after 24 hours of paclitaxel treatment to axons; data normalized to GAPDH; *p<0.05 by one-way ANOVA with Bonferroni correction; data represents mean+SEM, n=3.
FIG. 5D is a bar graph showing Bcl2 mRNA analyzed by qRT-PCR from cell body or axon lysate of compartmented cultures after 24 hours of paclitaxel treatment to axons. Data normalized to GAPDH; *p<0.05 by one-way ANOVA with Bonferroni correction; data represents mean+SEM, n=3.
FIG. 5E is a Western blot for Bcl2 in the cell bodies and axons of the compartmented cultures of FIG. 5D.
FIG. 5F is a bar graph showing the quantification for Bcl2 from cell body or distal axon lysate of compartmented cultures after 24 hours of paclitaxel treatment to axons; data normalized to GAPDH; *p<0.05 by one-way ANOVA with Bonferroni correction; data represents mean+SEM, n=3.
FIG. 5G is a bar graph showing Bclx$_L$ mRNA analyzed by qRT-PCR from cell body or axon lysate of compartmented cultures after 24 hours of paclitaxel treatment to axons. Data normalized to GAPDH; *p<0.05 by one-way ANOVA with Bonferroni correction; data represents mean+SEM, n=3.
FIG. 5H is a Western blot for Bclx$_L$ in the cell bodies and axons of the compartmented cultures of FIG. 5G.
FIG. 5I is a bar graph showing the quantification for Bclx$_L$ from cell body or distal axon lysate of compartmented cultures after 24 hours of paclitaxel treatment to axons; data normalized to GAPDH: *p<0.05 by one-way ANOVA with Bonferroni correction; data represents mean+SEM, n=3.

The expression of the anti-apoptotic components Bclw, Bcl2, or Bclx$_L$ was examined after paclitaxel treatment. Strikingly, paclitaxel treatment reduced Bclw mRNA and protein levels selectively in axons and not in cell bodies (FIG. 5A-5C). In contrast, paclitaxel treatment did not alter Bcl2 and Bclx$_L$ mRNA or protein in axons or cell bodies (FIG. 5D-5I). Together, these data indicate that paclitaxel reduces axonal Bclw levels with no effect on closely related Bcl2 family members.

Example 7: Loss of Bclw Exacerbates Paclitaxel-Induced Neuropathy In Vivo

Figure 6:
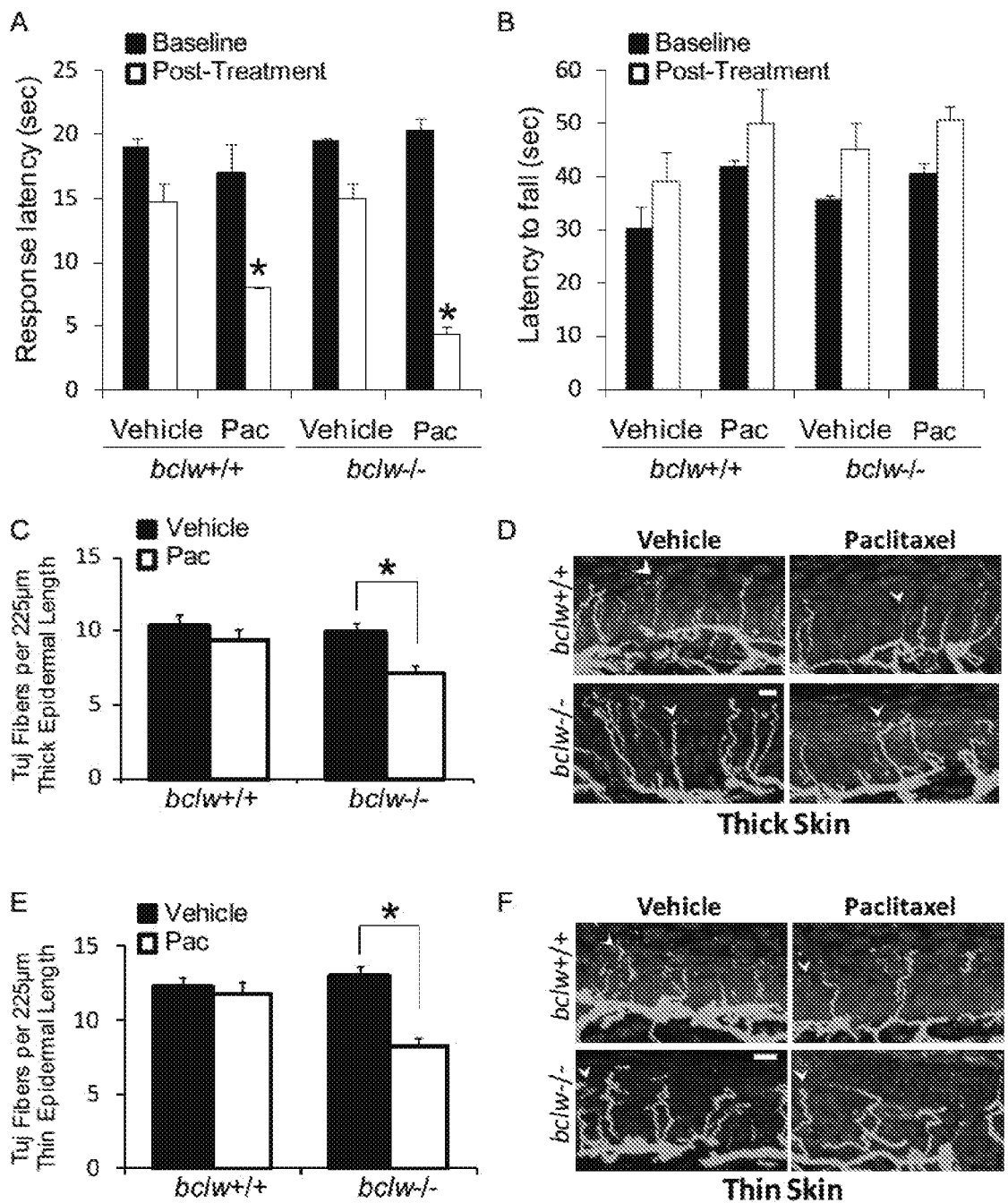
FIG. 6A is a bar graph showing the thermal pain threshold measured as time to lick or withdraw hindpaw on a 50° C. hot-plate. This behavioral assessment was done with mice treated with paclitaxel before (Baseline) and ten days after the final injection (post-treatment); data represents mean+SEM, n=3-4 mice.
FIG. 6B is a bar graph depicting latency to fall off an accelerating Rotarod. This behavioral assessment was done with mice treated with paclitaxel before (Baseline) and ten days after the final injection (post-treatment); data represents mean+SEM, n=3-4 mice.
FIG. 6C is a bar graph showing the quantification of Tuj1 positive sensory fibers entering the epidermis per 225 μm epidermal length in thick skin. *p<0.05 by Student's t-test, data represents mean+SEM, n=3-4 mice.
FIG. 6D shows representative images of Tuj1 positive sensory fibers (arrowheads) entering the epidermis per 225 μm epidermal length in thick skin. Scale bar=10 μm, n=3-4 mice, 8-15 images per mouse.
FIG. 6E is a bar graph showing the quantification of Tuj1 positive sensory fibers entering the epidermis per 225 μm epidermal length in thin skin. *p<0.05 by Student's t-test, data represents mean+SEM, n=3-4 mice.
FIG. 6F shows representative images of Tuj1 positive sensory fibers (arrowheads) entering the epidermis per 225 μm epidermal length in thin skin. Scale bar=10 μm, n=3-4 mice, 8-15 images per mouse.
Figure 7:
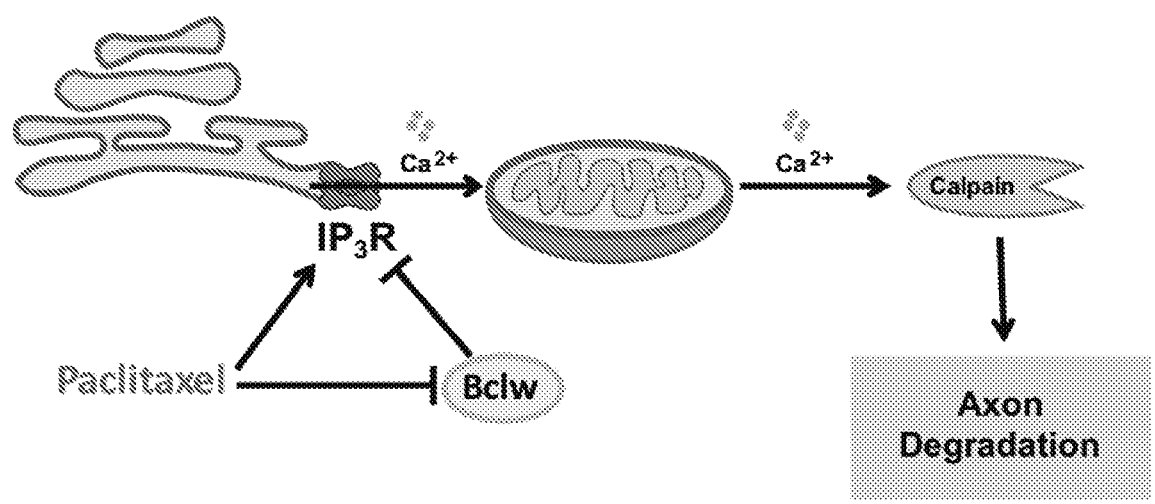
FIG. 7 is a model showing the mechanism of paclitaxel-induced axonal degeneration. Paclitaxel reduces axonal Bclw levels and causes activation of an IP$_3$R1-dependent degeneration cascade characterized by mitochondrial dysfunction and calpain protease activation.

To examine the role of Bclw in paclitaxel-induced degeneration in vivo, 2 month old bclw+/+ and bclw−/− mice were injected with paclitaxel (4 mg/kg every other day for 8 days). While bclw+/+ mice developed mild thermal hyperalgesia after paclitaxel treatment, as measured by a 50 hot-plate test, bclw−/− mice developed a more severe thermal pain sensitivity (FIG. 6A). In patients, paclitaxel causes a primarily sensory neuropathy. Paclitaxel-treated mice were confirmed to have normal motor function using an accelerating RotaRod test (FIG. 6B). To assess the effect of paclitaxel on sensory neuron axons directly, intraepidermal nerve fibers of the hindpaw were examined after paclitaxel treatment. Compared to bcw+/+ mice, bclw−/− mice treated with paclitaxel exhibited a greater reduction in intraepidermal nerve fiber number in both thick (dermal papillae-containing; FIGS. 6C and 6D) and thin (non-dermal papillae containing; FIGS. 6E and 6F) skin. Together, these results indicate that reduced expression of bclw causes enhanced susceptibility to paclitaxel-induced degeneration both in vitro (FIG. 4E) and in vivo (FIG. 6A-6F).

Example 8: Materials & Methods for Examples 9 and 10

Bclw mRNA Expression Analysis in Cochlea.

| Primer Name | Primer Sequence |
|---|---|
| Bclw forward primer | 5'-AGCCTCAACCCCAGACACAC-3' (SEQ ID NO: 39) |
| Bclw reverse primer | 5'-TCACTTGCTAGCAAAAAAGGC-3' (SEQ ID NO: 40) |
| Bclw reverse nested primer | 5'-TAATACGACTCACTATAGGACAGT TACCAGGGCCCCCAGT-3' (SEQ ID NO: 41) |
| β-actin forward primer | 5'-TCAGAAGGACTCCTACGTGGGC-3' (SEQ ID NO: 42) |
| β-actin reverse primer | 5'-AGGTCCAGACGCAGGATGGC-3' (SEQ ID NO: 43) |
| β-actin reverse nested primer | 5'-TAATACGACTCACTAACCCTCATAGC-3' (SEQ ID NO: 44) |

RNA Probe Design and Generation.

RNA probes against Bclw were amplified from rat constructs using gene-specific sets of PCR primers which were designed by hand and purchased from Invitrogen (Table 1). To generate the Bclw probe, two rounds of PCR were performed before DIG labeling. Bclw forward and reverse primers were reacted with a rat Bclw construct, MgCl$_2$ (Invitrogen), dNTPs (Roche), ddH$_2$O, PCR Buffer (Invitrogen), and Taq DNA polymerase (Invitrogen). Each PCR included 30 cycles and an initializing step at 95 degrees Celsius for 2 min, a denaturation step at 95 degrees Celsius for 30 sec, an annealing step at 58 degrees Celsius for 30 sec, an elongation step at 72 degrees Celsius for 1 min, and a final elongation step at 72 degrees Celsius for 10 min. PCR products were run on a 1.2% agarose gel (loading buffer and 1.2% agarose) and bands with a length of ~550 bp were extracted with a gel extraction kit (QIAGEN). Extracted DNA was subsequently used for a second PCR reaction, which used a Bclw forward primer and reverse nested primer containing the T7 promoter sequence (5'-TAA TAC GAC TCA CTA TAG GG-3') (SEQ ID NO:45). For this second PCR, all steps were identical to the preceding PCR. PCR products were subsequently run on a 1.2% agarose gel and bands with a length of ~500 bp were extracted with a gel extraction kit. To confirm the purity and sequence of the DNA, the PCR products were analyzed using a Nanodrop 8000 spectrophotometer (Thermo Scientific) and sequenced at the Dana-Farber DNA Sequencing Facility.

Bclw PCR products were DIG labeled to generate labeled riboprobes for in situ hybridization by reacting PCR products with 5× transcription buffer (Promega), 0.1 M DTT, T7 polymerase (Promega), RNasin (Promega), DIG labeling mix (Promega), and DEPC Water for 2 h at 37 degrees Celsius. 10 µl DNase (Promega) was added to the mixture and left to incubate for 10 min at 37 degrees. The reaction was stopped by adding 52 µl of stop buffer. DIG labeled RNA was extracted using an RNeasy Plus Mini Kit (QIAGEN) and resuspended in 50 µl of DEPC $H_2O$ before being diluted into hybridization buffer at 1 µg/ml (50% Formamide, 5×SSC, 0.2 mg/ml yeast tRNA, 100 µg/ml heparin, 1×Denhardt's solution, 0.1% Tween, 0.1% Chaps, 5 mM EDTA). RNA purity was confirmed using a Nanodrop 8000 spectrophotometer.

RNA probes against β-actin were amplified from rat constructs using gene-specific sets of β-actin forward, reverse, and reverse nested PCR primers which were designed by hand and purchased from Operon. The annealing temperature for the first and second PCR was 62 degrees Celsius. All other steps were consistent with the methods for generating Bclw RNA probes. β-actin RNA probes served as a positive control for in situ hybridization.

A scrambled sense probe was created by linearizing a miniprep Mef2A vector using vector-specific T7 and SP6 primers. An annealing temperature of 52 degrees Celsius was used during the linearizing step. All other methods were consistent with the methods for generating Bclw RNA probes. Scrambled probes served as a negative control for in situ hybridization.

Rats.

Timed pregnant rats were purchased from Charles River. All rats dissected were wild-type littermates between ages P5 and P6. All procedures were performed in accordance with the NIH guidelines and were approved by the Dana-Farber Cancer IACUC.

Tissue Preparation.

Rats (P5 and P6) were sacrificed by isoflurane (Abbott) inhalation and immediately underwent intracardial perfusion with one body volume (approximately 15 mL) of DEPC-PBS followed by one body volume of 4% PFA in DEPC-PBS. Following perfusion, rats were decapitated and severed heads were either immediately dissected or stored overnight at 4° C. in a solution of 4% PFA in DEPC-PBS before dissecting the following day.

Rat heads were scored down the midline and cochlea were dissected in cold DEPC-PBS over ice. Cochlea were then drop-fixed in 4% PFA in DEPC-PBS overnight at 4 degrees Celsius. After overnight fixation, tissues were then washed 3 times for 5 min in DEPC-0.1% PBST (PBS and 0.1% Triton X-100) over ice and then dehydrated in a graded methanol/0.1% PBST series (25%, 50%, 75%) into 100% methanol and stored at −20 degrees Celsius until needed.

In Situ Hybridization for BCLW mRNA Expression Analysis in Cochlea.

All in situ hybridization steps were completed using net wells in 12 well plates (BD Falcon) to reduce potential damage to the cochlea when transferred between washes. A total of 9 cochlea were used for each experiment since 3 cochlea were used to detect Bclw mRNA and another 6 cochlea were divided evenly for the positive (β-actin) and negative (scrambled) controls. RNaseZap (Life Technologies) was used to decontaminate the lab bench and any tools used for in situ hybridization.

Day 1: Cochlea were removed from methanol and rehydrated stepwise into 100% DEPC-0.1% PBST. In each step, approximately 2 ml of solution was applied per well to cover all the tissue. Tissues were then washed 3 times for 5 min in DEPC-0.1% PBST and re-fixed in 4% PFA in DEPC-PBS for 20 min at room temperature. Cochlea were then washed 3 times for 5 min in DEPC-0.5% PBST at room temperature and pre-hybridized with hybridization buffer without probe for 1 hour at 65 degrees Celsius. Pre-hybridization buffer was replaced with hybridization buffer containing 1 µg/ml of probe and cochlea were incubated overnight at 65 degrees Celsius.

Day 2: Hybridization buffer was removed and cochlea were washed 2 times with pre-warmed Solution I (50% formamide, 5×SSC, 1% SDS, and DEPC-$H_2O$) at 70 degrees Celsius for 30 min. Subsequently, tissue was washed once for 20 min at 70 degrees Celsius with 50% Solution I: 50% Solution II (0.5 M NaCl, 10 mM Tris HCl pH 7.5, 0.1% Tween-20, and DEPC-$H_2O$), 3 times for 5 min with Solution II at room temperature, 2 times in Solution III (50% formamide and 2×SSC) for 30 min at 65 degrees Celsius, and 3 times for 5 min in TBST (50 mM Tris, 150 mM NaCl, 0.05% Tween 20). Tissues were then washed in blocking solution (TBST and 10% lamb serum) at room temperature for 2.5 h. Cochlea were then incubated on a rocker at 4 degrees Celsius overnight in blocking solution containing 1:2000 alkaline phosphatase-conjugated sheep anti-digoxigenin (Roche Diagnostics).

Day 3: Cochlea were removed from the blocking solution and washed 3 times for 5 min and then 4 times for 1 h in TBST. Tissues were left overnight in TBST at 4 degrees Celsius.

Day 4: Cochlea were removed from TBST and washed 2 times for 20 minutes in fresh alkaline phosphatase buffer (100 mM Tris pH 9.5, 50 mM $MgCl_2$, 0.1% Tween-20, 100 mM NaCl, and DEPC-$H_2O$) and then incubated in BM Purple (Roche) until signal was dissected under a dissecting microscope (Olympus SZ-ST). The reaction was stopped by washing 2 times for 5 min in 0.1% PBST/5 mM EDTA and fixing overnight in 4% PFA.

Day 5: After fixation, cochlea were transferred and washed 2 times for 10 min in 0.1% PBST/5 mM EDTA and imaged. After whole mount imaging, flat mounts were created and mounted on glass slides (Fisherbrand) using Fluoro-mount mounting media (Southern Biotec) and left in the dark at 4 degrees Celsius until further imaging.

Whole Mount Imaging.

Whole mount imaging was done on a MVX10 MacroView dissecting microscope at the Harvard Medical School Neurobiology Imaging Facility.

Flat Mount Imaging.

Flat mount imaging was done on a microscope at the 20× objective at Dana-Farber Cancer Institute.

Immunofluorescence for BCLW Expression Analysis in Cochlea.

Before experimentation, cochlea were removed from 4% PFA in DEPC-PBS and dissected to create flat mounts representative of the apical and basal turns. One cochlea was used to create the control flat mounts and once cochlea was used to create the experimental flat mounts for each experiment. All experiments were performed in 24 well plates, with one flat mount per well. The following protocol was used for all immunofluorescence experiments.

Day 1: Flat mounts were washed in PBS and incubated overnight at room temperature on a rocker. Approximately 500 µl of solution was used to cover the tissues.

Day 2: PBS was removed using a pipette and replaced with a permeabilizing solution (10% normal goat serum (NGS), 0.1% Triton X-100, and PBS) for 1 h at room temperature. After permeabilizing solution was removed, approximately 500 µl of primary antibody diluted in blocking solution (primary antibody, 5% NGS, and PBS) was applied to each well. Flat mounts were incubated in primary antibody solution overnight at 4 degrees Celsius on a rocker. The antibodies and dilutions used were as follows: BCLW rabbit (Cell Signaling) at 1:500 and TUJ1 mouse (Covance) at 1:300. Control flat mounts were not incubated in BCLW primary antibody and only received the TUJ1 primary antibody. Both control and experimental flat mounts were treated equally for all other steps in the immunofluorescence protocol.

Day 3: After overnight incubation, the primary antibody solution was removed and flat mounts were washed 4 times in PBS for one hour at room temperature to remove excess primary antibody. Approximately 500 µl of PBS was added to each well. Flat mounts were incubated overnight at 4 degrees Celsius in PBS.

Day 4: PBS was removed from wells and replaced with approximately 500 µl of secondary antibody (Alexa Fluor 488 goat anti-mouse (Invitrogen) at 1:400 or Alexa Fluor 546 goat anti-rabbit (Invitrogen) at 1:400) diluted in blocking solution (5% NGS and PBS). Each flat mount was incubated in the secondary antibody solution for 1 h at room temperature in the dark. After incubation in the secondary antibody solution, all subsequent steps were performed in the dark. After removal of the secondary antibody solution, flat mounts were washed 3 times in 500 µl of PBS for 5 min each. For nuclear staining, 500 µl of 4',6-diamidino-2-phenylindole, or DAPI (5 mg/mL in ddH$_2$O), was diluted 1:1000 in PBS and applied to washed flat mounts for 10 min. After removal of DAPI, flat mounts were washed 3 more times in PBS for 1 h each and incubated overnight on a rocker at 4 degrees Celsius to remove excess secondary antibody.

Day 5: Flat mounts were placed on superfrost glass slides (Fisherbrand) and received 50 µl of Fluoro-mount mounting media (Southern Biotec). Tissues were then cover slipped and allowed to dry overnight before imaging.

Imaging.

Sections were imaged using a Nikon Eclipse TI inverted microscope with the 20× objective. Images were obtained using NIS Imaging software.

Quantification for BCLW Expression Analysis in Cochlea.

Images were quantified using ImageJ software to measure the pixel intensity of BCLW signal in cell bodies and axons. Signal intensity from cell bodies and axons was then normalized to controls. BCLW images for control and experimental tissues were then thresholded to remove background signal. After thresholding, both control and experimental BCLW images were brightened. All BCLW images from control and experimental tissues were manipulated equally to effectively capture the difference in signal.

Behavioral Analysis of Bclw+/+ and Bclw−/− Mice.

The subjects were 31 bclw+/+ and bclw−/− mice on the C57Blk6EJ Blk6 background that does not contain the nnt mutation found in the Blk6J mice. 13 different litters contributed to both groups. The mice, originally obtained from Jackson Laboratory (Bar Harbor, Me.), were bred at the Dana-Farber Cancer Institute. The mice were maintained on a 12-hr light-dark cycle with lights on at 7 A.M. and were housed in groups of 1 to 5 mice. All mice were tested for hearing between 3 P.M. and 4 P.M. on testing days. Mice were labeled 1-31 in the order of their birth from oldest to youngest and genotypes were blinded until the conclusion of testing.

The number of mice used for the behavioral analysis was determined by power analysis using STATA and a two sample comparison of means. 6 months and 14 months were used as the mean ages of deafness onset for bclw−/− and bclw+/+ mice, respectively. Standard deviations of 8 months and 4 months were used for bclw−/− and bclw+/+ mice, respectively. The standard deviation for the mean age of deafness onset for bclw−/− mice was calculated by finding the difference between the means. P<0.05 was considered statistically significant. At most, 28 mice were needed for a 90' probability of capturing a statistically significant result.

In each training session, mice were tested for hearing in new, plastic cages provided by the Dana-Farber Cancer Institute Animal Facility. Cages were placed inside a hood with the light turned on but the blower turned off. Each behavior test was video recorded using an Apple iPhone 4S with 1080p HD video recording. All mice in the Dana-Farber Cancer Institute Animal Facility were habituated to white noise by playing background music continuously on a radio. This music persisted in the background during testing. An auditory stimulus, 86 dB, was produced by a Petco dog training clicker.

Mice were first tested at 6 weeks after birth and then every 3 weeks thereafter until 40 weeks of age. 40 weeks was selected as the endpoint for testing since mice on the Blk 6 background develop age-related hearing loss soon after that age, with complete degeneration of the organ of Corti observed by 12 months. During testing, each mouse was removed one at a time from its cage and placed in a new, fresh cage where it was allowed to habituate for 5 min. After the habituation time elapsed, the testing session began and the mouse was presented with three auditory stimuli, each separated by 3 to 6 sec. Responses to the auditory stimuli were video recorded from beginning to end of each testing session. After testing sessions, mice were returned to their original cages. All auditory tests were performed blind to the genotypes.

For each testing session, mice were labeled as having either strong, weak, or no hearing. This designation was determined by observation of a Preyer's reflex, an elicitation of startle responses to auditory stimuli. A response was considered positive if there was rapid movement of the mouse's entire body or flicking of the pinna immediately following presentation of the auditory stimulus. Those that showed a Preyer's reflex following all three stimuli were labelled as having complete hearing ability. Mice responding to two stimuli were labelled as having weak hearing, and those responding to one or none of the stimuli were deemed deaf. Genotypes were blinded until the conclusion of experimentation. The time of deafness onset for each mouse was defined as the first test date in which the mouse no longer responded to any auditory stimuli. For these mice, all subsequent testing dates also showed no hearing ability. The mean ages of deafness onset for bcw+/+ and bclw−/− mice were compared using a Wilcoxon test (nonparametric t-test for means and proportions). P<0.05 was considered statistically significant.

Example 9: Expression of Bclw in Spiral Ganglion Neurons in Cochlea

Bclw mRNA is Expressed in the Cochlea Along an Apical-Base Gradient.

It was hypothesized that Bclw plays a role in axonal maintenance of spiral ganglion neurons. This could explain the asymmetric degeneration of peripheral spiral ganglion axons observed during age-related hearing loss in humans, which parallels the retrograde degeneration of dorsal root ganglion peripheral axons in Bclw−/− mice. To evaluate this possibility, whole-mount in situ hybridization was performed using Bclw, β-actin, and scrambled RNA probes to detect the presence of Bclw mRNA in cochlea dissected from wild-type P5-P6 rats.

Figure 8:
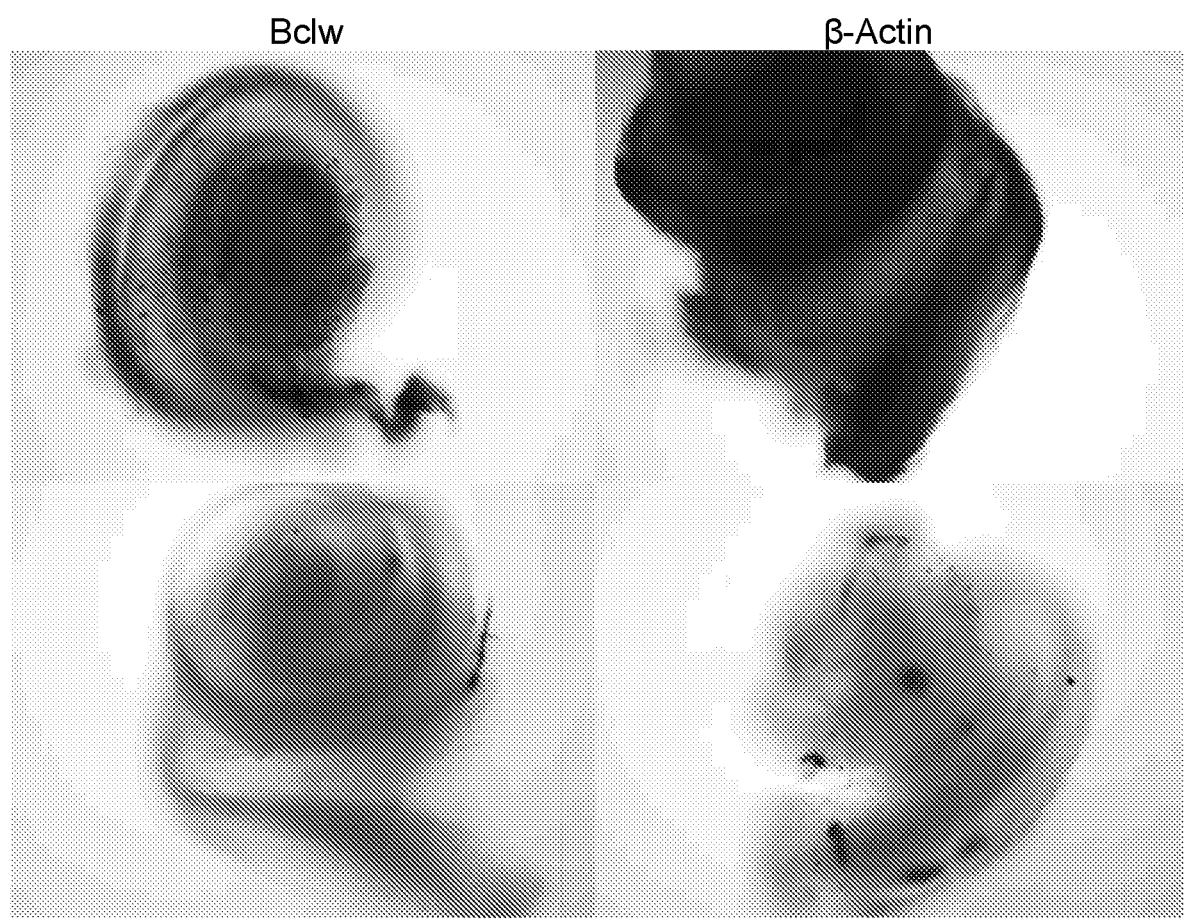
FIG. 8 shows representative images of whole-mount in situ hybridization assays showing expression of Bclw mRNA in rat cochlea.

Because β-actin is known to be targeted to axons and locally translated to facilitate growth cone motility and axon guidance in response to neurotrophins, β-actin was expected to be present both in cell bodies and axons of spiral ganglion neurons. Given the hypothesis that Bclw is expressed in spiral ganglion neurons and transported to peripheral projections, it was predicted that the pattern of Bclw signal would be similar to the pattern of β-actin signal. In situ hybridization assays showed that β-actin and Bclw are both highly expressed within the cochlea (FIG. 8). Moreover, expression of both genes in the base of the cochlea was localized to the spiral ganglion cell bodies. This result contrasted with findings from the scrambled probe which failed to show any signal. These data show that Bclw mRNA is expressed in the cochlea and potentially in the spiral ganglion cell bodies.

To more precisely investigate the pattern of Bclw mRNA expression and localization in the cochlea, flat mounts of cochlear turns were created and imaged following whole mount in situ hybridization using Bclw, β-actin, and scrambled RNA probes. Neurogenesis and gene expression follow an apical-base gradient in which circuits develop first in the base of the cochlea, so it was important to determine whether Bclw mRNA expression differs between apical and basal turns. To test this possibility, images of flat mounts of basal and apical turns from the same cochlea were analyzed following in situ hybridization.

In situ hybridization showed robust β-actin mRNA expression in regions of the base and apex associated with spiral ganglion cell bodies. β-actin mRNA also appeared to localize to the spiral lamina where peripheral processes converge into radial bundles and extend to the sensory epithelium to innervate inner hair cells (IHCs) and outer hair cells (OHCs). This signal pattern was not diffuse in the spiral lamina but rather formed a band which persisted along the entire apical-base axis (FIGS. 9A and 9B). Within basal turns, Bclw mRNA expression and localization followed a pattern similar to that of β-actin mRNA, with signal detected both in the spiral lamina and in the modiolus where spiral ganglion cell bodies are housed. However, this pattern was observed only in the base and did not persist in the apex, suggesting that Bclw mRNA expression follows an apical-base gradient (FIGS. 9A and 9B). Taken together, these findings reveal that Bclw mRNA is present in cell bodies and potentially in axons, and that expression follows an apical-base gradient.

Example 10: Bclw−/− Mice Develop Early Onset Hearing Loss

In parallel with molecular studies to assess the expression of Bclw in spiral ganglion neurons (Example 9), the function of Bclw in maintaining hearing during aging was investigated by behavioral analysis. To test the hypothesis that bclw−/− mice would have an earlier onset of hearing loss than wild-types, an experiment was designed whereby bclw−/− and wild-type mice on the same background (C57Blk6EJ) were measured for hearing ability at scheduled time periods during their lifespan. Based on studies of sensory neuron degeneration and associated deficits in thermosensation in bclw−/− mice, it was hypothesized that Bclw knockout mice would demonstrate hearing loss at 4 to 6 months of age. Though the Blk6 background is known to develop hearing loss after 12 months of age, this variable was controlled for by comparing knockouts on the C57Blk6EJ Blk6 background to wild-types that were also on the C57Blk6EJ Blk6 background. To assess hearing ability, mice were exposed to three auditory stimuli during each training session. Observation of a Preyer's reflex following a stimulus was considered a positive response. Based on the number of stimuli which received a positive response, mice were labeled as having either strong, weak, or no hearing ability. 31 mice were studied over the course of several months and the average age of deafness onset was compared between bclw−/− C57Blk6EJ Blk6 and wild-type C57Blk6EJ Blk6 mice.

Figure 10:
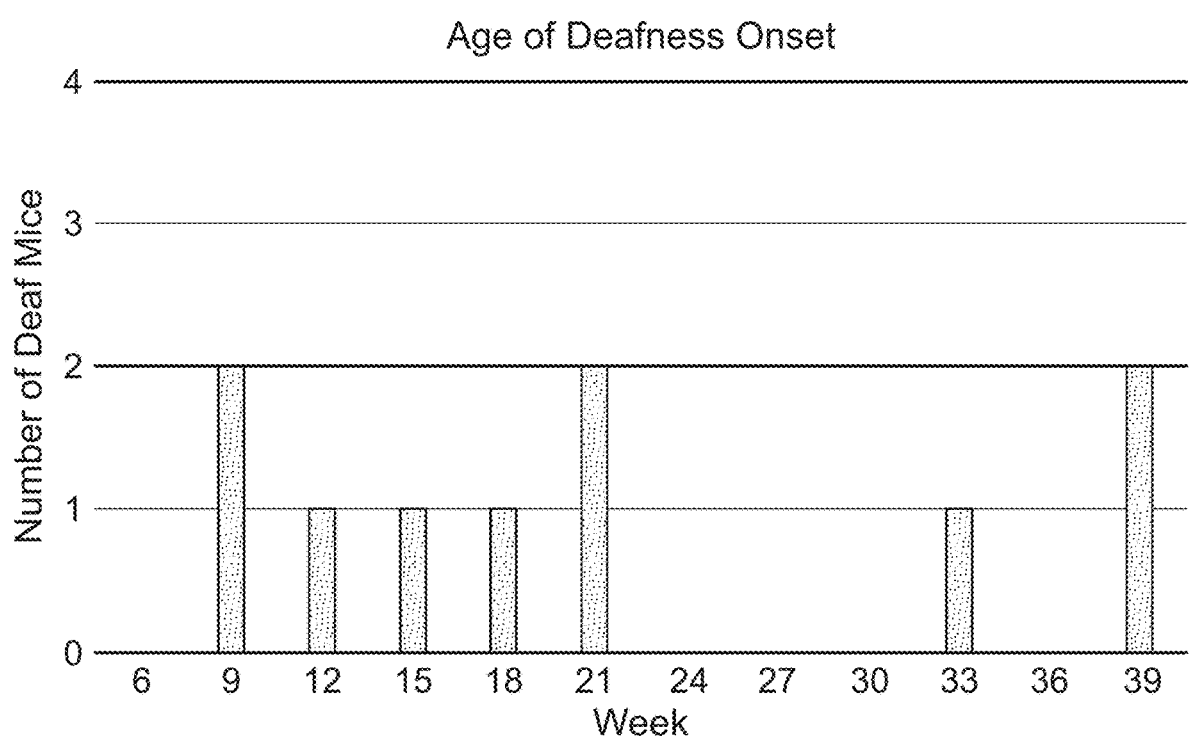
FIG. 10 is a bar graph showing the segregation of bclw−/− and wild-type mice into two populations suffering from either early or late hearing loss.

Blinded results of the age of deafness onset showed a bimodal distribution of ages, indicating that mice are segregated into two populations which develop hearing loss either at early or later stages (FIG. 10). The first population showed hearing loss between 9 and 21 weeks of age, with an average age of deafness onset of 15 weeks. This age is in agreement with the hypothesis that bclw−/− mice would show hearing deficits by 4 months of age. In contrast, the second population showed deafness at 33 to 39 weeks of age, with an average age of deafness of 37 weeks, consistent with the age-related deafness known to occur in wild-type C57Blk6EJ Blk6 mice. These results suggest that Bclw is necessary for the maintenance of hearing during aging.

Example 11: Therapeutic Value of Enhancing Bcl-w Activity to Prevent Hearing Loss Four cohorts of animals were tested:
(i) CBA wild-type mice, with no noise exposure (n=3);
(ii) CBA wild-type mice, with noise exposure (n=5);
(iii) CBA wild-type mice injected with a bcl-w expressing virus at P1, with no noise exposure (n=5); and
(iv) CBA wild-type mice injected with a bcl-w expressing virus at P1, with noise exposure (n=4).

The noise exposure consisted of 100 dB of broadband noise for 2 hours. All animals were approximately 3 months old at the time and were treated and handled in parallel. Two weeks later, each mouse was tested for hearing, using two measures. First, we measured Distortion product optoacoustic emissions (DPOAE) responses, which are an indication of outer hair cell (and hence cochlear) function. Second, we measured Auditory Brainstem Responses (ABRs), which are created by the neural activity that passes from the cochlea to the brainstem. For DPOAEs and ABRs, we evaluated the threshold for response, i.e., how "loud" the sound needs to be to generate a signal either in the hair cells (DPOAE) or neurons (ABR). The hair cells activate the neurons, so if there is a change in hair cell activity, there will also be a change in neuronal activity. Thus, if DPOAE thresholds are unchanged, but ABR thresholds are changed, we can surmise that the neurons are primarily affected.

In addition, we measured the amplitude of the first ABR wave, which is a more sensitive measure of the neuronal response. When more neurons are activated synchronously, the amplitude increases. Thus, in wild-type animals, as the stimulus is made louder (i.e., increased sound pressure level, as measured in dB), the amplitude of the first wave (as measured in microvolts) also increases. If there is a loss of activated neurons, then the amplitudes are smaller and do not increase much with increased sound pressure levels.

Figure 11:
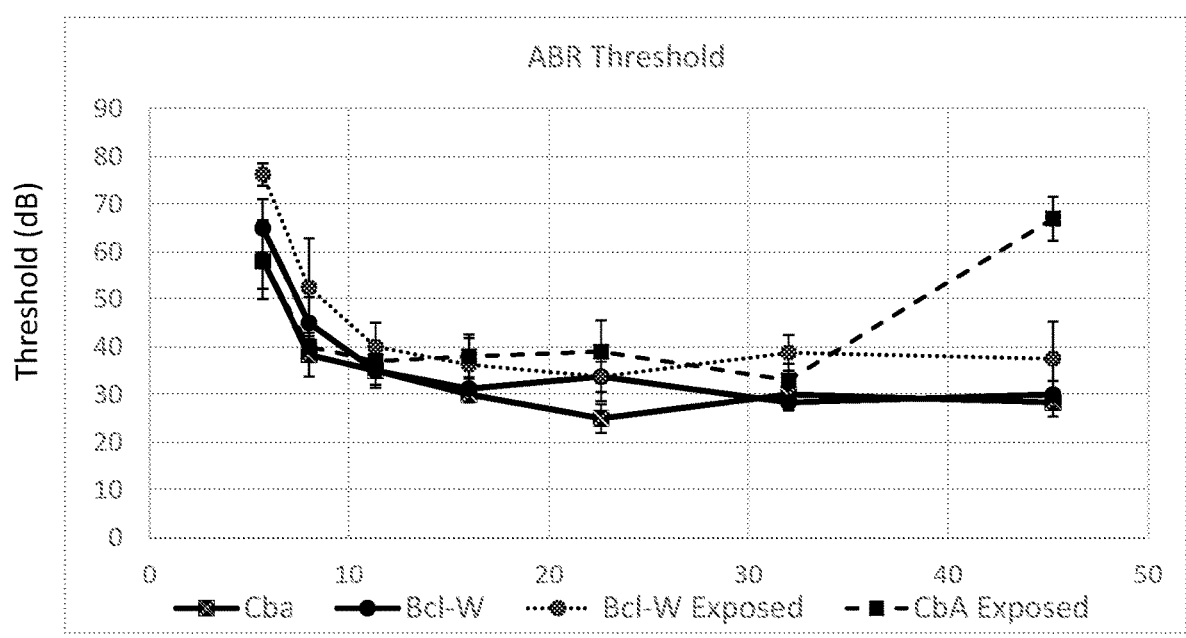
FIG. 11 is a graph depicting ABR thresholds in the mice studied in Example 11.
Figure 12:
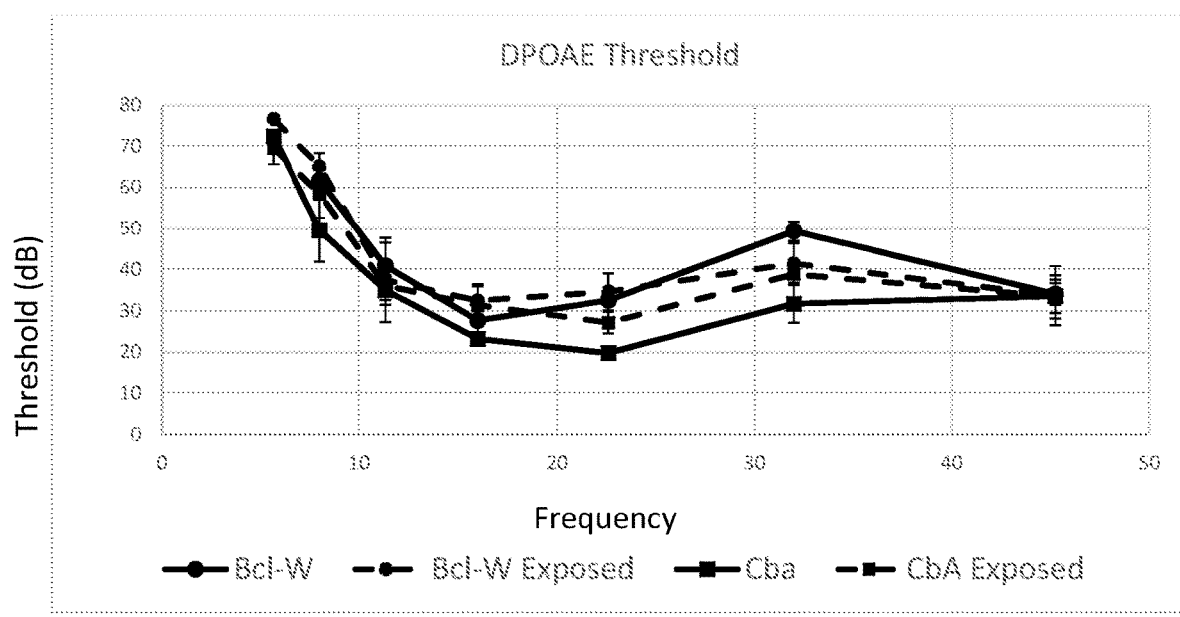
FIG. 12 is a graph showing DPOAE thresholds in the mice studied in Example 11.
Figure 13:
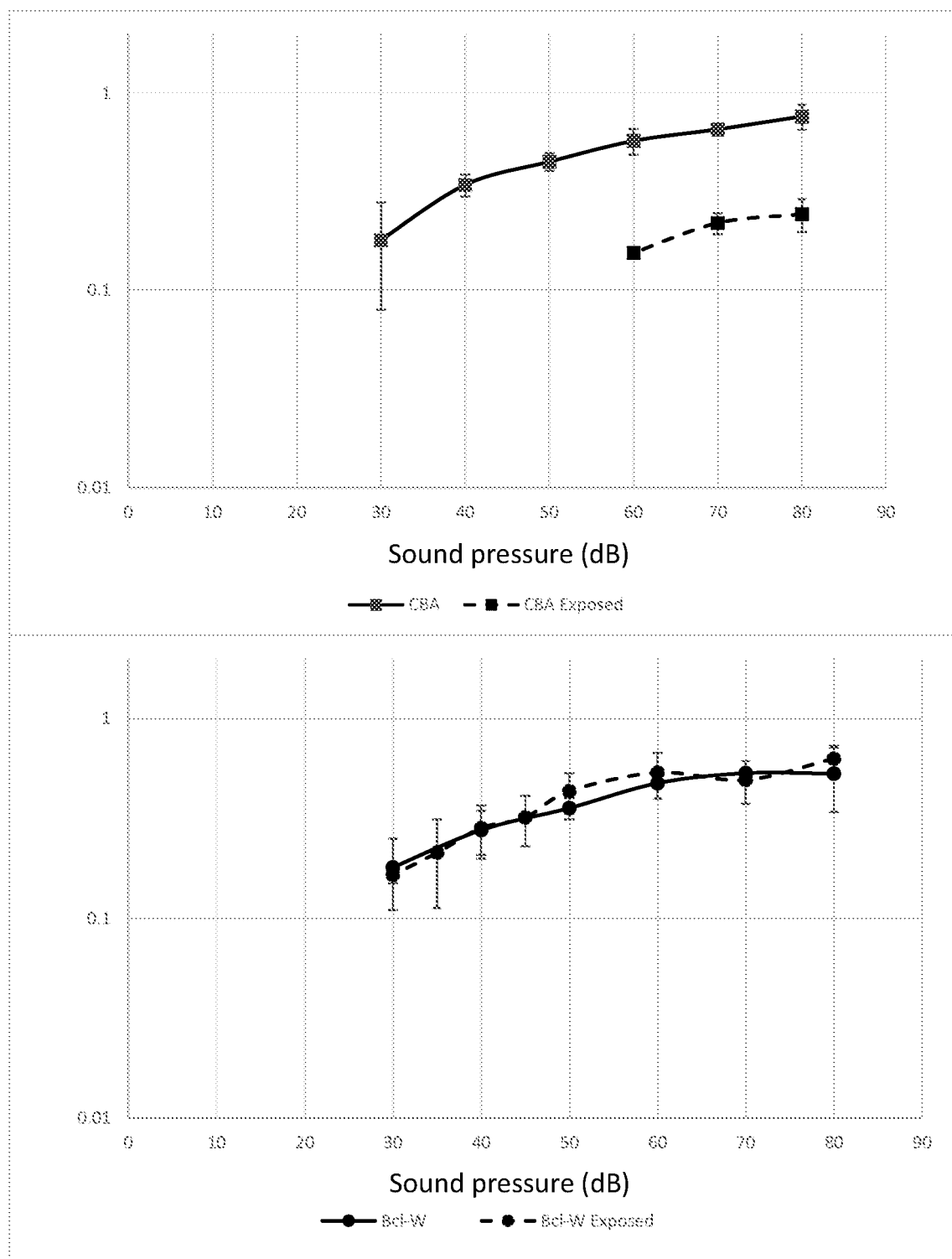
FIG. 13 is a graph depicting ABR Wave 1 amplitudes in the mice studied in Example 11.

The results from these tests are shown in FIGS. 11-13.

The salient findings are indicated below:

1. After noise exposure the CBA mice showed increased thresholds in the high frequency region of the cochlea (compare at 45 kHz).

2. In contrast, the mice that received bcl-w virus had preserved hearing at all frequencies.

3. Moreover, treatment with the virus did not affect baseline hearing (no threshold shift).

4. DPOAE thresholds were unchanged. This means that the noise exposure did not permanently damage the hair cells. This suggests that the preserved hearing in bcl-w treated animals reflects preservation of spiral ganglion neuron connections to inner hair cells in the high frequency region.

5. Consistent with this interpretation, CBA mice showed decreased wave 1 amplitudes in response to 45 kHz stimuli presented in 5 dB increments from 60 (the threshold) to 80 dB. In contrast, wave 1 amplitudes were unchanged in the bcl-w treated group.

Figure 14:
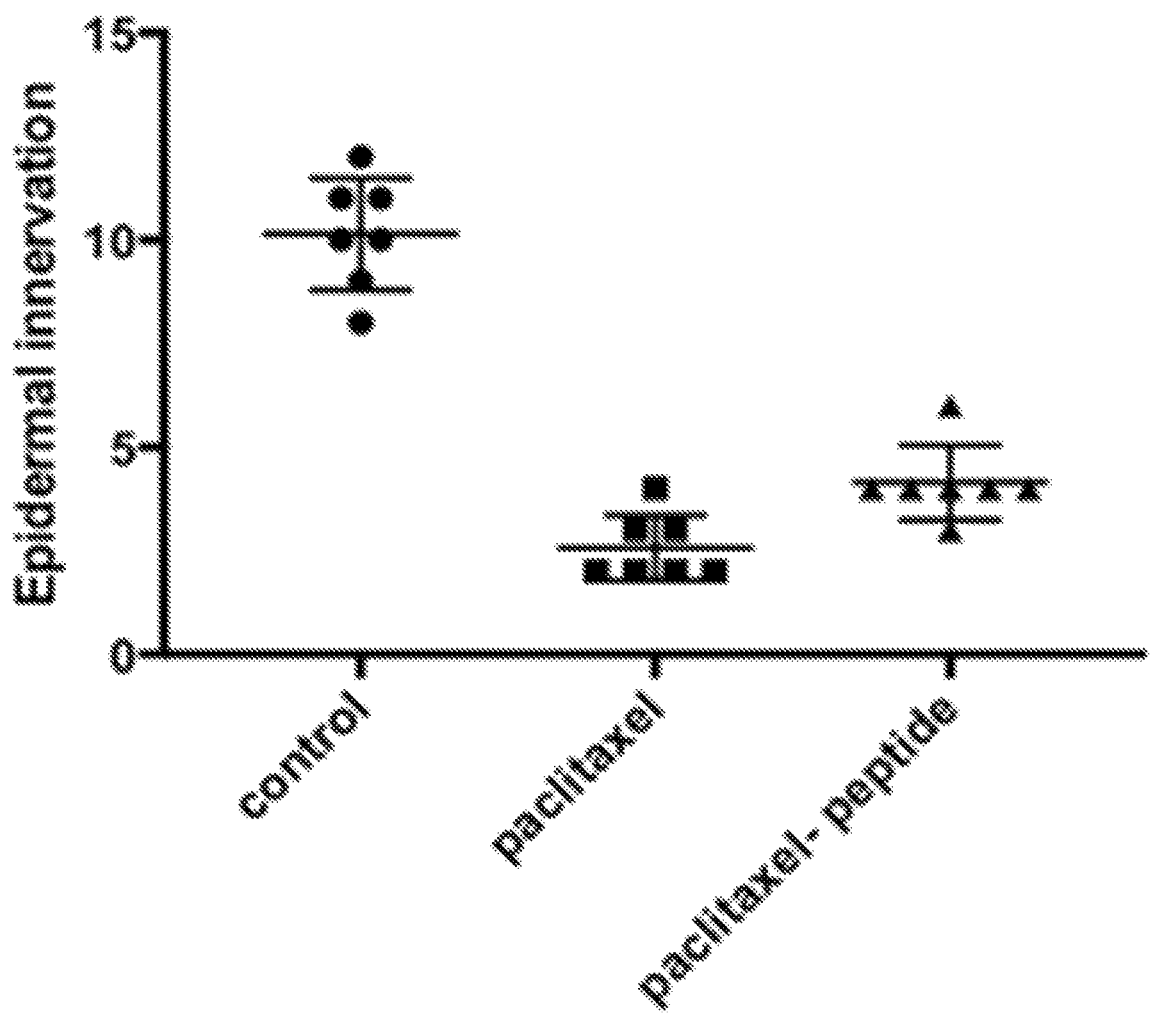
FIG. 14 is a graph showing that the loss of epidermal innervation in mice treated with paclitaxel is partially rescued upon pretreatment with Bclw-BH4 SAHB peptide.

Example 12: Bclw BH4-SAHB Partially Prevents Paclitaxel-Induced Loss of Innervation in Mice Mice treated with paclitaxel exhibit decreased thick skin epidermal innervation compared with control mice. Loss of epidermal innervation is partially rescued when Bclw-BH4 SAHB peptide is injected into the footpad 24 hrs prior to paclitaxel treatment (paclitaxel-peptide) (FIG. 14).

Figure 15:
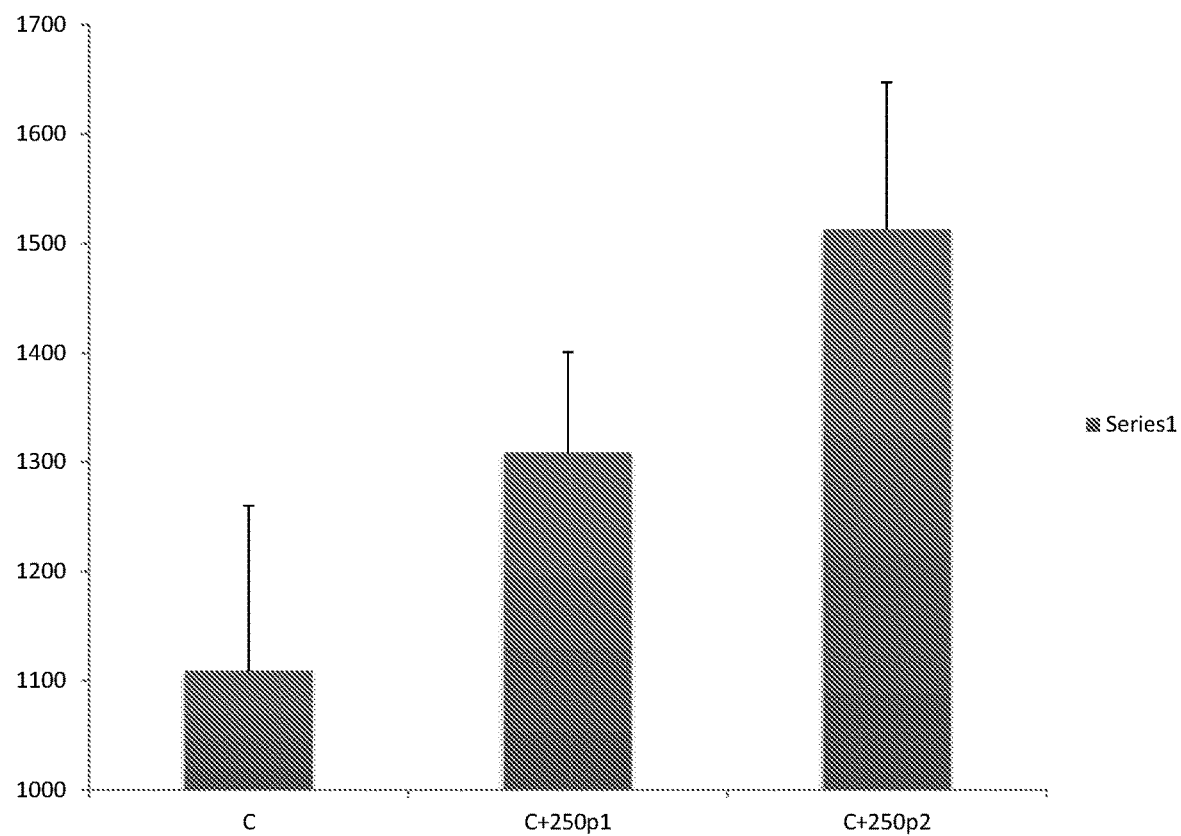
FIG. 15 is a bar graph showing the effect of pretreatment of paclitaxel treated human iPSC derived neurons with bclw peptide.

Example 13: Bclw BH4-SAHB Limits Paclitaxel-Induced Decrease in Axon Outgrowth in Human iPSC-Derived Neurons Human iPSC derived neurons were treated with paclitaxel. Pretreatment with Bclw BH4-SAHB (peptide 2) partially preserves axon length (FIG. 15).

OTHER ASPECTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

ic. Also provided are exemplary bclw mimetics.

What is claimed is:

1. A method of treating chemotherapy-induced peripheral neuropathy (CIPN) in a human subject in need thereof, the method comprising administering a therapeutically effective amount of a bclw mimetic to the human subject, wherein the bclw mimetic is an internally cross-linked polypeptide comprising the amino acid sequence of SEQ ID NO:31, wherein each X at positions 13 and 17 in SEQ ID NO: 31 is a non-natural amino acid containing an olefinic side chain that forms a hydrocarbon staple, and wherein the bclw mimetic binds Bax, and wherein the human subject has been administered a chemotherapeutic agent.

2. The method of claim 1, wherein the chemotherapeutic agent is an alkylating agent, an arabinoside, a proteasome inhibitor, a phosphatidylinositol 3-kinase (PI3K) inhibitor, or a rapidly accelerated fibrosarcoma (Raf) inhibitor.

3. The method of claim 1, wherein the chemotherapeutic agent is a microtubule-targeting agent.

4. The method of claim 1, wherein the bclw mimetic is administered to the human subject topically.

5. The method of claim 1, further comprising administering metformin to the human subject.

6. The method of claim 1, wherein each X at positions 13 and 17 in SEQ ID NO: 31 is (S)-2-(4-pentenyl)Ala-OH or each X at positions 13 and 17 in SEQ ID NO:31 is (R)-2-(4-pentenyl)Ala-OH.

7. The method of claim 1, wherein the bclw mimetic consists of the amino acid sequence of SEQ ID NO:31.

8. The method of claim 7, wherein each X at positions 13 and 17 in SEQ ID NO: 31 is (S)-2-(4-pentenyl)Ala-OH or each X at positions 13 and 17 in SEQ ID NO:31 is (R)-2-(4-pentenyl)Ala-OH.

9. The method of claim 1, wherein the human subject has:
(a) a hematological tumor selected from the group consisting of acute myeloid leukemia, chronic myeloid leukemia, Hodgkin lymphoma, non-Hodgkin lymphoma, multiple myeloma, acute lymphoblastic leukemia, and chronic lymphocytic leukemia; or
(b) a solid tumor selected from the group consisting of breast cancer, ovarian cancer, and lung cancer.

10. The method of claim 1, further comprising administering a chemotherapeutic agent to the human subject.

11. The method of claim 10, wherein the chemotherapeutic agent is selected from the group consisting of a microtubule-targeting agent, an alkylating agent, an antimetabolite, a folic acid analogue, a spindle poison, a platinum compound, an epipodophyllotoxin, an antibiotic, an epidermal growth factor receptor (EGF-R) inhibitor, an ephrin receptor (Eph-R) inhibitor, a p38/Janus kinase (p38/JAK) kinase inhibitor, a PI3K inhibitor, a mitogen-activated protein kinase kinase (MEK) inhibitor, a mitogen-activated protein kinase (MAPK) inhibitor, a tyrosine receptor kinase (Trk) inhibitor, a proteasome inhibitor, and a Raf inhibitor.

12. The method of claim 10, wherein the human subject has:
(i) a hematological tumor selected from the group consisting of acute myeloid leukemia, chronic myeloid leukemia, Hodgkin lymphoma, non-Hodgkin lymphoma, multiple myeloma, acute lymphoblastic leukemia, and chronic lymphocytic leukemia, or (ii) a solid tumor selected from the group consisting of breast cancer, ovarian cancer, and lung cancer.

13. The method of claim 10, wherein (i) the bclw mimetic is administered prior to the chemotherapeutic agent; (ii) the chemotherapeutic agent is administered prior to the bclw mimetic; (iii) the chemotherapeutic agent and the bclw mimetic are administered simultaneously; or (iv) the chemotherapeutic agent and the bclw mimetic are administered sequentially.

14. The method of claim 10, further comprising administering metformin to the human subject.

\* \* \* \* \*

UNITED STATES PATENT AND TRADEMARK OFFICE
CERTIFICATE OF CORRECTION

PATENT NO. : 11,466,064 B2
APPLICATION NO. : 16/326493
DATED : October 11, 2022
INVENTOR(S) : Rosalind Segal et al.

Page 1 of 1

It is certified that error appears in the above-identified patent and that said Letters Patent is hereby corrected as shown below:

In the Claims

Column 91, in Claim 1, Line 43:
Delete "belw" and insert -- bclw --.

Signed and Sealed this
Sixth Day of December, 2022

Katherine Kelly Vidal
*Director of the United States Patent and Trademark Office*

```
                        SEQUENCE LISTING

<160> NUMBER OF SEQ ID NOS: 54

<210> SEQ ID NO 1
<211> LENGTH: 193
<212> TYPE: PRT
<213> ORGANISM: Homo sapiens

<400> SEQUENCE: 1

Met Ala Thr Pro Ala Ser Ala Pro Asp Thr Arg Ala Leu Val Ala Asp
1               5                   10                  15

Phe Val Gly Tyr Lys Leu Arg Gln Lys Gly Tyr Val Cys Gly Ala Gly
            20                  25                  30

Pro Gly Glu Gly Pro Ala Ala Asp Pro Leu His Gln Ala Met Arg Ala
        35                  40                  45

Ala Gly Asp Glu Phe Glu Thr Arg Phe Arg Arg Thr Phe Ser Asp Leu
    50                  55                  60

Ala Ala Gln Leu His Val Thr Pro Gly Ser Ala Gln Gln Arg Phe Thr
65                  70                  75                  80

Gln Val Ser Asp Glu Leu Phe Gln Gly Gly Pro Asn Trp Gly Arg Leu
                85                  90                  95

Val Ala Phe Phe Val Phe Gly Ala Ala Leu Cys Ala Glu Ser Val Asn
            100                 105                 110

Lys Glu Met Glu Pro Leu Val Gly Gln Val Gln Glu Trp Met Val Ala
        115                 120                 125

Tyr Leu Glu Thr Arg Leu Ala Asp Trp Ile His Ser Ser Gly Gly Trp
    130                 135                 140

Ala Glu Phe Thr Ala Leu Tyr Gly Asp Gly Ala Leu Glu Glu Ala Arg
145                 150                 155                 160
```

```
Arg Leu Arg Glu Gly Asn Trp Ala Ser Val Arg Thr Val Leu Thr Gly
            165                 170                 175

Ala Val Ala Leu Gly Ala Leu Val Thr Val Gly Ala Phe Phe Ala Ser
        180                 185                 190

Lys

<210> SEQ ID NO 2
<211> LENGTH: 23
<212> TYPE: PRT
<213> ORGANISM: Homo sapiens

<400> SEQUENCE: 2

Asp Thr Arg Ala Leu Val Ala Asp Phe Val Gly Tyr Lys Leu Arg Gln
1               5                   10                  15

Lys Gly Tyr Val Cys Gly Ala
            20

<210> SEQ ID NO 3
<211> LENGTH: 21
<212> TYPE: PRT
<213> ORGANISM: Homo sapiens

<400> SEQUENCE: 3

Arg Ala Leu Val Ala Asp Phe Val Gly Tyr Lys Leu Arg Gln Lys Gly
1               5                   10                  15

Tyr Val Cys Gly Ala
            20

<210> SEQ ID NO 4
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<223> OTHER INFORMATION: See specification as filed for detailed
      description of substitutions and preferred embodiments
<220> FEATURE:
<221> NAME/KEY: MOD_RES
<222> LOCATION: (1)..(1)
<223> OTHER INFORMATION: non-natural amino acid containing an olefinic
      side chain that forms a hydrocarbon staple, (S)-2-(4-pentenyl)Ala-
      OH, or (R)-2-(4-pentenyl)Ala-OH; wherein Xaa1 forms a hydrocarbon
      staple with Xaa5
<220> FEATURE:
<221> NAME/KEY: MOD_RES
<222> LOCATION: (5)..(5)
<223> OTHER INFORMATION: non-natural amino acid containing an olefinic
      side chain that forms a hydrocarbon staple, (S)-2-(4-pentenyl)Ala-
      OH, or (R)-2-(4-pentenyl)Ala-OH; wherein Xaa1 forms a hydrocarbon
      staple with Xaa5

<400> SEQUENCE: 4

Xaa Ala Leu Val Xaa Asp Phe Val Gly Tyr Lys Leu Arg Gln Lys Gly
1               5                   10                  15

Tyr Val

<210> SEQ ID NO 5
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
```

<223> OTHER INFORMATION: See specification as filed for detailed
      description of substitutions and preferred embodiments
<220> FEATURE:
<221> NAME/KEY: MOD_RES
<222> LOCATION: (2)..(2)
<223> OTHER INFORMATION: non-natural amino acid containing an olefinic
      side chain that forms a hydrocarbon staple, (S)-2-(4-pentenyl)Ala-
      OH, or (R)-2-(4-pentenyl)Ala-OH; wherein Xaa2 forms a hydrocarbon
      staple with Xaa6
<220> FEATURE:
<221> NAME/KEY: MOD_RES
<222> LOCATION: (6)..(6)
<223> OTHER INFORMATION: non-natural amino acid containing an olefinic
      side chain that forms a hydrocarbon staple, (S)-2-(4-pentenyl)Ala-
      OH, or (R)-2-(4-pentenyl)Ala-OH; wherein Xaa2 forms a hydrocarbon
      staple with Xaa6

<400> SEQUENCE: 5

Arg Xaa Leu Val Ala Xaa Phe Val Gly Tyr Lys Leu Arg Gln Lys Gly
1               5                   10                  15

Tyr Val

<210> SEQ ID NO 6
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<223> OTHER INFORMATION: See specification as filed for detailed
      description of substitutions and preferred embodiments
<220> FEATURE:
<221> NAME/KEY: MOD_RES
<222> LOCATION: (3)..(3)
<223> OTHER INFORMATION: non-natural amino acid containing an olefinic
      side chain that forms a hydrocarbon staple, (S)-2-(4-pentenyl)Ala-
      OH, or (R)-2-(4-pentenyl)Ala-OH; wherein Xaa3 forms a hydrocarbon
      staple with Xaa7
<220> FEATURE:
<221> NAME/KEY: MOD_RES
<222> LOCATION: (7)..(7)
<223> OTHER INFORMATION: non-natural amino acid containing an olefinic
      side chain that forms a hydrocarbon staple, (S)-2-(4-pentenyl)Ala-
      OH, or (R)-2-(4-pentenyl)Ala-OH; wherein Xaa3 forms a hydrocarbon
      staple with Xaa7

<400> SEQUENCE: 6

Arg Ala Xaa Val Ala Asp Xaa Val Gly Tyr Lys Leu Arg Gln Lys Gly
1               5                   10                  15

Tyr Val

<210> SEQ ID NO 7
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<223> OTHER INFORMATION: See specification as filed for detailed
      description of substitutions and preferred embodiments
<220> FEATURE:
<221> NAME/KEY: MOD_RES
<222> LOCATION: (4)..(4)
<223> OTHER INFORMATION: non-natural amino acid containing an olefinic
      side chain that forms a hydrocarbon staple, (S)-2-(4-pentenyl)Ala-
      OH, or (R)-2-(4-pentenyl)Ala-OH; wherein Xaa4 forms a hydrocarbon
      staple with Xaa8
<220> FEATURE:
<221> NAME/KEY: MOD_RES
<222> LOCATION: (8)..(8)
<223> OTHER INFORMATION: non-natural amino acid containing an olefinic -continued

```
        side chain that forms a hydrocarbon staple, (S)-2-(4-pentenyl)Ala-
        OH, or (R)-2-(4-pentenyl)Ala-OH; wherein Xaa4 forms a hydrocarbon
        staple with Xaa8

<400> SEQUENCE: 7

Arg Ala Leu Xaa Ala Asp Phe Xaa Gly Tyr Lys Leu Arg Gln Lys Gly
1               5                   10                  15

Tyr Val

<210> SEQ ID NO 8
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<223> OTHER INFORMATION: See specification as filed for detailed
        description of substitutions and preferred embodiments
<220> FEATURE:
<221> NAME/KEY: MOD_RES
<222> LOCATION: (5)..(5)
<223> OTHER INFORMATION: non-natural amino acid containing an olefinic
        side chain that forms a hydrocarbon staple, (S)-2-(4-pentenyl)Ala-
        OH, or (R)-2-(4-pentenyl)Ala-OH; wherein Xaa5 forms a hydrocarbon
        staple with Xaa9
<220> FEATURE:
<221> NAME/KEY: MOD_RES
<222> LOCATION: (9)..(9)
<223> OTHER INFORMATION: non-natural amino acid containing an olefinic
        side chain that forms a hydrocarbon staple, (S)-2-(4-pentenyl)Ala-
        OH, or (R)-2-(4-pentenyl)Ala-OH; wherein Xaa5 forms a hydrocarbon
        staple with Xaa9

<400> SEQUENCE: 8

Arg Ala Leu Val Xaa Asp Phe Val Xaa Tyr Lys Leu Arg Gln Lys Gly
1               5                   10                  15

Tyr Val

<210> SEQ ID NO 9
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<223> OTHER INFORMATION: See specification as filed for detailed
        description of substitutions and preferred embodiments
<220> FEATURE:
<221> NAME/KEY: MOD_RES
<222> LOCATION: (6)..(6)
<223> OTHER INFORMATION: non-natural amino acid containing an olefinic
        side chain that forms a hydrocarbon staple, (S)-2-(4-pentenyl)Ala-
        OH, or (R)-2-(4-pentenyl)Ala-OH; wherein Xaa6 forms a hydrocarbon
        staple with Xaa10
<220> FEATURE:
<221> NAME/KEY: MOD_RES
<222> LOCATION: (10)..(10)
<223> OTHER INFORMATION: non-natural amino acid containing an olefinic
        side chain that forms a hydrocarbon staple, (S)-2-(4-pentenyl)Ala-
        OH, or (R)-2-(4-pentenyl)Ala-OH; wherein Xaa6 forms a hydrocarbon
        staple with Xaa10

<400> SEQUENCE: 9

Arg Ala Leu Val Ala Xaa Phe Val Gly Xaa Lys Leu Arg Gln Lys Gly
1               5                   10                  15

Tyr Val

<210> SEQ ID NO 10
```

```
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<223> OTHER INFORMATION: See specification as filed for detailed
      description of substitutions and preferred embodiments
<220> FEATURE:
<221> NAME/KEY: MOD_RES
<222> LOCATION: (7)..(7)
<223> OTHER INFORMATION: non-natural amino acid containing an olefinic
      side chain that forms a hydrocarbon staple, (S)-2-(4-pentenyl)Ala-
      OH, or (R)-2-(4-pentenyl)Ala-OH; wherein Xaa7 forms a hydrocarbon
      staple with Xaa11
<220> FEATURE:
<221> NAME/KEY: MOD_RES
<222> LOCATION: (11)..(11)
<223> OTHER INFORMATION: non-natural amino acid containing an olefinic
      side chain that forms a hydrocarbon staple, (S)-2-(4-pentenyl)Ala-
      OH, or (R)-2-(4-pentenyl)Ala-OH; wherein Xaa7 forms a hydrocarbon
      staple with Xaa11

<400> SEQUENCE: 10

Arg Ala Leu Val Ala Asp Xaa Val Gly Tyr Xaa Leu Arg Gln Lys Gly
1               5                   10                  15

Tyr Val

<210> SEQ ID NO 11
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<223> OTHER INFORMATION: See specification as filed for detailed
      description of substitutions and preferred embodiments
<220> FEATURE:
<221> NAME/KEY: MOD_RES
<222> LOCATION: (8)..(8)
<223> OTHER INFORMATION: non-natural amino acid containing an olefinic
      side chain that forms a hydrocarbon staple, (S)-2-(4-pentenyl)Ala-
      OH, or (R)-2-(4-pentenyl)Ala-OH; wherein Xaa8 forms a hydrocarbon
      staple with Xaa12
<220> FEATURE:
<221> NAME/KEY: MOD_RES
<222> LOCATION: (12)..(12)
<223> OTHER INFORMATION: non-natural amino acid containing an olefinic
      side chain that forms a hydrocarbon staple, (S)-2-(4-pentenyl)Ala-
      OH, or (R)-2-(4-pentenyl)Ala-OH; wherein Xaa8 forms a hydrocarbon
      staple with Xaa12

<400> SEQUENCE: 11

Arg Ala Leu Val Ala Asp Phe Xaa Gly Tyr Lys Xaa Arg Gln Lys Gly
1               5                   10                  15

Tyr Val

<210> SEQ ID NO 12
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<223> OTHER INFORMATION: See specification as filed for detailed
      description of substitutions and preferred embodiments
<220> FEATURE:
<221> NAME/KEY: MOD_RES
<222> LOCATION: (9)..(9)
<223> OTHER INFORMATION: non-natural amino acid containing an olefinic
``` side chain that forms a hydrocarbon staple, (S)-2-(4-pentenyl)Ala-
OH, or (R)-2-(4-pentenyl)Ala-OH; wherein Xaa9 forms a hydrocarbon
staple with Xaa13
<220> FEATURE:
<221> NAME/KEY: MOD_RES
<222> LOCATION: (13)..(13)
<223> OTHER INFORMATION: non-natural amino acid containing an olefinic
side chain that forms a hydrocarbon staple, (S)-2-(4-pentenyl)Ala-
OH, or (R)-2-(4-pentenyl)Ala-OH; wherein Xaa9 forms a hydrocarbon
staple with Xaa13

<400> SEQUENCE: 12

Arg Ala Leu Val Ala Asp Phe Val Xaa Tyr Lys Leu Xaa Gln Lys Gly
1               5                   10                  15

Tyr Val

<210> SEQ ID NO 13
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<223> OTHER INFORMATION: See specification as filed for detailed
description of substitutions and preferred embodiments
<220> FEATURE:
<221> NAME/KEY: MOD_RES
<222> LOCATION: (10)..(10)
<223> OTHER INFORMATION: non-natural amino acid containing an olefinic
side chain that forms a hydrocarbon staple, (S)-2-(4-pentenyl)Ala-
OH, or (R)-2-(4-pentenyl)Ala-OH; wherein Xaa10 forms a hydrocarbon
staple with Xaa14
<220> FEATURE:
<221> NAME/KEY: MOD_RES
<222> LOCATION: (14)..(14)
<223> OTHER INFORMATION: non-natural amino acid containing an olefinic
side chain that forms a hydrocarbon staple, (S)-2-(4-pentenyl)Ala-
OH, or (R)-2-(4-pentenyl)Ala-OH; wherein Xaa10 forms a hydrocarbon
staple with Xaa14

<400> SEQUENCE: 13

Arg Ala Leu Val Ala Asp Phe Val Gly Xaa Lys Leu Arg Xaa Lys Gly
1               5                   10                  15

Tyr Val

<210> SEQ ID NO 14
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<223> OTHER INFORMATION: See specification as filed for detailed
description of substitutions and preferred embodiments
<220> FEATURE:
<221> NAME/KEY: MOD_RES
<222> LOCATION: (11)..(11)
<223> OTHER INFORMATION: non-natural amino acid containing an olefinic
side chain that forms a hydrocarbon staple, (S)-2-(4-pentenyl)Ala-
OH, or (R)-2-(4-pentenyl)Ala-OH; wherein Xaa11 forms a hydrocarbon
staple with Xaa15
<220> FEATURE:
<221> NAME/KEY: MOD_RES
<222> LOCATION: (15)..(15)
<223> OTHER INFORMATION: non-natural amino acid containing an olefinic
side chain that forms a hydrocarbon staple, (S)-2-(4-pentenyl)Ala-
OH, or (R)-2-(4-pentenyl)Ala-OH; wherein Xaa11 forms a hydrocarbon
staple with Xaa15

<400> SEQUENCE: 14

```
Arg Ala Leu Val Ala Asp Phe Val Gly Tyr Xaa Leu Arg Gln Xaa Gly
1               5                   10                  15

Tyr Val

<210> SEQ ID NO 15
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<223> OTHER INFORMATION: See specification as filed for detailed
      description of substitutions and preferred embodiments
<220> FEATURE:
<221> NAME/KEY: MOD_RES
<222> LOCATION: (12)..(12)
<223> OTHER INFORMATION: non-natural amino acid containing an olefinic
      side chain that forms a hydrocarbon staple, (S)-2-(4-pentenyl)Ala-
      OH, or (R)-2-(4-pentenyl)Ala-OH; wherein Xaa12 forms a hydrocarbon
      staple with Xaa16
<220> FEATURE:
<221> NAME/KEY: MOD_RES
<222> LOCATION: (16)..(16)
<223> OTHER INFORMATION: non-natural amino acid containing an olefinic
      side chain that forms a hydrocarbon staple, (S)-2-(4-pentenyl)Ala-
      OH, or (R)-2-(4-pentenyl)Ala-OH; wherein Xaa12 forms a hydrocarbon
      staple with Xaa16

<400> SEQUENCE: 15

Arg Ala Leu Val Ala Asp Phe Val Gly Tyr Lys Xaa Arg Gln Lys Xaa
1               5                   10                  15

Tyr Val

<210> SEQ ID NO 16
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<223> OTHER INFORMATION: See specification as filed for detailed
      description of substitutions and preferred embodiments
<220> FEATURE:
<221> NAME/KEY: MOD_RES
<222> LOCATION: (13)..(13)
<223> OTHER INFORMATION: non-natural amino acid containing an olefinic
      side chain that forms a hydrocarbon staple, (S)-2-(4-pentenyl)Ala-
      OH, or (R)-2-(4-pentenyl)Ala-OH; wherein Xaa13 forms a hydrocarbon
      staple with Xaa17
<220> FEATURE:
<221> NAME/KEY: MOD_RES
<222> LOCATION: (17)..(17)
<223> OTHER INFORMATION: non-natural amino acid containing an olefinic
      side chain that forms a hydrocarbon staple, (S)-2-(4-pentenyl)Ala-
      OH, or (R)-2-(4-pentenyl)Ala-OH; wherein Xaa13 forms a hydrocarbon
      staple with Xaa17

<400> SEQUENCE: 16

Arg Ala Leu Val Ala Asp Phe Val Gly Tyr Lys Leu Xaa Gln Lys Gly
1               5                   10                  15

Xaa Val

<210> SEQ ID NO 17
<211> LENGTH: 18
<212> TYPE: PRT
<213> ORGANISM: Artificial Sequence
<220> FEATURE:
<223> OTHER INFORMATION: Synthetic peptide
<220> FEATURE:
```

```
<221> NAME/KEY: misc_feature
<223> OTHER INFORMATION: See specification as filed for detailed
      description of substitutions and preferred embodiments
<220> FEATURE:
<221> NAME/KEY: MOD_RES
<222> LOCATION: (14)..(14)
<223> OTHER INFORMATION: non-natural amino acid containing an olefinic
      side chain that forms a hydrocarbon staple, (S)-2-(4-pentenyl)Ala-
      OH, or (R)-2-(4-pentenyl)Ala-OH; wherein Xaa14 forms a hydrocarbon
      staple with Xaa18
<220> FEATURE:
<221> NAME/KEY: MOD_RES
<222> LOCATION: (18)..(18)
<223> OTHER INFORMATION: non-natural amino acid containing an olefinic
      side chain that forms a hydrocarbon staple, (S)-2-(4-pentenyl)Ala-
      OH, or (R)-2-(4-pentenyl)Ala-OH; wherein Xaa14 forms a hydrocarbon
      staple with Xaa18

<400> SEQUENCE: 17

Arg Ala Leu Val Ala Asp Phe Val Gly Tyr Lys Leu Arg Xaa Lys Gly
1               5                   10                  15

Tyr Xaa

<210> SEQ ID NO 18
<211> LENGTH: 19
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<223> OTHER INFORMATION: See specification as filed for detailed
      description of substitutions and preferred embodiments
<220> FEATURE:
<221> NAME/KEY: MOD_RES
<222> LOCATION: (15)..(15)
<223> OTHER INFORMATION: non-natural amino acid containing an olefinic
      side chain that forms a hydrocarbon staple, (S)-2-(4-pentenyl)Ala-
      OH, or (R)-2-(4-pentenyl)Ala-OH; wherein Xaa15 forms a hydrocarbon
      staple with Xaa19
<220> FEATURE:
<221> NAME/KEY: MOD_RES
<222> LOCATION: (19)..(19)
<223> OTHER INFORMATION: non-natural amino acid containing an olefinic
      side chain that forms a hydrocarbon staple, (S)-2-(4-pentenyl)Ala-
      OH, or (R)-2-(4-pentenyl)Ala-OH; wherein Xaa15 forms a hydrocarbon
      staple with Xaa19

<400> SEQUENCE: 18

Arg Ala Leu Val Ala Asp Phe Val Gly Tyr Lys Leu Arg Gln Xaa Gly
1               5                   10                  15

Tyr Val Xaa

<210> SEQ ID NO 19
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<223> OTHER INFORMATION: See specification as filed for detailed
      description of substitutions and preferred embodiments
<220> FEATURE:
<221> NAME/KEY: MOD_RES
<222> LOCATION: (1)..(1)
<223> OTHER INFORMATION: non-natural amino acid containing an olefinic
      side chain that forms a hydrocarbon staple, (R or S)-2-(7-
      octenyl)Ala-OH, or (R or S)-2-(4-pentenyl)Ala-OH; wherein Xaa1
      forms a hydrocarbon staple with Xaa8
<220> FEATURE:
<221> NAME/KEY: MOD_RES
<222> LOCATION: (8)..(8)
```

```
<223> OTHER INFORMATION: non-natural amino acid containing an olefinic
      side chain that forms a hydrocarbon staple, (R or S)-2-(7-
      octenyl)Ala-OH, or (R or S)-2-(4-pentenyl)Ala-OH; wherein Xaa1
      forms a hydrocarbon staple with Xaa8

<400> SEQUENCE: 19

Xaa Ala Leu Val Ala Asp Phe Xaa Gly Tyr Lys Leu Arg Gln Lys Gly
1               5                   10                  15

Tyr Val

<210> SEQ ID NO 20
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<223> OTHER INFORMATION: See specification as filed for detailed
      description of substitutions and preferred embodiments
<220> FEATURE:
<221> NAME/KEY: MOD_RES
<222> LOCATION: (2)..(2)
<223> OTHER INFORMATION: non-natural amino acid containing an olefinic
      side chain that forms a hydrocarbon staple, (R or S)-2-(7-
      octenyl)Ala-OH, or (R or S)-2-(4-pentenyl)Ala-OH; wherein Xaa2
      forms a hydrocarbon staple with Xaa9
<220> FEATURE:
<221> NAME/KEY: MOD_RES
<222> LOCATION: (9)..(9)
<223> OTHER INFORMATION: non-natural amino acid containing an olefinic
      side chain that forms a hydrocarbon staple, (R or S)-2-(7-
      octenyl)Ala-OH, or (R or S)-2-(4-pentenyl)Ala-OH; wherein Xaa2
      forms a hydrocarbon staple with Xaa9

<400> SEQUENCE: 20

Arg Xaa Leu Val Ala Asp Phe Val Xaa Tyr Lys Leu Arg Gln Lys Gly
1               5                   10                  15

Tyr Val

<210> SEQ ID NO 21
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<223> OTHER INFORMATION: See specification as filed for detailed
      description of substitutions and preferred embodiments
<220> FEATURE:
<221> NAME/KEY: MOD_RES
<222> LOCATION: (3)..(3)
<223> OTHER INFORMATION: non-natural amino acid containing an olefinic
      side chain that forms a hydrocarbon staple, (R or S)-2-(7-
      octenyl)Ala-OH, or (R or S)-2-(4-pentenyl)Ala-OH; wherein Xaa3
      forms a hydrocarbon staple with Xaa10
<220> FEATURE:
<221> NAME/KEY: MOD_RES
<222> LOCATION: (10)..(10)
<223> OTHER INFORMATION: non-natural amino acid containing an olefinic
      side chain that forms a hydrocarbon staple, (R or S)-2-(7-
      octenyl)Ala-OH, or (R or S)-2-(4-pentenyl)Ala-OH; wherein Xaa3
      forms a hydrocarbon staple with Xaa10

<400> SEQUENCE: 21

Arg Ala Xaa Val Ala Asp Phe Val Gly Xaa Lys Leu Arg Gln Lys Gly
1               5                   10                  15

Tyr Val
```

-continued

```
<210> SEQ ID NO 22
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<223> OTHER INFORMATION: See specification as filed for detailed
      description of substitutions and preferred embodiments
<220> FEATURE:
<221> NAME/KEY: MOD_RES
<222> LOCATION: (4)..(4)
<223> OTHER INFORMATION: non-natural amino acid containing an olefinic
      side chain that forms a hydrocarbon staple, (R or S)-2-(7-
      octenyl)Ala-OH, or (R or S)-2-(4-pentenyl)Ala-OH; wherein Xaa4
      forms a hydrocarbon staple with Xaa11
<220> FEATURE:
<221> NAME/KEY: MOD_RES
<222> LOCATION: (11)..(11)
<223> OTHER INFORMATION: non-natural amino acid containing an olefinic
      side chain that forms a hydrocarbon staple, (R or S)-2-(7-
      octenyl)Ala-OH, or (R or S)-2-(4-pentenyl)Ala-OH; wherein Xaa4
      forms a hydrocarbon staple with Xaa11

<400> SEQUENCE: 22

Arg Ala Leu Xaa Ala Asp Phe Val Gly Tyr Xaa Leu Arg Gln Lys Gly
1               5                   10                  15

Tyr Val

<210> SEQ ID NO 23
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<223> OTHER INFORMATION: See specification as filed for detailed
      description of substitutions and preferred embodiments
<220> FEATURE:
<221> NAME/KEY: MOD_RES
<222> LOCATION: (5)..(5)
<223> OTHER INFORMATION: non non-natural amino acid containing an
      olefinic side chain that forms a hydrocarbon staple, (R or S)-2-
      (7-octenyl)Ala-OH, or (R or S)-2-(4-pentenyl)Ala-OH; wherein Xaa5
      forms a hydrocarbon staple with Xaa12
<220> FEATURE:
<221> NAME/KEY: MOD_RES
<222> LOCATION: (12)..(12)
<223> OTHER INFORMATION: non-natural amino acid containing an olefinic
      side chain that forms a hydrocarbon staple, (R or S)-2-(7-
      octenyl)Ala-OH, or (R or S)-2-(4-pentenyl)Ala-OH; wherein Xaa5
      forms a hydrocarbon staple with Xaa12

<400> SEQUENCE: 23

Arg Ala Leu Val Xaa Asp Phe Val Gly Tyr Lys Xaa Arg Gln Lys Gly
1               5                   10                  15

Tyr Val

<210> SEQ ID NO 24
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<223> OTHER INFORMATION: See specification as filed for detailed
      description of substitutions and preferred embodiments
<220> FEATURE:
<221> NAME/KEY: MOD_RES
<222> LOCATION: (6)..(6)
```

```
<223> OTHER INFORMATION: non-natural amino acid containing an olefinic
      side chain that forms a hydrocarbon staple, (R or S)-2-(7-
      octenyl)Ala-OH, or (R or S)-2-(4-pentenyl)Ala-OH; wherein Xaa6
      forms a hydrocarbon staple with Xaa13
<220> FEATURE:
<221> NAME/KEY: MOD_RES
<222> LOCATION: (13)..(13)
<223> OTHER INFORMATION: non-natural amino acid containing an olefinic
      side chain that forms a hydrocarbon staple, (R or S)-2-(7-
      octenyl)Ala-OH, or (R or S)-2-(4-pentenyl)Ala-OH; wherein Xaa6
      forms a hydrocarbon staple with Xaa13

<400> SEQUENCE: 24

Arg Ala Leu Val Ala Xaa Phe Val Gly Tyr Lys Leu Xaa Gln Lys Gly
1               5                   10                  15

Tyr Val

<210> SEQ ID NO 25
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<223> OTHER INFORMATION: See specification as filed for detailed
      description of substitutions and preferred embodiments
<220> FEATURE:
<221> NAME/KEY: MOD_RES
<222> LOCATION: (7)..(7)
<223> OTHER INFORMATION: non-natural amino acid containing an olefinic
      side chain that forms a hydrocarbon staple, (R or S)-2-(7-
      octenyl)Ala-OH, or (R or S)-2-(4-pentenyl)Ala-OH; wherein Xaa7
      forms a hydrocarbon staple with Xaa14
<220> FEATURE:
<221> NAME/KEY: MOD_RES
<222> LOCATION: (14)..(14)
<223> OTHER INFORMATION: non-natural amino acid containing an olefinic
      side chain that forms a hydrocarbon staple, (R or S)-2-(7-
      octenyl)Ala-OH, or (R or S)-2-(4-pentenyl)Ala-OH; wherein Xaa7
      forms a hydrocarbon staple with Xaa14

<400> SEQUENCE: 25

Arg Ala Leu Val Ala Asp Xaa Val Gly Tyr Lys Leu Arg Xaa Lys Gly
1               5                   10                  15

Tyr Val

<210> SEQ ID NO 26
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<223> OTHER INFORMATION: See specification as filed for detailed
      description of substitutions and preferred embodiments
<220> FEATURE:
<221> NAME/KEY: MOD_RES
<222> LOCATION: (8)..(8)
<223> OTHER INFORMATION: non-natural amino acid containing an olefinic
      side chain that forms a hydrocarbon staple, (R or S)-2-(7-
      octenyl)Ala-OH, or (R or S)-2-(4-pentenyl)Ala-OH; wherein Xaa8
      forms a hydrocarbon staple with Xaa15
<220> FEATURE:
<221> NAME/KEY: MOD_RES
<222> LOCATION: (15)..(15)
<223> OTHER INFORMATION: non-natural amino acid containing an olefinic
      side chain that forms a hydrocarbon staple, (R or S)-2-(7-
      octenyl)Ala-OH, or (R or S)-2-(4-pentenyl)Ala-OH; wherein Xaa8
      forms a hydrocarbon staple with Xaa15

<400> SEQUENCE: 26
```

Arg Ala Leu Val Ala Asp Phe Xaa Gly Tyr Lys Leu Arg Gln Xaa Gly
1               5                   10                  15

Tyr Val

<210> SEQ ID NO 27
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<223> OTHER INFORMATION: See specification as filed for detailed
      description of substitutions and preferred embodiments
<220> FEATURE:
<221> NAME/KEY: MOD_RES
<222> LOCATION: (9)..(9)
<223> OTHER INFORMATION: non-natural amino acid containing an olefinic
      side chain that forms a hydrocarbon staple, (R or S)-2-(7-
      octenyl)Ala-OH, or (R or S)-2-(4-pentenyl)Ala-OH; wherein Xaa9
      forms a hydrocarbon staple with Xaa16
<220> FEATURE:
<221> NAME/KEY: MOD_RES
<222> LOCATION: (16)..(16)
<223> OTHER INFORMATION: non-natural amino acid containing an olefinic
      side chain that forms a hydrocarbon staple, (R or S)-2-(7-
      octenyl)Ala-OH, or (R or S)-2-(4-pentenyl)Ala-OH; wherein Xaa9
      forms a hydrocarbon staple with Xaa16

<400> SEQUENCE: 27

Arg Ala Leu Val Ala Asp Phe Val Xaa Tyr Lys Leu Arg Gln Lys Xaa
1               5                   10                  15

Tyr Val

<210> SEQ ID NO 28
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<223> OTHER INFORMATION: See specification as filed for detailed
      description of substitutions and preferred embodiments
<220> FEATURE:
<221> NAME/KEY: MOD_RES
<222> LOCATION: (10)..(10)
<223> OTHER INFORMATION: non-natural amino acid containing an olefinic
      side chain that forms a hydrocarbon staple, (R or S)-2-(7-
      octenyl)Ala-OH, or (R or S)-2-(4-pentenyl)Ala-OH; wherein Xaa10
      forms a hydrocarbon staple with Xaa17
<220> FEATURE:
<221> NAME/KEY: MOD_RES
<222> LOCATION: (17)..(17)
<223> OTHER INFORMATION: non-natural amino acid containing an olefinic
      side chain that forms a hydrocarbon staple, (R or S)-2-(7-
      octenyl)Ala-OH, or (R or S)-2-(4-pentenyl)Ala-OH; wherein Xaa10
      forms a hydrocarbon staple with Xaa17

<400> SEQUENCE: 28

Arg Ala Leu Val Ala Asp Phe Val Gly Xaa Lys Leu Arg Gln Lys Gly
1               5                   10                  15

Xaa Val

<210> SEQ ID NO 29
<211> LENGTH: 18
<212> TYPE: PRT
<213> ORGANISM: Artificial Sequence
<220> FEATURE:
<223> OTHER INFORMATION: Synthetic peptide

```
<220> FEATURE:
<221> NAME/KEY: misc_feature
<223> OTHER INFORMATION: See specification as filed for detailed
      description of substitutions and preferred embodiments
<220> FEATURE:
<221> NAME/KEY: MOD_RES
<222> LOCATION: (11)..(11)
<223> OTHER INFORMATION: non-natural amino acid containing an olefinic
      side chain that forms a hydrocarbon staple, (R or S)-2-(7-
      octenyl)Ala-OH, or (R or S)-2-(4-pentenyl)Ala-OH; wherein Xaa11
      forms a hydrocarbon staple with Xaa18
<220> FEATURE:
<221> NAME/KEY: MOD_RES
<222> LOCATION: (18)..(18)
<223> OTHER INFORMATION: non-natural amino acid containing an olefinic
      side chain that forms a hydrocarbon staple, (R or S)-2-(7-
      octenyl)Ala-OH, or (R or S)-2-(4-pentenyl)Ala-OH; wherein Xaa11
      forms a hydrocarbon staple with Xaa18

<400> SEQUENCE: 29

Arg Ala Leu Val Ala Asp Phe Val Gly Tyr Xaa Leu Arg Gln Lys Gly
1               5                   10                  15

Tyr Xaa

<210> SEQ ID NO 30
<211> LENGTH: 19
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<223> OTHER INFORMATION: See specification as filed for detailed
      description of substitutions and preferred embodiments
<220> FEATURE:
<221> NAME/KEY: MOD_RES
<222> LOCATION: (12)..(12)
<223> OTHER INFORMATION: non-natural amino acid containing an olefinic
      side chain that forms a hydrocarbon staple, (R or S)-2-(7-
      octenyl)Ala-OH, or (R or S)-2-(4-pentenyl)Ala-OH; wherein Xaa12
      forms a hydrocarbon staple with Xaa19
<220> FEATURE:
<221> NAME/KEY: MOD_RES
<222> LOCATION: (19)..(19)
<223> OTHER INFORMATION: non-natural amino acid containing an olefinic
      side chain that forms a hydrocarbon staple, (R or S)-2-(7-
      octenyl)Ala-OH, or (R or S)-2-(4-pentenyl)Ala-OH; wherein Xaa12
      forms a hydrocarbon staple with Xaa19

<400> SEQUENCE: 30

Arg Ala Leu Val Ala Asp Phe Val Gly Tyr Lys Xaa Arg Gln Lys Gly
1               5                   10                  15

Tyr Val Xaa

<210> SEQ ID NO 31
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<223> OTHER INFORMATION: See specification as filed for detailed
      description of substitutions and preferred embodiments
<220> FEATURE:
<221> NAME/KEY: MOD_RES
<222> LOCATION: (13)..(13)
<223> OTHER INFORMATION: non-natural amino acid containing an olefinic
      side chain that forms a hydrocarbon staple, (S)-2-(4-pentenyl)Ala-
      OH, or (R)-2-(4-pentenyl)Ala-OH; wherein Xaa13 forms a hydrocarbon
      staple with Xaa17
<220> FEATURE:
<221> NAME/KEY: MOD_RES
```

```
<222> LOCATION: (17)..(17)
<223> OTHER INFORMATION: non-natural amino acid containing an olefinic
      side chain that forms a hydrocarbon staple, (S)-2-(4-pentenyl)Ala-
      OH, or (R)-2-(4-pentenyl)Ala-OH; wherein Xaa13 forms a hydrocarbon
      staple with Xaa17
<220> FEATURE:
<221> NAME/KEY: MOD_RES
<222> LOCATION: (18)..(18)
<223> OTHER INFORMATION: Norleucine

<400> SEQUENCE: 31

Ala Leu Val Ala Asp Phe Val Gly Tyr Lys Leu Arg Xaa Lys Gly Tyr
1               5                   10                  15

Xaa Xaa Gly Ala
            20

<210> SEQ ID NO 32
<211> LENGTH: 21
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<223> OTHER INFORMATION: See specification as filed for detailed
      description of substitutions and preferred embodiments
<220> FEATURE:
<221> NAME/KEY: MOD_RES
<222> LOCATION: (14)..(14)
<223> OTHER INFORMATION: non-natural amino acid containing an olefinic
      side chain that forms a hydrocarbon staple, (S)-2-(4-pentenyl)Ala-
      OH, or (R)-2-(4-pentenyl)Ala-OH; wherein Xaa14 forms a hydrocarbon
      staple with Xaa18
<220> FEATURE:
<221> NAME/KEY: MOD_RES
<222> LOCATION: (18)..(18)
<223> OTHER INFORMATION: non-natural amino acid containing an olefinic
      side chain that forms a hydrocarbon staple, (S)-2-(4-pentenyl)Ala-
      OH, or (R)-2-(4-pentenyl)Ala-OH; wherein Xaa14 forms a hydrocarbon
      staple with Xaa18
<220> FEATURE:
<221> NAME/KEY: MOD_RES
<222> LOCATION: (19)..(19)
<223> OTHER INFORMATION: Norleucine

<400> SEQUENCE: 32

Arg Ala Leu Val Ala Asp Phe Val Gly Tyr Lys Leu Arg Xaa Lys Gly
1               5                   10                  15

Tyr Xaa Xaa Gly Ala
            20

<210> SEQ ID NO 33
<211> LENGTH: 5
<212> TYPE: PRT
<213> ORGANISM: Artificial Sequence
<220> FEATURE:
<223> OTHER INFORMATION: Synthetic peptide

<400> SEQUENCE: 33

Gly Gly Gly Gly Ser
1               5

<210> SEQ ID NO 34
<211> LENGTH: 50
<212> TYPE: PRT
<213> ORGANISM: Homo sapiens

<400> SEQUENCE: 34

Met Ala His Ala Gly Arg Thr Gly Tyr Asp Asn Arg Glu Ile Val Met
1               5                   10                  15
```

Lys Tyr Ile His Tyr Lys Leu Ser Gln Arg Gly Tyr Glu Trp Asp Ala
            20                  25                  30

Gly Asp Val Gly Ala Ala Pro Pro Gly Ala Ala Pro Ala Pro Gly Ile
        35                  40                  45

Phe Ser
    50

<210> SEQ ID NO 35
<211> LENGTH: 40
<212> TYPE: PRT
<213> ORGANISM: Homo sapiens

<400> SEQUENCE: 35

Met Ser Gln Ser Asn Arg Glu Leu Val Val Asp Phe Leu Ser Tyr Lys
1               5                   10                  15

Leu Ser Gln Lys Gly Tyr Ser Trp Ser Gln Phe Ser Asp Val Glu Glu
            20                  25                  30

Asn Arg Thr Glu Ala Pro Glu Gly
        35                  40

<210> SEQ ID NO 36
<211> LENGTH: 40
<212> TYPE: PRT
<213> ORGANISM: Homo sapiens

<400> SEQUENCE: 36

Met Ala Thr Pro Ala Ser Ala Pro Asp Thr Arg Ala Leu Val Ala Asp
1               5                   10                  15

Phe Val Gly Tyr Lys Leu Arg Gln Lys Gly Tyr Val Cys Gly Ala Gly
            20                  25                  30

Pro Gly Glu Gly Pro Ala Ala Asp
        35                  40

<210> SEQ ID NO 37
<211> LENGTH: 84
<212> TYPE: DNA
<213> ORGANISM: Artificial Sequence
<220> FEATURE:
<223> OTHER INFORMATION: Synthetic oligonucleotide

<400> SEQUENCE: 37
gctctgaacc tccccatgac ttaaatccgt tgctctttct tggccctgcc cagtgcctct     60
gagcatttca cctatctcag gagc                                           84

<210> SEQ ID NO 38
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 38
cgatcgtaat cacccgagtg tgatcatctg gtcgctgggg aatgagtcag gccacgg       57

<210> SEQ ID NO 39
<211> LENGTH: 20
<212> TYPE: DNA
<213> ORGANISM: Artificial Sequence
<220> FEATURE:
<223> OTHER INFORMATION: Synthetic primer

<400> SEQUENCE: 39
agcctcaacc ccagacacac                                                    20

<210> SEQ ID NO 40
<211> LENGTH: 21
<212> TYPE: DNA
<213> ORGANISM: Artificial Sequence
<220> FEATURE:
<223> OTHER INFORMATION: Synthetic primer

<400> SEQUENCE: 40
tcacttgcta gcaaaaaagg c                                                  21

<210> SEQ ID NO 41
<211> LENGTH: 40
<212> TYPE: DNA
<213> ORGANISM: Artificial Sequence
<220> FEATURE:
<223> OTHER INFORMATION: Synthetic primer

<400> SEQUENCE: 41
taatacgact cactatagga cagttaccag ggcccccagt                               40

<210> SEQ ID NO 42
<211> LENGTH: 22
<212> TYPE: DNA
<213> ORGANISM: Artificial Sequence
<220> FEATURE:
<223> OTHER INFORMATION: Synthetic primer

<400> SEQUENCE: 42
tcagaaggac tcctacgtgg gc                                                 22

<210> SEQ ID NO 43
<211> LENGTH: 20
<212> TYPE: DNA
<213> ORGANISM: Artificial Sequence
<220> FEATURE:
<223> OTHER INFORMATION: Synthetic primer

<400> SEQUENCE: 43
aggtccagac gcaggatggc                                                    20

<210> SEQ ID NO 44
<211> LENGTH: 26
<212> TYPE: DNA
<213> ORGANISM: Artificial Sequence
<220> FEATURE:
<223> OTHER INFORMATION: Synthetic primer

<400> SEQUENCE: 44
taatacgact cactaaccct catagc                                             26

<210> SEQ ID NO 45
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 45
taatacgact cactataggg                                                    20

<210> SEQ ID NO 46
<211> LENGTH: 20
<212> TYPE: PRT

```
<213> ORGANISM: Homo sapiens

<400> SEQUENCE: 46

Ala Leu Val Ala Asp Phe Val Gly Tyr Lys Leu Arg Gln Lys Gly Tyr
1               5                   10                  15

Val Cys Gly Ala
            20

<210> SEQ ID NO 47
<211> LENGTH: 16
<212> TYPE: PRT
<213> ORGANISM: Homo sapiens

<400> SEQUENCE: 47

Thr Arg Ala Leu Val Ala Asp Phe Val Gly Tyr Lys Leu Arg Gln Lys
1               5                   10                  15

<210> SEQ ID NO 48
<211> LENGTH: 18
<212> TYPE: PRT
<213> ORGANISM: Homo sapiens

<400> SEQUENCE: 48

Arg Ala Leu Val Ala Asp Phe Val Gly Tyr Lys Leu Arg Gln Lys Gly
1               5                   10                  15

Tyr Val

<210> SEQ ID NO 49
<211> LENGTH: 17
<212> TYPE: PRT
<213> ORGANISM: Homo sapiens

<400> SEQUENCE: 49

Ala Leu Val Ala Asp Phe Val Gly Tyr Lys Leu Arg Gln Lys Gly Tyr
1               5                   10                  15

Val

<210> SEQ ID NO 50
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<223> OTHER INFORMATION: See specification as filed for detailed
      description of substitutions and preferred embodiments
<220> FEATURE:
<221> NAME/KEY: MOD_RES
<222> LOCATION: (13)..(13)
<223> OTHER INFORMATION: non-natural amino acid containing an olefinic
      side chain that forms a hydrocarbon staple, (S)-2-(4-pentenyl)Ala-
      OH, or (R)-2-(4-pentenyl)Ala-OH; wherein Xaa13 forms a hydrocarbon
      staple with Xaa17
<220> FEATURE:
<221> NAME/KEY: MOD_RES
<222> LOCATION: (17)..(17)
<223> OTHER INFORMATION: non-natural amino acid containing an olefinic
      side chain that forms a hydrocarbon staple, (S)-2-(4-pentenyl)Ala-
      OH, or (R)-2-(4-pentenyl)Ala-OH; wherein Xaa13 forms a hydrocarbon
      staple with Xaa17

<400> SEQUENCE: 50

Ala Leu Val Ala Asp Phe Val Gly Tyr Lys Leu Arg Xaa Lys Gly Tyr
1               5                   10                  15

Xaa Ser Gly Ala
```

20

<210> SEQ ID NO 51
<211> LENGTH: 21
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<223> OTHER INFORMATION: See specification as filed for detailed
      description of substitutions and preferred embodiments
<220> FEATURE:
<221> NAME/KEY: MOD_RES
<222> LOCATION: (14)..(14)
<223> OTHER INFORMATION: non-natural amino acid containing an olefinic
      side chain that forms a hydrocarbon staple, (S)-2-(4-pentenyl)Ala-
      OH, or (R)-2-(4-pentenyl)Ala-OH; wherein Xaa14 forms a hydrocarbon
      staple with Xaa18
<220> FEATURE:
<221> NAME/KEY: MOD_RES
<222> LOCATION: (18)..(18)
<223> OTHER INFORMATION: non-natural amino acid containing an olefinic
      side chain that forms a hydrocarbon staple, (S)-2-(4-pentenyl)Ala-
      OH, or (R)-2-(4-pentenyl)Ala-OH; wherein Xaa14 forms a hydrocarbon
      staple with Xaa18

<400> SEQUENCE: 51

Arg Ala Leu Val Ala Asp Phe Val Gly Tyr Lys Leu Arg Xaa Lys Gly
1               5                   10                  15

Tyr Xaa Ser Gly Ala
            20

<210> SEQ ID NO 52
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<223> OTHER INFORMATION: See specification as filed for detailed
      description of substitutions and preferred embodiments
<220> FEATURE:
<221> NAME/KEY: MOD_RES
<222> LOCATION: (13)..(13)
<223> OTHER INFORMATION: non-natural amino acid containing an olefinic
      side chain that forms a hydrocarbon staple, (S)-2-(4-pentenyl)Ala-
      OH, or (R)-2-(4-pentenyl)Ala-OH; wherein Xaa13 forms a hydrocarbon
      staple with Xaa17
<220> FEATURE:
<221> NAME/KEY: MOD_RES
<222> LOCATION: (17)..(17)
<223> OTHER INFORMATION: non-natural amino acid containing an olefinic
      side chain that forms a hydrocarbon staple, (S)-2-(4-pentenyl)Ala-
      OH, or (R)-2-(4-pentenyl)Ala-OH; wherein Xaa13 forms a hydrocarbon
      staple with Xaa17

<400> SEQUENCE: 52

Ala Leu Val Ala Asp Phe Val Gly Tyr Lys Leu Arg Xaa Lys Gly Tyr
1               5                   10                  15

Xaa Cys Gly Ala
            20

<210> SEQ ID NO 53
<211> LENGTH: 21
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature

```
<223> OTHER INFORMATION: See specification as filed for detailed
      description of substitutions and preferred embodiments
<220> FEATURE:
<221> NAME/KEY: MOD_RES
<222> LOCATION: (14)..(14)
<223> OTHER INFORMATION: non-natural amino acid containing an olefinic
      side chain that forms a hydrocarbon staple, (S)-2-(4-pentenyl)Ala-
      OH, or (R)-2-(4-pentenyl)Ala-OH; wherein Xaa14 forms a hydrocarbon
      staple with Xaa18
<220> FEATURE:
<221> NAME/KEY: MOD_RES
<222> LOCATION: (18)..(18)
<223> OTHER INFORMATION: non-natural amino acid containing an olefinic
      side chain that forms a hydrocarbon staple, (S)-2-(4-pentenyl)Ala-
      OH, or (R)-2-(4-pentenyl)Ala-OH; wherein Xaa14 forms a hydrocarbon
      staple with Xaa18

<400> SEQUENCE: 53

Arg Ala Leu Val Ala Asp Phe Val Gly Tyr Lys Leu Arg Xaa Lys Gly
1               5                   10                  15

Tyr Xaa Cys Gly Ala
            20

<210> SEQ ID NO 54
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(9)
<223> OTHER INFORMATION: /note="This sequence may encompass 2-9
      residues"

<400> SEQUENCE: 54

Arg Arg Arg Arg Arg Arg Arg Arg Arg
1               5
```